US009944995B2

(12) United States Patent
Ternan et al.

(10) Patent No.: US 9,944,995 B2
(45) Date of Patent: Apr. 17, 2018

(54) **DIAGNOSTIC METHODS FOR DETECTING *CLOSTRIDIUM DIFFICILE***

(75) Inventors: Nigel G. Ternan, Portrush (GB);
Geoffrey Mcmullan, Castlerock (GB);
Christopher I. Gill, Coleraine (GB);
Shailesh Jain, Mumbai (IN)

(73) Assignee: UNIVERSITY OF ULSTER, Corelaine (GB)

( * ) Notice: Subject to any disclaimer, the term of this patent is extended or adjusted under 35 U.S.C. 154(b) by 521 days.

(21) Appl. No.: 14/128,180

(22) PCT Filed: Jun. 25, 2012

(86) PCT No.: PCT/GB2012/051483
§ 371 (c)(1),
(2), (4) Date: Feb. 11, 2014

(87) PCT Pub. No.: WO2012/176004
PCT Pub. Date: Dec. 27, 2012

(65) Prior Publication Data
US 2014/0154692 A1    Jun. 5, 2014

(30) Foreign Application Priority Data

Jun. 23, 2011   (GB) .................................. 1110712.5

(51) Int. Cl.
*C12Q 1/68*    (2018.01)
*C07H 21/02*   (2006.01)

(52) U.S. Cl.
CPC ....... *C12Q 1/689* (2013.01); *C12Q 2600/106* (2013.01)

(58) Field of Classification Search
CPC ........................ C12Q 1/689; C12Q 2600/106
See application file for complete search history.

(56) References Cited

U.S. PATENT DOCUMENTS

| 2010/0148126 A1 | 6/2010 | Guan et al. |
| 2011/0287965 A1 | 11/2011 | Tsang et al. |

FOREIGN PATENT DOCUMENTS

| WO | 2004085637 A1 | 10/2004 |
| WO | 2008152429 A1 | 12/2008 |
| WO | 2009100215 A2 | 8/2009 |
| WO | 2010039787 A1 | 4/2010 |
| WO | 2010062897 A1 | 6/2010 |
| WO | 2010062903 A2 | 6/2010 |
| WO | 2010094970 A1 | 8/2010 |
| WO | 2010/116290 A1 | 10/2010 |
| WO | 2011/008942 A2 | 1/2011 |

OTHER PUBLICATIONS

Marsden, G.L. et al., BMC Genomics, vol. 11:389, pp. 1-16 (2010).*
Marsden, G.L. et al., BMC Genomics, vol. 11:389, pp. 1-16 (2010), Additiona File 1 (AD1) pp. 145 and 326-357.*
Stabler, R.A. et al., Gut Microbes, vol. 1, pp. 269-276 (2010).*
Sebaihia, et al. "The multidrug-resistant human pathogen Clostridium difficile has a highly mobile, mosaic genome." Nature Genetics 38: 779-786 (2006).
Forgetta, et al. "Fourteen-genome comparison identifies DNA markers for severe-disease-associated strains of Clostridium difficile." Journal of Clinical Microbiology 49: 2230-2238 (2011).
Planche et al., 2008, Diagnosis of Clostridium diffi cile infection by toxin detection kits: a systematic review. The Lancet: Infectious Disease 8: 777-784.
Wilcox and Eastwood, 2009, NHS Purchasing and Supplies Agency, Centre for Evidence Based Purchasing, Evaluation Report CEP08054 <<https://www.gov.uk/government/uploads/system/uploads/attachment_data/file/216192/dh_127743.pdf>>. Last accessed May 20, 2014.
He et al., 2010, Evolutionary dynamics of Clostridium difficile over short and long time scales. PNAS 107: 7527-7532. <<http://www.pnas.org/content/107/16/7527.full.pdf+html>> Last accessed May 20, 2014.
Wilcox et al., 1996, Financial burden of hospital-acquired Clostridium difficile infection. Journal of Hospital Infection 34: 23-30 (Abstract Only). <<http://www.ncbi.nlm.nih.gov/pubmed/8880547>> Last accessed May 20, 2014.

* cited by examiner

*Primary Examiner* — Teresa E Strzelecka
(74) *Attorney, Agent, or Firm* — Fox Rothschild LLP

(57) ABSTRACT

The invention provides a method of detecting *Clostridium difficile* in a sample, comprising detecting the presence in said sample of one or more genes that have been identified as being specific to *Clostridium difficile*. Also provided is a method of diagnosing a *Clostridium difficile* infection in a subject, a method of determining the efficacy of a therapeutic regime being used to treat a *Clostridium difficile* infection and a method of testing for the presence of *Clostridium difficile* in a sample. Further provided are primer pairs and a kit suitable for use in such methods.

10 Claims, 3 Drawing Sheets

Figure 1

| 1 | 1 | 2 | 2 | 3 | 3 | 4 | 4 | 5 | 5 | 6 | 6 |
|---|---|---|---|---|---|---|---|---|---|---|---|
| 7 | 7 | 8 | 8 | 9 | 9 | 10 | 10 | 11 | 11 | 12 | 12 |
| 13 | 13 | 14 | 14 | 15 | 15 | 16 | 16 | 17 | 17 | 18 | 18 |
| 19 | 19 | 20 | 20 | 21 | 21 | 22 | 22 | 23 | 23 | 24 | 24 |
| 25 | 25 | 26 | 26 | 27 | 27 | 28 | 28 | 29 | 29 | 30 | 30 |
| 31 | 31 | 32 | 32 | 33 | 33 | 34 | 34 | 35 | 35 | 36 | 36 |
| 37 | 37 | 38 | 38 | 39 | 39 | 40 | 40 | 41 | 41 | 630 | 630 |
| E. coli | E. coli | Staph | Staph | -ve | -ve | | | | | | |

DIAGNOSTIC METHODS FOR DETECTING *CLOSTRIDIUM DIFFICILE*

The present application is the U.S. National Phase of International Patent Application Serial No. PCT/GB12/51483, filed Jun. 25, 2012, which claims the benefit of U.K. Patent Application Serial No. 1110712.5, filed Jun. 23, 2011. The aforementioned applications are hereby incorporated by reference in then entireties.

The present invention relates to methods of detecting *Clostridium difficile*, in particular in samples from a human or animal subject, such detection methods enable diagnosis of *Clostridium difficile* infections in said subject. The present methods rely on detection of certain genes which are specific for *Clostridium difficile*.

*Clostridium difficile* infection (CDI) has become a problematic nosocomial infection in hospitals and long term care facilities throughout the world. CDI is often associated with antibiotic treatment and causes diseases ranging from antibiotic associated diarrhoea to life threatening pseudomembraneous colitis. CDI is the leading cause of infectious diarrhoea among patients in hospitals worldwide.

CDI is a significant burden on the NHS and patients. It is estimated that the 1298 reported cases of CDI in Northern Ireland in 2008 will have cost the local economy a total of £39 million and resulted in the loss of 7139 bed days. In Northern Ireland, the yearly cost of CDI is the equivalent of 10.5% of the total drugs bill. The burden of CDI is not limited to the UK; CDI is also a significant burden on the Irish healthcare system and also on other healthcare providers worldwide. The ageing population, societal strategies to care for the elderly and healthcare management protocols have exacerbated the incidence of CDI. It is essential that the spread of this disease be contained, not least given the associated mortality rate of 6-15%.

Despite the fact that CDI is a problematic infection, there remain very few efficient and reliable methods available for the detection of *Clostridium difficile*. The most common methods currently used in hospitals for detecting *Clostridium difficile* are enzyme immunoassays which detect the presence of *Clostridium difficile* A and/or B toxins. Indeed, the current gold standard for *Clostridium difficile* testing is the cell culture cytotoxicity assay. However, this assay is not standardised and requires access to a continuous cell line and a certain level of technical expertise, in addition to taking up to 48 h to yield a result. Consequently, many laboratories have switched to kit-based methods. However, these kits also rely on the detection of *Clostridium difficile* toxins.

Despite an abundance of *Clostridium difficile* detection kits on the market, a recent report by the NHS Centre for Evidence Based Purchasing states that of the nine kits tested "the poor PPVs of toxin detection kits, especially in the context of widespread testing raises doubts about their appropriateness when used as single tests for the laboratory detection of *C. difficile* toxins." (Wilcox and Eastwood, NHS Purchasing and Supplies Agency, Center for Evidence based Purchasing. *Clostridium difficile* toxin detection assays, CEP08054, 2009.). This affirms the sentiments expressed by Planche et al. (The Lancet: Infectious Disease (2008) 8:777-84) in which they conducted a meta analysis of the accuracy of available toxin detection kits and came to the conclusion that there was an unacceptably low predictive rate (<50% in some cases) when patient samples are presented with low toxin titre. In addition, certain strains of *Clostridium difficile* may be toxin A−/toxin B+; in this scenario, a detection method which relies on the detection of toxin A would give a false negative result. Also, the costs associated with toxin detection kits are high.

Some researchers have proposed methods for the detection of *Clostridium difficile* by testing for the presence of *Clostridium difficile* toxin genes (WO 2011/008942 and WO 2010/116290), rather than the toxins themselves.

Other methods of testing for *Clostridium difficile* include detection of glutamate dehydrogenase (GDH) by latex agglutination. However, this test is generally performed as an initial screening procedure and is followed by *Clostridium difficile* cell culture and a second step in which toxin detection is carried out. Such methods of detecting *Clostridium difficile* are time consuming, expensive, and prone to error. Furthermore, enzymes that are detected in some *Clostridium difficile* detection methods (e.g. GDH) are present in a variety of microorganisms and thus the specificity of such methods may not be absolute.

What is needed in the art is a cost-effective, toxin independent, high-sensitivity, high-specificity method of detecting a variety of *Clostridium difficile* strains, ribotypes and clinical isolates. Preferably such a method would be straight forward to perform and offer results in a short time-frame. Preferably the methods can be performed in a culture independent fashion.

The present inventors have identified certain *Clostridium difficile* specific genes (CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961), the detection of each of which is indicative of the presence of *Clostridium difficile*. Surprisingly, the detection of each of these genes can reliably identify a large number of different strains, ribotypes and deposited isolates of *Clostridium difficile* and thus the methods of the present invention are particularly advantageous.

The present invention provides methods of detecting *Clostridium difficile*, or testing for the presence of *Clostridium difficile* in a sample, comprising detecting the presence in said sample of, or analysing said sample for the presence of, one more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes.

In one embodiment, the present invention provides a method of detecting *Clostridium difficile* in a sample, said method comprising detecting the presence in said sample of one or more genes selected from the group consisting of CD2961, CD3617, CD3618, CD3635 and CD3638, or a product of said genes. The presence of said one or more genes or product thereof is indicative of the presence of *Clostridium difficile* in said sample.

Viewed alternatively, the present invention provides a method of testing for the presence of *Clostridium difficile* in a sample, said method comprising analysing said sample for the presence of one or more genes selected from the group consisting of CD2961, CD3617, CD3618, CD3635 and CD3638, or a product of said genes. The presence of said one or more genes or product thereof is indicative of the presence of *Clostridium difficile* in said sample.

All the methods of the invention described herein conveniently comprise contacting the sample with a detection moiety which can detect one of said genes. In certain embodiments, 2 or more moieties selective for 2 or more genes may be contacted with said sample or to a series of samples from the same source. The detection moieties will generally bind specifically to the gene or its product, for example based on nucleotide base-pair binding or antigen/antibody type interactions. Suitable detection moieties are discussed in more detail below. Thus methods may then involve a step of analysing the combination of sample plus detection moiety in order to confirm the presence of detection moiety bound to said gene or gene product. The presence of such a bound conjugate may be confirmed per se or its presence derived, e.g. from the presence of the nucleic acid products of an amplification reaction enabled through binding of the detection moiety to the gene.

The complete genome (which includes the chromosome and the plasmid) sequence of *Clostridium difficile* strain 630, a virulent, and multidrug-resistant strain has been determined (Sebaihia et al., Nature Genetics, 2006, volume 38, number 7, pages 779-786). The chromosome of *Clostridium difficile* strain 630 encodes 3,776 predicted protein sequences. The plasmid of *Clostridium difficile* strain 630 carries 11 predicted coding sequences. The sequence and annotation of the *Clostridium difficile* strain 630 chromosome and plasmid have been deposited in the EMBL database under accession numbers AM180355 and AM180356, respectively. In the above mentioned Sebaihia et al. publication, each coding sequence is assigned a name which begins "CD", for example CD0001. The same nomenclature is used in the present specification. Throughout this application, references to the genes "CD2961", "CD3617", "CD3618", "CD3635" or "CD3638" etc. include coding and non-coding nucleotide sequences of these genes, unless the context dictates otherwise. The coding nucleotide sequences of genes CD2961, CD3617, CD3618, CD3635 and CD3638 are set forth in this application as SEQ ID NO:1, SEQ ID NO:2, SEQ ID NO:3, SEQ ID NO:4 and SEQ ID NO:5, respectively. Detection of one or more of SEQ ID NOs 1-5 or products thereof represents a preferred embodiment of the present invention.

As used herein, a "nucleic acid" is DNA or RNA, preferably DNA. As used herein, a "nucleotide" is a deoxyribonucleotide or a ribonucleotide, preferably a deoxyribonucleotide.

The nucleotide sequences of CD2961, CD3617, CD3618, CD3635 and CD3638 were determined in *Clostridium difficile* strain 630, but it will be understood in the art that modest sequence variation may occur between different strains and ribotypes of *Clostridium difficile*. The methods of the present invention are intended to detect one or more of these genes or gene products in all, or substantially all, strains, ribotypes and isolates of *Clostridium difficile*. The genes are defined with reference to strain 630 as discussed above and the equivalent gene sequences (homologous sequences) in other strains, ribotypes and isolates of *Clostridium difficile* can be readily determined by the skilled man. Most preferably, the methods will positively identify 100% of *Clostridium difficile* strains, ribotypes and isolates, effective methods will positively identify at least 80%, preferably at least 90%, more preferably at least 95%, e.g. at least 98% of all available *Clostridium difficile* strains, ribotypes and isolates. Thus, nucleotide sequences that are homologous to SEQ ID NO:1, SEQ ID NO:2, SEQ ID NO:3, SEQ ID NO:4 and SEQ ID NO:5 will preferably be detected by the methods of the present invention.

As referred to herein, "homologous" nucleotide sequences may have at least 70%, at least 75%, at least 80%, at least 85%, at least 90%, at least 95%, at least 96%, at least 97%, at least 98%, or at least 99% identity to the nucleic acid sequences of SEQ ID NO:1, SEQ ID NO:2, SEQ ID NO:3, SEQ ID NO:4 and SEQ ID NO:5.

Sequence alignments and percent identity calculations may be determined using any method or tool known in the art including, but not limited to, the Megalign program of the LASERGENE bioinformatics computing suite (DNASTAR Inc., Madison, Wis.), the Clustal V method of alignment (Higgins and Sharp (1989) CABIOS. 5:151-153) and the BLAST 2.0 suite of programs. Software for performing BLAST analyses is publicly available, e.g., through the National Center for Biotechnology Information. The skilled man will be able to set the parameters of these tools to suit his desired purpose.

"Homologous" nucleotide sequences may be identified using oligonucleotide primer pairs directed to SEQ ID NO:1, SEQ ID NO:2, SEQ ID NO:3, SEQ ID NO:4 and SEQ ID NO:5. Such oligonucleotide primer pairs may be capable of hybridising to, and, when combined with a nucleic acid amplification step, amplifying a portion of a nucleic acid that is homologous to SEQ ID NO:1, SEQ ID NO:2, SEQ ID NO:3, SEQ ID NO:4 or SEQ ID NO:5. The amplified portion of nucleic acid may then be sequenced and the sequence compared to an appropriate nucleic acid sequence database to identify nucleic acids homologous to SEQ ID NO:1, SEQ ID NO:2, SEQ ID NO:3, SEQ ID NO:4 or SEQ ID NO:5. Methods of identifying genes using oligonucleotide primer pairs are well known in the art.

The nucleic acid of SEQ ID: NO: 1 may be detected using the primer pair as set forth in SEQ ID NO:11 and SEQ ID NO:12. Thus, sequences homologous to SEQ ID NO: 1 may be identified using the primer pair as set forth in SEQ ID NO: 11 and SEQ ID NO:12.

The nucleic acid of SEQ ID: NO: 2 may be detected using the primer pair as set forth in SEQ ID NO:13 and SEQ ID NO:14. Thus, sequences homologous to SEQ ID NO: 2 may be identified using the primer pair as set forth in SEQ ID NO:13 and SEQ ID NO:14.

The nucleic acid of SEQ ID: NO: 3 may be detected using the primer pair as set forth in SEQ ID NO:15 and SEQ ID NO:16. Thus, sequences homologous to SEQ ID NO: 3 may be identified using the primer pair as set forth in SEQ ID NO:15 and SEQ ID NO:16.

The nucleic acid of SEQ ID: NO:4 may be detected using the primer pair as set forth in SEQ ID NO:17 and SEQ ID NO:18. Thus, sequences homologous to SEQ ID NO: 4 may be identified using the primer pair as set forth in SEQ ID NO:17 and SEQ ID NO:18.

The nucleic acid of SEQ ID: NO:5 may be detected using the primer pair as set forth in SEQ ID NO:19 and SEQ ID NO:20. Thus, sequences homologous to SEQ ID NO: 5 may be identified using the primer pair as set forth in SEQ ID NO: 19 and SEQ ID NO:20.

Thus methods of the invention which employ the above primers or sequences homologous thereto represent preferred embodiments.

It is well understood in the art that when detecting the presence of a gene in a sample, it is not necessary to detect the presence of the entire gene sequence; detecting the presence of a fragment of a gene may be indicative of the presence of the entire gene.

In a preferred method of the invention, the presence of one or more of the nucleotide sequences selected from the group consisting of SEQ ID NO:1, SEQ ID NO:2, SEQ ID NO:3, SEQ ID NO:4 and SEQ ID NO:5 is detected.

As referred to herein "one or more genes selected from the group consisting of CD2961, CD3617, CD3618, CD3635 and CD3638" means one, two, three, four or five genes selected from the group consisting of CD2961, CD3617, CD3618, CD3635 and CD3638. "One" gene means either CD2961, CD3617, CD3618, CD3635 or CD3638. "Two" genes may mean CD2961 and CD3617; CD2961 and CD3618; CD2961 and CD3635; CD2961 and CD3638; CD3617 and CD3618; CD3617 and CD3635; CD3617 and CD3638; CD3618 and CD3635; CD3618 and CD3638; or CD3635 and CD3638. "Three" genes may mean CD2961, CD3617 and CD3618; CD2961, CD3617 and CD3635; CD2961, CD3617 and CD3638; CD2961, CD3618 and CD3635; CD2961, CD3618 and CD3638; CD2961, CD3635 and CD3638; CD3617, CD3618 and CD3635; CD3617, CD3618 and CD3638; or CD3618, CD3635 and CD3638. "Four" genes may mean CD2961, CD3617, CD3618 and CD3635; CD2961, CD3618, CD3635 and CD3638; CD2961, CD3617, CD3635 and CD3638; CD2961, CD3617, CD3618, and CD3638; or CD3617, CD3618, CD3635 and CD3638. "Five" genes means CD2961, CD3617, CD3618, CD3635 and CD3638.

As referred to herein one or more of the nucleotide sequences selected from the group consisting of SEQ ID NO:1, SEQ ID NO:2, SEQ ID NO:3, SEQ ID NO:4 and SEQ ID NO:5 means one, two, three, four or five nucleotide sequences selected from the group consisting of SEQ ID NO:1, SEQ ID NO:2, SEQ ID NO:3, SEQ ID NO:4 and SEQ ID NO:5. "One" nucleotide sequence means either SEQ ID NO:1, SEQ ID NO:2, SEQ ID NO:3, SEQ ID NO:4 or SEQ ID NO:5. "Two" nucleotide sequences may mean SEQ ID NO:1 and SEQ ID NO:2; SEQ ID NO:1 and SEQ ID NO:3; SEQ ID NO:1 and SEQ ID NO:4; SEQ ID NO:1 and SEQ ID NO:5; SEQ ID NO:2 and SEQ ID NO:3; SEQ ID NO:2 and SEQ ID NO:4; SEQ ID NO:2 and SEQ ID NO:5; SEQ ID NO:3 and SEQ ID NO:4; SEQ ID NO:3 and SEQ ID NO:5; or SEQ ID NO:4 and SEQ ID NO:5. "Three" nucleotide sequences may mean SEQ ID NO:1, SEQ ID NO:2 and SEQ ID NO:3; SEQ ID NO:1, SEQ ID NO:2 and SEQ ID NO:4; SEQ ID NO:1, SEQ ID NO:2 and SEQ ID NO:5; SEQ ID NO:1, SEQ ID NO:3 and SEQ ID NO:4; SEQ ID NO:1, SEQ ID NO:3 and SEQ ID NO:5; SEQ ID NO:1, SEQ ID NO:4 and SEQ ID NO:5; SEQ ID NO:2, SEQ ID NO:3 and SEQ ID NO:4; SEQ ID NO:2, SEQ ID NO:3 and SEQ ID NO:5; or SEQ ID NO:3, SEQ ID NO:4 and SEQ ID NO:5. "Four" nucleotide sequences may mean SEQ ID NO:1, SEQ ID NO:2, SEQ ID NO:3 and SEQ ID NO:4; SEQ ID NO:1, SEQ ID NO:2, SEQ ID NO:4 and SEQ ID NO:5; SEQ ID NO:1, SEQ ID NO:3, SEQ ID NO:4 and SEQ ID NO:5; SEQ ID NO:1, SEQ ID NO:2, SEQ ID NO:3, and SEQ ID NO:5; or SEQ ID NO:2, SEQ ID NO:3, SEQ ID NO:4 and SEQ ID NO:5. "Five" nucleotide sequences means SEQ ID NO:1, SEQ ID NO:2, SEQ ID NO:3, SEQ ID NO:4 and SEQ ID NO:5.

As referred to herein, a "product" of a gene includes mRNA molecules transcribed from the gene or polypeptides encoded by the gene. It will be appreciated that an mRNA molecule will comprise the same sequence as the DNA molecule from which it was transcribed, with the exception the mRNA molecule will comprise uracil whereas the DNA molecule from which it was transcribed would instead comprise thymine at the corresponding positions.

In one embodiment, the gene product detected by the methods of the invention is an mRNA molecule. It is not necessary to detect the presence of the entire mRNA molecule (i.e. the entire mRNA nucleotide sequence); detecting the presence of a fragment of an mRNA molecule can be indicative of the presence of the entire mRNA molecule.

In another embodiment, the gene product detected by the methods of the invention is a polypeptide. A polypeptide of the sequence set forth in SEQ ID NO:6 is encoded by the nucleotide sequence of SEQ ID NO:1. A polypeptide having the sequence set forth in SEQ ID NO:7 is encoded by the nucleic acid sequence of SEQ ID NO:2. A polypeptide of the sequence set forth in SEQ ID NO:8 is encoded by the nucleotide sequence of SEQ ID NO:3. A polypeptide of the sequence set forth in SEQ ID NO:9 is encoded by the nucleotide sequence of SEQ ID NO:4. A polypeptide of the sequence set forth in SEQ ID NO:10 is encoded by the nucleotide sequence of SEQ ID NO:5. Thus, in a preferred embodiment, one or more of the polypeptides selected from the group consisting of SEQ ID NO:6, SEQ ID NO:7, SEQ ID NO:8, SEQ ID NO:9 and SEQ ID NO:10 are detected.

It will be appreciated that modest amino acid sequence variation may occur between different strains, ribotypes and isolates of *Clostridium difficile*. Thus, polypeptides homologous to SEQ ID NO:6, SEQ ID NO:7, SEQ ID NO:8, SEQ ID NO:9 or SEQ ID NO:10 will preferably be detected in the methods of the present invention. Such homologous nucleotide sequences may have at least 70%, at least 75%, at least 80%, at least 85%, at least 90%, at least 95%, at least 96%, at least 97%, at least 98%, or at least 99% identity to the polypeptide sequences of SEQ ID NO:6, SEQ ID NO:7, SEQ ID NO:8, SEQ ID NO:9 and SEQ ID NO:10.

It is not necessary to detect the presence of the entire polypeptide (i.e. the polypeptide's entire amino acid sequence); detecting the presence of a fragment of a polypeptide may be indicative of the presence of the entire polypeptide.

A number of different methods for detecting nucleic acids are known and described in the literature and any of these may be used according to the present invention. At its simplest, the nucleic acid may be detected by hybridisation to a probe (e.g. an oligonucleotide probe) and many such hybridisation protocols have been described (see e.g. Sambrook et al., Molecular cloning: A Laboratory Manual, 3rd Ed., 2001, Cold Spring Harbor Press, Cold Spring Harbor, N.Y.). Typically, the detection will involve a hybridisation step and/or an in vitro amplification step.

In one embodiment, the target nucleic acid in a sample may be detected by using an oligonucleotide with a label attached thereto, which can hybridise to the nucleic acid sequence of interest. Such a labelled oligonucleotide will allow detection by direct means or indirect means. In other words, such an oligonucleotide may be used simply as a conventional oligonucleotide probe. After contact of such a probe with the sample under conditions which allow hybridisation, and typically following a step (or steps) to remove unbound labelled oligonucleotide and/or non-specifically bound oligonucleotide, the signal from the label of the probe emanating from the sample may be detected. In preferred embodiments the label is selected such that it is detectable only when the probe is hybridised to its target.

In another embodiment, the target nucleic acid in a sample may be determined by using an oligonucleotide probe which is labelled only when hybridised to its target sequence, i.e. the probe may be selectively labelled. Conveniently, selective labelling may be achieved using labelled nucleotides, i.e. by incorporation into the oligonucleotide probe of a nucleotide carrying a label. In other words, selective labelling may occur by chain extension of the oligonucleotide probe using a polymerase enzyme which incorporates a labelled nucleotide, preferably a labelled dideoxynucleotide (e.g. ddATP, ddCTP, ddGTP, ddTTP, ddUTP). This approach to the detection of specific nucleotide sequences is sometimes referred to as primer extension analysis. Suitable primer extension analysis techniques are well known to the skilled man, e.g. those techniques disclosed in WO99/50448, the contents of which are incorporated herein by reference.

In a preferred embodiment of the present invention, the presence of genes, mRNA gene products, or fragments thereof, are detected by a primer-dependent nucleic acid amplification reaction. The amplification reaction is allowed to proceed for a duration (e.g. number of cycles) and under conditions that generate a sufficient amount of amplification product. Most conveniently the polymerase chain reaction (PCR) will be used, although the skilled man would be aware of other techniques. For instance LAR/LCR, SDA, Loop-mediated isothermal amplification and nucleic acid sequence based amplification (NASBA)/3SR (Self-Sustaining Sequence Replication) may be used. If an mRNA gene product is to be detected, it will first be converted into a cDNA molecule by reverse transcription using a reverse transcriptase enzyme to generate a cDNA molecule. Upon completion of the reverse transcription reaction, the cDNA can be used as the template for the primer-dependent nucleic acid amplification reaction. A person skilled in the art will be well aware of how to generate cDNA molecules from mRNA molecules.

Many variations of PCR have been developed, for instance Real Time PCR (also known as quantitative PCR, qPCR), hot-start PCR, competitive PCR, and so on, and these may all be employed where appropriate to the needs of the skilled man.

In one basic embodiment using a PCR based amplification, the oligonucleotide primers of the invention are contacted with a reaction mixture containing the target sequence and free nucleotides in a suitable buffer. Thermal cycling of the resulting mixture in the presence of a DNA polymerase results in amplification of the sequence between the primers.

Optimal performance of the PCR process is influenced by choice of temperature, time at temperature, and length of time between temperatures for each step in the cycle. A typical cycling profile for PCR amplification is (a) 5 minutes of DNA melting (denaturation) at 95° C.; (b) 30 seconds of DNA melting (denaturation) at 95° C.; (c) 30 seconds of primer annealing at 50-65° C.; (d) 30 seconds of primer extension at 68° C.-72° C., preferably 72° C.; and steps (b)-(d) are repeated as many times as necessary to obtain the desired level of amplification. A final primer extension step may also be performed. The final primer extension step may be performed at 68° C.-72° C., preferably 72° C. In certain embodiments the annealing step is performed at 50-60° C., e.g. 50-58° C., 52-58° C., 54-58° C., 53-57° C., or 53-55° C. In other embodiments the annealing step is performed at about 55° C. (e.g. 55° C.±4° C., 55° C.±3° C., 55° C.±2° C. 55° C.±1° C. or 55° C.±0.5° C.). The annealing step of other amplification reactions may also be performed at any of these temperatures.

The detection method of the present invention may be performed with any of the standard mastermixes and enzymes available.

Modifications of the basic PCR method such as qPCR (Real Time PCR) have been developed that can provide quantitative information on the template being amplified. Numerous approaches have been taken although the two most common techniques use double-stranded DNA binding fluorescent dyes or selective fluorescent reporter probes.

Double-stranded DNA binding fluorescent dyes, for instance SYBR Green, associate with the amplification product as it is produced and when associated the dye fluoresces. Accordingly, by measuring fluorescence after every PCR cycle, the relative amount of amplification product can be monitored in real time. Through the use of internal standards and controls, this information can be translated into quantitative data on the amount of template at the start of the reaction.

The fluorescent reporter probes used in qPCR are sequence specific oligonucleotides, typically RNA or DNA, that have a fluorescent reporter molecule at one end and a quencher molecule at the other (e.g. the reporter molecule is at the 5' end and a quencher molecule at the 3' end or vice versa). The probe is designed so that the reporter is quenched by the quencher. The probe is also designed to hybridise selectively to particular regions of complementary sequence which might be in the template. If these regions are between the annealed PCR primers the polymerase, if it has exonuclease activity, will degrade (depolymerise) the bound probe as it extends the nascent nucleic acid chain it is polymerising. This will relieve the quenching and fluorescence will rise. Accordingly, by measuring fluorescence after every PCR cycle, the relative amount of amplification product can be monitored in real time. Through the use of internal standard and controls, this information can be translated into quantitative data.

The amplification product may be detected, and amounts of amplification product can be determined by any convenient means. A vast number of techniques are routinely employed as standard laboratory techniques and the literature has descriptions of more specialised approaches. At its most simple the amplification product may be detected by visual inspection of the reaction mixture at the end of the reaction or at a desired time point. Typically the amplification product will be resolved with the aid of a label that may be preferentially bound to the amplification product. Typically a dye substance, e.g. a colorimetric, chromomeric fluorescent or luminescent dye (for instance ethidium bromide or SYBR green) is used. In other embodiments a labelled oligonucleotide probe that preferentially binds the amplification product is used.

The presence of gene CD2961 and of a nucleotide sequence of SEQ ID: NO: 1 may be detected using a primer-dependent nucleic acid amplification reaction with a forward primer comprising the sequence of SEQ ID NO: 11 and a reverse primer comprising the sequence of SEQ ID NO:12.

Thus, in a further aspect, the present invention provides a primer pair consisting of
(i) an isolated oligonucleotide comprising the nucleotide sequence of SEQ ID NO: 11 or a nucleotide sequence capable of hybridising under high stringency conditions to the sequence complementary to SEQ ID NO: 11; and
(ii) an isolated oligonucleotide comprising the nucleotide sequence of SEQ ID NO 12 or a nucleotide sequence capable of hybridising under high stringency conditions to the sequence complementary to SEQ ID NO 12.

The presence of gene CD3617 and of a nucleotide sequence of SEQ ID: NO: 2 may be detected using a primer-dependent nucleic acid amplification reaction with a forward primer comprising the sequence of SEQ ID NO:13 and a reverse primer comprising the sequence of SEQ ID NO:14.

Thus, in a further aspect, the present invention provides a primer pair consisting of
(i) an isolated oligonucleotide comprising the nucleotide sequence of SEQ ID NO: 13 or a nucleotide sequence capable of hybridising under high stringency conditions to the sequence complementary to SEQ ID NO: 13; and
(ii) an isolated oligonucleotide comprising the nucleotide sequence of SEQ ID NO 14 or a nucleotide sequence capable of hybridising under high stringency conditions to the sequence complementary to SEQ ID NO 14.

The presence of gene CD3618 and of a nucleic acid sequence of SEQ ID: NO: 3 may be detected using a primer-dependent nucleic acid amplification reaction with a forward primer comprising the sequence of SEQ ID NO: 15 and a reverse primer comprising the sequence of SEQ ID NO:16.

Thus, in a further aspect, the present invention provides a primer pair consisting of
(i) an isolated oligonucleotide comprising the nucleotide sequence of SEQ ID NO: 15 or a nucleotide sequence capable of hybridising under high stringency conditions to the sequence complementary to SEQ ID NO: 15; and
(ii) an isolated oligonucleotide comprising the nucleotide sequence of SEQ ID NO: 16 or a nucleotide sequence capable of hybridising under high stringency conditions to the sequence complementary to SEQ ID NO: 16.

The presence of gene CD3635 and of a nucleic acid sequence of SEQ ID: NO: 4 may be detected using a primer-dependent nucleic acid amplification reaction with a forward primer comprising the sequence of SEQ ID NO:17 and a reverse primer comprising the sequence of SEQ ID NO:18.

Thus, in a further aspect, the present invention provides a primer pair consisting of
(i) an isolated oligonucleotide comprising the nucleotide sequence of SEQ ID NO:17 or a nucleotide sequence capable of hybridising under high stringency conditions to the sequence complementary to SEQ ID NO:17; and
(ii) an isolated oligonucleotide comprising the nucleotide sequence of SEQ ID NO:18 or a nucleotide sequence capable of hybridising under high stringency conditions to the sequence complementary to SEQ ID NO:18.

The presence of gene CD3638 and of a nucleic acid sequence of SEQ ID: NO:5 may be detected using a primer-dependent nucleic acid amplification reaction with a forward primer comprising the sequence of SEQ ID NO:19 and a reverse primer comprising the sequence of SEQ ID NO:20.

Thus, in a further aspect, the present invention provides a primer pair consisting of
(i) an isolated oligonucleotide comprising the nucleotide sequence of SEQ ID NO:19 or a nucleotide sequence capable of hybridising under high stringency conditions to the sequence complementary to SEQ ID NO:19; and
(ii) an isolated oligonucleotide comprising the nucleotide sequence of SEQ ID NO:20 or a nucleotide sequence capable of hybridising under high stringency conditions to the sequence complementary to SEQ ID NO:20.

Throughout the text, references to SEQ ID NOs: 11, 12, 13, 14, 15, 16, 17, 18, 19, or 20 also include nucleotide sequences capable of hybridising under high stringency conditions to the sequence complementary to SEQ ID NOs: 11, 12, 13, 14, 15, 16, 17, 18, 19, or 20, respectively.

The oligonucleotide primers of the invention may comprise up to 100 nucleotides, preferably up to 80, 60, 50, 40, 30 or 25 nucleotides. The oligonucleotide primers of the invention may comprise at least 18, preferably at least 19, 20, 21, 22, 23, 24 or at least 25 nucleotides, e.g. 20-40 nucleotides. The nucleotides of the oligonucleotide can be any type of nucleotide so long as hybridisation specificity or efficiency and amplification efficiency is not detrimentally effected. The oligonucleotide may therefore be a deoxyribonucleotide, a ribonucleotide, modifications thereof (e.g. PNA, morpholino-, LNA) and mixtures thereof. DNA oligonucleotides are preferred.

High stringency conditions for hybridisation are defined as 2×SSC/50% formamide at 50° C. for binding conditions and 2×SSC at 65° C. for washing conditions (where SSC=0.15 M NaCl, 0.015 M sodium citrate, pH 7.2).

In preferred embodiments the nucleotide sequences that can hybridise to the nucleotide sequence complementary to SEQ ID NOs:11, 12, 13, 14, 15, 16, 17, 18, 19, or 20 under high stringency conditions will hybridise to all, or substantially all, e.g. at least 14, 15, 16, 17, 18, 19, 20, 21, 22, 23, 24 or 25 contiguous nucleotides of the nucleotide sequence complementary to SEQ ID NOs:11, 12, 13, 14, 15, 16, 17, 18, 19 or 20, respectively.

In the methods of the present invention, polypeptide gene products, or fragments thereof may be detected by a suitable method known in the art. Suitable methods may include any antibody-mediated detection method. Suitable antibody-mediated detection methods include immunoblotting (e.g. western blotting), immunofluorescence assays, radioimmunoassays, or ELISAs.

Depending on the conditions employed, detection of a gene or product thereof may be a partially, semi-, or fully quantitative measurement, but can also be a qualitative (or relative) measure in which results from a sample which does not contain one or more of the genes selected from the group consisting of CD2961, CD3617, CD3618, CD3635, or CD3638, or products thereof, are simply compared to results from the sample under investigation, with any differences between the two being noted without numerical values being affixed.

The methods of the invention are able to detect the presence of the genes CD2961, CD3617, CD3618, CD3635, and CD3638, or products thereof, in multiple clinically important *Clostridium difficile* strains and ribotypes. Preferred *Clostridium difficile* strains which can be detected include *Clostridium difficile* strain 630 (a *Clostridium difficile* strain of ribotype 12) and *Clostridium difficile* strain qcd32_g58 (a *Clostridium difficile* strain of ribotype 27). Preferred *Clostridium difficile* ribotypes which can be detected include 106, 078, 020, 001, 005, 026, 014 and 027. Other preferred *Clostridium difficile* ribotypes which can be detected include 078v, 015, 015-19, 023, 002, 053, 140.

The sample which is tested according to the methods of the invention is preferably a body fluid, swab or other cellular or non-cellular sample from a human. Such samples include, but are not limited to, bodily fluids which contain cellular materials and may or may not contain cells, e.g., blood, plasma, serum, urine, conjunctival secretions, seminal fluid, saliva, ocular lens fluid, lymphatic fluid, amniotic fluid, faeces/stool and the like; endocervical, urethral, rectal, vaginal, vulva-vaginal, nasopharyngeal and pulmonary samples; and archival samples with known diagnosis. Test samples may also be sections of tissues such as frozen sections.

The sample may be any sample taken from the gastrointestinal GI tract. The GI tract, also referred to as the digestive tract or alimentary canal (and which terms may be used interchangeably with GI tract) is the continuous series of organs beginning at the mouth and ending at the anus. Specifically this sequence consists of the mouth, the pharynx, the oesophagus, the stomach, the duodenum, the small intestine, the large intestine and the anus. These organs can be subdivided into the upper GI tract, consisting of the mouth, pharynx, oesophagus, stomach, and duodenum, and the lower GI tract, consisting of the jejunum, the ileum (together the small intestine), the cecum, the colon, the rectum (together the large intestine) and the anus.

A GI tract sample of use in the invention may include, but is not limited to any fluid or solid taken from the lumen or surface of the GI tract or any sample of any of the tissues that form the organs of the GI tract. Thus the sample may be any luminal content of the GI tract (e.g. stomach contents, intestinal contents, mucus and faeces/stool, or combinations thereof) as well as samples obtained mechanically from the GI tract e.g. by swab, rinse, aspirate or scrape of a GI tract cavity or surface or by biopsy of a GI tract tissue/organ.

The sample can also be obtained from part of a GI tract tissue/organ which has been removed surgically. The sample may be a portion of the excised tissue/organ. In embodiments where the sample is a sample of a GI tract tissue/organ the sample may comprise a part of the mucosa, the submucosa, the muscularis externa, the adventitia and/or the serosa of the GI tract tissue/organ. Such tissue samples may be obtained by biopsy during an endoscopic procedure.

Samples may also be sections of tissues such as frozen sections.

Samples of use in the invention may also include environmental samples, preferably samples from a hospital or other clinical setting. Examples of such environmental samples include samples obtained from surfaces (e.g. floors), samples obtained from clothing, samples obtained from toilets, commodes, bedpans and the like, samples obtained from clinical devices (e.g. endoscopes), samples of the water supply, or air treatment apparatus of the hospital or other clinical setting, and samples obtained from the hands of healthcare workers.

The term "sample" also encompasses any material derived by processing a biological sample. Derived materials include, but are not limited to, cells (or their progeny) isolated from the sample (e.g. clinical isolates of *Clostridium difficile*), cell components, proteins/peptides and nucleic acid molecules (DNA or RNA) extracted from the sample. Processing of biological samples to obtain a test sample may involve one or more of: filtration, distillation, centrifugation, extraction, concentration, dilution, purification, inactivation of interfering components, addition of reagents, and the like.

The subject may be any human or non-human animal subject, but more particularly may be a vertebrate, e.g. an animal selected from mammals, birds, amphibians, fish and reptiles. The animal may be a livestock or a domestic animal or an animal of commercial value, including laboratory animals or an animal in a zoo or game park. Preferably the subject is a human. The subject may be of any age, e.g. an infant, a child, a juvenile, an adolescent or an adult.

As mentioned previously, the presence of one or more genes selected from the group consisting of CD2961, CD3617, CD3618, CD3635, and CD3638, or product thereof, is indicative of the presence of *Clostridium difficile* in a sample. Accordingly, the presence of one or more genes selected from the group consisting of CD2961, CD3617, CD3618, CD3635, and CD3638, or product thereof is indicative of the presence of *Clostridium difficile* and/or a *Clostridium difficile* infection in the subject from whom the sample was taken.

Thus, in a further aspect, the present invention provides a method of diagnosing a *Clostridium difficile* infection in a subject, said method comprising detecting the presence of one or more genes selected from the group consisting of CD2961, CD3617, CD3618, CD3635 and CD3638, or a product of said genes, in a sample that has been obtained from a subject. The presence of said one or more genes or product thereof is indicative of the presence of *Clostridium difficile* in said sample. As the sample has been obtained from said subject, the presence of one or more genes selected from the group consisting of CD2961, CD3617, CD3618, CD3635 and CD3638, or a product of said genes, in the sample is diagnostic of a *Clostridium difficile* infection in the subject from whom the sample has been obtained. All discussion of the various features of the methods of the invention and preferred embodiments apply mutatis mutandis to this aspect of the invention.

The methods of the present invention may be repeated over a period of time (e.g. one week or one month) on further samples that have been obtained from a subject undergoing treatment for a *Clostridium difficile* infection. Such repeated performance of the methods of the invention may yield information that is useful in determining the efficacy of the therapeutic regime being used to treat the *Clostridium difficile* infection. For example, failure to detect the presence of one or more genes selected from the group consisting of CD2961, CD3617, CD3618, CD3635 and CD3638, or a product of said genes, in a sample obtained from a subject being treated for a *Clostridium difficile* infection may indicate that the subject no longer has a *Clostridium difficile* infection. If quantitative methods are used, then a reduction in the amount of one or more genes selected from the group consisting of CD2961, CD3617, CD3618, CD3635 and CD3638, or a product of said genes, in a sample obtained from a subject being treated for a *Clostridium difficile* infection may indicate that the therapeutic regime is being effective.

Thus, in another aspect, the present invention provides a method of determining the efficacy of a therapeutic regime being used to treat a *Clostridium difficile* infection, said method comprising:

(i) detecting the presence of one or more genes selected from the group consisting of CD2961, CD3617, CD3618, CD3635 and CD3638, or a product of said genes, in a sample that has been obtained from a subject being treated for a *Clostridium difficile* infection; and (ii) repeating step (i) on one or more further samples that have been obtained from the subject being treated for a *Clostridium difficile* infection.

Thus, for example, further samples will be obtained during the course of the treatment and/or after the treatment period has ended.

All discussion of the various features of the methods of the invention and preferred embodiments apply mutatis mutandis to this aspect of the invention.

In a further aspect the invention provides kits comprising one or more detection moieties for the detection of one or more genes selected from the group consisting of CD2961, CD3617, CD3618, CD3635 and CD3638, or a product of said genes. Preferably the detection moiety is an oligonucleotide, which may be labelled or unlabelled and may form part of a primer pair of oligonucleotides designed for participation in an amplification reaction. Suitable moieties include, but are not limited to antibodies directed against the polypeptide products of CD2961, CD3617, CD3618, CD3635 or CD3638, and the oligonucleotide primers described above. Preferably the kit comprises one or more of the primer pairs described above as detection moieties.

The kits of the invention are designed for use in the methods of the invention and may comprise further components. Each component may be provided in a separate compartment or vessel. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

The kit may also be provided with instructions for using the kit in the detection of *Clostridium difficile* (or for testing a sample for the presence of *Clostridium difficile*), or with directions for how such instructions may be obtained.

Further components might optionally be any or all of the means, e.g. buffers, enzymes etc. for performing an amplification and/or primer extension reaction with the oligonucleotides of the invention. For instance, the kits may optionally contain a PCR reaction buffer, nucleotide triphosphates (which may be labelled, e.g. labelled ddNTPs), further oligonucleotide primers, or DNA polymerases, preferably a thermostable polymerase such as Taq polymerase.

Further components might optionally be any or all of the means, e.g. buffers, enzymes etc. for performing a reverse transcription reaction. For instance a reverse transcriptase, RNA specific primers, an RT reaction buffer, and nucleotide triphosphates.

Further components might optionally be any or all of the means to take the sample. For instance such means might include dipsticks, biopsy apparatus, swabbing devices, pouches or vessels. Preferably these means will be provided in sterile form.

Further components might optionally be any or all of the means to purify or refine the sample. For instance means to isolate or concentrate cells in a sample, e.g. cell binding solid supports or filtration devices. In other embodiments the means to purify or refine the sample might be any or all of the means for extracting nucleic acid from a sample. For instance cell lysis reagents (e.g. chaotropic salts, alcohols, detergents, membrane altering compounds), nucleic acid binding solid supports or nucleic acid precipitating agents (e.g. salts, alcohols).

Further components might optionally be any or all of the means to detect amplified nucleic acid. For instance the labels described herein (e.g. double stranded DNA binding dyes, labelled oligonucleotide probes), apparatus to detect these labels, electrophoresis materials and apparatus, or chromatography materials and apparatus.

In another aspect, as an alternative to the five target genes described in detail above, the methods described herein may be performed by analysing for, or detecting the presence of, one or more of the genes selected from the group consisting of, CD0588, CD0638, CD1234, CD1423, CD1424, CD1487, CD1543a, CD1728, CD1794, CD1897, CD1906, CD2046, CD2098, CD2216, CD2248, CD2264, CD2274, CD2300, CD2306, CD2309, CD2563, CD3188, CD3288, CD3321, CD3367, CD3369, CD3609 and CD3656, or a product of said genes. Of this further group of genes, one or more of the genes selected from the group consisting of CD0638, CD1424, CD1487, CD1543a, CD1794, CD1906, CD2046, CD2098, CD2216, CD2264, CD2274, CD2309, CD3188, CD3288, CD3367 and CD3609 are preferred. One or more of the genes selected from the group consisting of CD3635, CD3638, CD0638, CD1424, CD1487, CD1543a, CD1794, CD1906, CD2046, CD2098, CD2216, CD2264, CD2274, CD2309, CD3188, CD3288, CD3367 and CD3609, are especially preferred.

Preferred embodiments of the methods and kits described above apply, mutatis mutandis, to the detection of, or analysis for, one or more of these further groups of genes.

Thus, the invention provides a method of detecting *Clostridium difficile* in a sample, said method comprising detecting the presence in said sample of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes. The presence of said one or more genes or product thereof is indicative of the presence of *Clostridium difficile* in said sample.

In a further aspect, the present invention also provides a method of diagnosing a *Clostridium difficile* infection in a subject, said method comprising detecting the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes, in a sample that has been obtained from a subject. The presence of said one or more genes or product thereof is indicative of the presence of *Clostridium difficile* in said sample. As the sample has been obtained from said subject, the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes, in the sample is diagnostic of a *Clostridium difficile* infection in the subject from whom the sample has been obtained.

In another aspect, the present invention provides a method of determining the efficacy of a therapeutic regime being used to treat a *Clostridium difficile* infection, said method comprising:

(i) detecting the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes, in a sample that has been obtained from a subject being treated for a *Clostridium difficile* infection; and (ii) repeating step (i) on one or more further samples that have been obtained from the subject being treated for a *Clostridium difficile* infection.

In a further aspect, the present invention provides a method of testing for the presence of *Clostridium difficile* in a sample, said method comprising analysing said sample for the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961, or a product of said genes. The presence of said one or more genes or product thereof is indicative of the presence of *Clostridium difficile* in said sample.

In a further aspect the present invention provides a primer pair selected from the group consisting of (a) an isolated oligonucleotide comprising the nucleotide sequence of SEQ ID NO: 67 or a nucleotide sequence capable of hybridising under high stringency conditions to the sequence complementary to SEQ ID NO: 67; and
an isolated oligonucleotide comprising the nucleotide sequence of SEQ ID NO: 68 or a nucleotide sequence capable of hybridising under high stringency conditions to the sequence complementary to SEQ ID NO: 68;

(b) an isolated oligonucleotide comprising the nucleotide sequence of SEQ ID NO: 13 or a nucleotide sequence capable of hybridising under high stringency conditions to the sequence complementary to SEQ ID NO: 13; and an isolated oligonucleotide comprising the nucleotide sequence of SEQ ID NO 14 or a nucleotide sequence capable of hybridising under high stringency conditions to the sequence complementary to SEQ ID NO 14;

(c) an isolated oligonucleotide comprising the nucleotide sequence of SEQ ID NO: 15 or a nucleotide sequence capable of hybridising under high stringency conditions to the sequence complementary to SEQ ID NO: 15; and an isolated oligonucleotide comprising the nucleotide sequence of SEQ ID NO: 16 or a nucleotide sequence capable of hybridising under high stringency conditions to the sequence complementary to SEQ ID NO: 16;

(d) an isolated oligonucleotide comprising the nucleotide sequence of SEQ ID NO:17 or a nucleotide sequence capable of hybridising under high stringency conditions to the sequence complementary to SEQ ID NO:17; and an isolated oligonucleotide comprising the nucleotide sequence of SEQ ID NO:18 or a nucleotide sequence capable of hybridising under high stringency conditions to the sequence complementary to SEQ ID NO:18;

(e) an isolated oligonucleotide comprising the nucleotide sequence of SEQ ID NO:19 or a nucleotide sequence capable of hybridising under high stringency conditions to the sequence complementary to SEQ ID NO:19; and an isolated oligonucleotide comprising the nucleotide sequence of SEQ ID NO:20 or a nucleotide sequence capable of hybridising under high stringency conditions to the sequence complementary to SEQ ID NO:20;

(f) an isolated oligonucleotide comprising the nucleotide sequence of SEQ ID NO:37 or a nucleotide sequence capable of hybridising under high stringency conditions to the sequence complementary to SEQ ID NO: 37; and an isolated oligonucleotide comprising the nucleotide sequence of SEQ ID NO:38 or a nucleotide sequence capable of hybridising under high stringency conditions to the sequence complementary to SEQ ID NO:38;

(g) an isolated oligonucleotide comprising the nucleotide sequence of SEQ ID NO: 39 or a nucleotide sequence capable of hybridising under high stringency conditions to the sequence complementary to SEQ ID NO: 39; and an isolated oligonucleotide comprising the nucleotide sequence of SEQ ID NO: 40 or a nucleotide sequence capable of hybridising under high stringency conditions to the sequence complementary to SEQ ID NO: 40;

(h) an isolated oligonucleotide comprising the nucleotide sequence of SEQ ID NO: 41 or a nucleotide sequence capable of hybridising under high stringency conditions to the sequence complementary to SEQ ID NO: 41; and an isolated oligonucleotide comprising the nucleotide sequence of SEQ ID NO: 42 or a nucleotide sequence capable of hybridising under high stringency conditions to the sequence complementary to SEQ ID NO: 42;

(i) an isolated oligonucleotide comprising the nucleotide sequence of SEQ ID NO: 43 or a nucleotide sequence capable of hybridising under high stringency conditions to the sequence complementary to SEQ ID NO: 43; and an isolated oligonucleotide comprising the nucleotide sequence of SEQ ID NO; 44 or a nucleotide sequence capable of hybridising under high stringency conditions to the sequence complementary to SEQ ID NO: 44;

(j) an isolated oligonucleotide comprising the nucleotide sequence of SEQ ID NO: 45 or a nucleotide sequence capable of hybridising under high stringency conditions to the sequence complementary to SEQ ID NO: 45; and an isolated oligonucleotide comprising the nucleotide sequence of SEQ ID NO: 46 or a nucleotide sequence capable of hybridising under high stringency conditions to the sequence complementary to SEQ ID NO: 46;

(k) an isolated oligonucleotide comprising the nucleotide sequence of SEQ ID NO: 47 or a nucleotide sequence capable of hybridising under high stringency conditions to the sequence complementary to SEQ ID NO: 47; and an isolated oligonucleotide comprising the nucleotide sequence of SEQ ID NO: 48 or a nucleotide sequence capable of hybridising under high stringency conditions to the sequence complementary to SEQ ID NO: 48;

(l) an isolated oligonucleotide comprising the nucleotide sequence of SEQ ID NO: 49 or a nucleotide sequence capable of hybridising under high stringency conditions to the sequence complementary to SEQ ID NO: 49; and an isolated oligonucleotide comprising the nucleotide sequence of SEQ ID NO:50 or a nucleotide sequence capable of hybridising under high stringency conditions to the sequence complementary to SEQ ID NO: 50;

(m) an isolated oligonucleotide comprising the nucleotide sequence of SEQ ID NO: 51 or a nucleotide sequence capable of hybridising under high stringency conditions to the sequence complementary to SEQ ID NO: 51; and an isolated oligonucleotide comprising the nucleotide sequence of SEQ ID NO: 52 or a nucleotide sequence capable of hybridising under high stringency conditions to the sequence complementary to SEQ ID NO 52;

(n) an isolated oligonucleotide comprising the nucleotide sequence of SEQ ID NO: 53 or a nucleotide sequence capable of hybridising under high stringency conditions to the sequence complementary to SEQ ID NO: 53; and an isolated oligonucleotide comprising the nucleotide sequence of SEQ ID NO: 54 or a nucleotide sequence capable of hybridising under high stringency conditions to the sequence complementary to SEQ ID NO 54;

(o) an isolated oligonucleotide comprising the nucleotide sequence of SEQ ID NO: 55 or a nucleotide sequence capable of hybridising under high stringency conditions to the sequence complementary to SEQ ID NO: 55; and an isolated oligonucleotide comprising the nucleotide sequence of SEQ ID NO: 56 or a nucleotide sequence capable of hybridising under high stringency conditions to the sequence complementary to SEQ ID NO: 56;

(p) an isolated oligonucleotide comprising the nucleotide sequence of SEQ ID NO: 57 or a nucleotide sequence capable of hybridising under high stringency conditions to the sequence complementary to SEQ ID NO: 57; and an isolated oligonucleotide comprising the nucleotide sequence of SEQ ID NO: 58 or a nucleotide sequence capable of hybridising under high stringency conditions to the sequence complementary to SEQ ID NO: 58;

(q) an isolated oligonucleotide comprising the nucleotide sequence of SEQ ID NO: 59 or a nucleotide sequence capable of hybridising under high stringency conditions to the sequence complementary to SEQ ID NO: 59; and an isolated oligonucleotide comprising the nucleotide sequence of SEQ ID NO: 60 or a nucleotide sequence capable of hybridising under high stringency conditions to the sequence complementary to SEQ ID NO: 60;

(r) an isolated oligonucleotide comprising the nucleotide sequence of SEQ ID NO: 61 or a nucleotide sequence capable of hybridising under high stringency conditions to the sequence complementary to SEQ ID NO: 61; and an isolated oligonucleotide comprising the nucleotide sequence of SEQ ID NO: 62 or a nucleotide sequence capable of hybridising under high stringency conditions to the sequence complementary to SEQ ID NO 62;

(s) an isolated oligonucleotide comprising the nucleotide sequence of SEQ ID NO: 63 or a nucleotide sequence capable of hybridising under high stringency conditions to the sequence complementary to SEQ ID NO: 63; and an isolated oligonucleotide comprising the nucleotide sequence of SEQ ID NO: 64 or a nucleotide sequence capable of hybridising under high stringency conditions to the sequence complementary to SEQ ID NO: 64;

(t) an isolated oligonucleotide comprising the nucleotide sequence of SEQ ID NO: 65 or a nucleotide sequence capable of hybridising under high stringency conditions to the sequence complementary to SEQ ID NO: 65; and an isolated oligonucleotide comprising the nucleotide sequence of SEQ ID NO: 66 or a nucleotide sequence capable of hybridising under high stringency conditions to the sequence complementary to SEQ ID NO: 66; and (u) an isolated oligonucleotide comprising the nucleotide sequence of SEQ ID NO: 11 or a nucleotide sequence capable of hybridising under high stringency conditions to the sequence complementary to SEQ ID NO: 11; and an isolated oligonucleotide comprising the nucleotide sequence of SEQ ID NO: 12 or a nucleotide sequence capable of hybridising under high stringency conditions to the sequence complementary to SEQ ID NO: 12.

In another aspect, the present invention provides a kit comprising one or more detection moieties for the detection of one or more genes selected from the group consisting of CD3609, CD3617, CD3618, CD3635, CD3638 CD0638, CD1424, CD1487, CD1543a, CD1794, CD1906, CD2046, CD2098, CD2216, CD2264, CD2274, CD2309, CD3188, CD3288, CD3367 and CD2961, or a product of said genes.

Preferred embodiments and other exemplification of the methods, kits and primers discussed above in relation to genes selected from the group consisting of CD2961, CD3617, CD3618, CD3635 and CD3638 apply, mutatis mutandis, to the aspects of the invention relating to one or more of the genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961.

Likewise, all of the definitions and discussion above in relation to genes selected from the group consisting of CD2961, CD3617, CD3618, CD3635 and CD3638 apply, mutatis mutandis, to the aspects of the invention relating to one or more of the genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961.

List of Nucleotide and Amino Acid Sequences Disclosed Herein and their Sequence Identifiers (SEQ ID NOs)

All nucleotide sequences are recited herein 5' to 3' in line with convention in this technical field.

```
(coding nucleotide sequence of CD2961)
                                                            SEQ ID NO: 1
ATGGCTTTTGAAATAATAAAAAGCATTGTTGAGGCAGAGCAGACAGCAGACAGTATCAAAGTAAAAGC

TGTTACTGATGCAGAGTCTATCAGAGCTGATGCTGTAAACAAATGTGAAAGCATATTTGCTGATGTAA

AAAAACAAGCAAAGCTTATGGAAGAAACTCTTATTGAGAAGGCAGTCACCGACAGTAGAGCAGAGGTT

GATAAAATCTTAGCTAATGCTAAAAGTGAATGTCTGAAAATTGAAAAAACTGCTGAAGAAAGAAAAAG

TAAGGCTATTGAAGCGGTTATTGGAAAGGTAGTGAGATAA (coding nucleotide sequence of CD3617)
                                                            SEQ ID NO: 2
ATGGTAAATATGAATATTATAGAAATTCGCTCAGATAAAATATACAAGAAGATAATGGAT

GCACCAATAAACAAAAAGAAGATATATACAGATATGAATTAATGAAGCCTTTTGAATTT

AAGTGGAAGTGTATGAATGTTCCAATAGTTGCTAGACAGAAAGGTGGATATGATGTAATT

ATAGCAAGTGAAATGTTAGGGGTTTTATCGCCTAAGGATATTGATGAAAAGCAAAAAAAG

AATATAAATGTGTTATCTGCTGATAAAATTTGGGCCACTTGTAAAGAAACCATAGAAAAC

TCTATAAATGCTTTTATAAAAGAAGGGTATGATTTAAACATTAAGGACTATAAATATTCA

ATATTATTGGCGAATCCAAATAGTCCTTATACAATATTAAGTGATGGATACTGGGGTGAT

GGTGGGATTCCTGGATATATATTTCTATCATTGGTTCCTAATGAATATACTATCAATAGA

TTACCAGTATTAATAGCACATGAATGTAATCACAATATTAGATTTCAGTTTATAGAGTGG

AATAATAATATAACATTAGAAGAAATGATGATAAATGAAGGTCTTGCAGAAAATTTTGCA

ACATGGATGTTTGGAGAGGAAATGTTAGGACCTTGGGTCAGTAGAACAGATATCGAAACA

TTAAATACTTATATAAAGCCAATAATAAAAAGTGCTTTAAAAGAAACTGGATTTCAAAAT

ATAACATCTTATCTTTATGGTGATGATATAGCTAAAATGCAAGGATATTTTCCAGTAGGG

TTGCCTTATTGTGCAGGATATGCTTGTGGATATTATATGATTAAGTATTATTTAGAAAAG

ACAAATAAATCAATAATCGAAGCGACTTTATTGCCTTATAGTGAGATAATCGAAGCAGTA

AAAGAGTTTTGGGAATAA
```

-continued (coding nucleotide sequence of CD3618)
SEQ ID NO: 3
TTGGTCATGCTAACTCCATATTTAATATTTAATGGTACTTGTGAAAAAGCATTTAATTTT

TATGCTGAGGCTTTCGGAGGAGGAAAAACTATATTTGCGCGATTAGACAGCAATCCAAAC

AATCCTGTTATGCACGCAAGTGTTACTTTCACAAAATACGAAGGTTGTATAATGGGTGCG

GATACAGACAAGCCTGTTGTAATTTCTGGCATGGCGATTTGTGTTGTTCTACCATCTCGA

GAAGCGATAGAAGAAATATCTGTAAAACTTGCCGAAGGTGGTACACTTGTACAAGAATTT

TTACCACACCCACCACCACATCAAAATGATGGCGCTGCTGAAGTACTTGATAGGTATGGG

TATACTTGGTATTTAAGTACATAG (coding nucleotide sequence of CD3635)
SEQ ID NO: 4
ATGGCTATGGGTTTTGAATTTAAAATAATGAGAAGTTTAATATATGTAGGACTTGCCAAG

GAAGAATATAGACCTAAGCTAATGGACTGGTTATATCGTCACCATATTCCAGATAGTATT

AGCACTTTTGGACCATATTGTACTAAATATGCCTTTTATCAAGCATATCCTACACCAAAT

GAAGGTGAGCGTTTTGGTGCACGTAAGATGCAACTAACAGAACATTATTGGCTTGTAGAT

GAACATATGCCTGAGATGGCAAATAGAATTATGACAGAATATATGCCTATGGATGTTCTA

CGTTGGCAAGGGTGTATACCAGATGTAGAAAATAAAAGGGTTCATGAAAATGCAGAAAGT

GGAGATGCAGGACGTGCAGTAGGTGGAGATAATGGATGTCCACCATTTATATTTGCCTTT

GTTCCAATAAACTGGGAAGAAGACTTTAGAGGAAAAGGACGTACTGTACAAGATGGACCA

AACTATCGTTGGCAATTTATGATTAAGTATCCAGATGGTATCTCTAAAGAAGAAGGAGAA

AAATGGTTCTATGATGAGGTAGTGCCATACTTTACAAACTGTTGCTATGTTAATCGTTTT

GTCAGTAGTAAAATAATGATTAATTATGGAGCAACTGCTTTTGACCGTGTATCAGAACTA

TGGTTTGAAGGGGAAGAAGAATGGTATAAAGCTGTGGTTGAAGAAACAAAGTCGTTTATT

AAAAAACCAGAATGGGCACAAGAAGAGGAGTTCCCATATTTAAAACCACAATTCAATATC

GCATCAGTATTCTTAGGTGATATAGCAACTATGGATGCATACTCACAGTATCGTGGATAT

ATACCAATGAGATAA (coding nucleotide sequence of CD3638)
SEQ ID NO: 5
ATGGAAGATAAATTTTATGCAAAAGGCAACGGAAATAACGGATATATTAAAAATCTTGAA

GTTTGTTCCTTTAATAACTTAGATGGAACTTGTGGAATGTTTCAAATGGCTCTGTACAAA

AGAGATGAAAAATACTATTTATATGGATGCTGTTTTGGAGGAAATAAAAAAAATGGAGTA

ATGATTAGCGATATTACAGACCCTTATAATCCACAATTTATAAAACATTTTCAAATGTTA

GACCCTAAAGAGTATCCTACAACAACAACTCCCAAAATTCAAATAGCAGATGATTTAATG

ATAGTAGCAATGAGTTGTGGAAGTGGACCAGGAGCACTTGTTGACCAAGCTAAATTAGCA

AATATTAAGTGTGAAGCAGGAATTAGAATATACAGTTTAAAAGAAGACCCTTTAAATCCT

AAGTTTTTAGGATATTGGGATTGTGGCTTAAAGCATGTAATGGGTGTTCATAGATTTATG

TACAATGGTGGAAGATATGTACATTTATCAAGTGATTGTGTTGGCTTTGAAGGTCTGATT

TATAGGGTCATAGATATAATAAATCCTACTAATCCAGTGGAAATAGGTAAATGGTGGAGA

CCAGACCAATATGCAGATGGATATCCAAATAGAACTTTTGATGCAGGAGCACCTCATTGC

CCAGAATTTATGGATAAAGGATGGCTTCATGGACCTCCATTTGTAAGAGACGGAAAAGCA

TATTGTGGTTATGGAGGAGCTGGTTTAGTTGTATTAGATGTTGAAGATTTAACAAGACCA

AGATGCTTAGGTGAATTGCCATTTACGCCTGCATTTTCTAGTAGACTTGCAGGTGCAAGA

ACTCATACAGCATTACCATTGCCAGGAAGAGATTTAGTCGTTGTTCAAAATGAGGGAGAA

AGATTCCAGTTCTTTAAACCAGATAACATTACAGATGTTCAAGCTATGAATAATATACAT

-continued

```
ATGGTTGATGTTAGTGACCCAACAAAACCAACATTAATTGCTCAATTTCCATATCCTGAA

GTTCCAAAAGATTTCCCTTATCCTAACTTTAATGTTGCGGGATTAGGAAAACCAGGGCCA

TTTGGCCCACATAATCTTCATGAACCAATGGATAATAAGCCATGGTTAGAGCAAAGAGGA

GATAGAGTATATTGCTGTTATTTCCATGCAGGGCTAAGGGTTTATGATGTATCAGACCCA

TATTATATCAAAGAGCTAGCATATTTTATACCACCAAATCCAAATAAAACACCAGAAGAA

TCTTATTTCCCAGGATTCCCAGGACCACGCTTGGCAGTAACAGAAGATCTTATCGTTGAT

GATAGAGGCTACATCATCATAGATGCTTTAGATGATGGATTCTATATATTAAAAATGAAA

GATGATTAA
```

(amino acid sequence encoded by CD2961)
SEQ ID NO: 6
```
MAFEIIKSIVEAEQTADSIKVKAVTDAESIRADAVNKCESIFADVKKQAKLMEETLIEKAVTDSRAEV

DKILANAKSECLKIEKTAEERKSKAIEAVIGKVVR
```

(amino acid sequence encoded by CD3617)
SEQ ID NO: 7
```
MVNMNIIEIRSDKIYKKIMDAPINKKEDIYRYELMKPFEFKWKCMNVPIVARQKGGYDVIIASEMLGV

LSPKDIDEKQKKNINVLSADKIWATCKETIENSINAFIKEGYDLNIKDYKYSILLANPNPYTILSDGY

WGDGGIPGYIFLSLVPNEYTINRLPVLIAHECNHNIRFQFIEWNNNITLEEMMINEGLAENFATWMFG

EEMLGPWVSRTDIETLNTYIKPIIKSALKETGFQNITSYLYGDDIAKMQGFPVGLPYCAGYACGYYMI

KYYLEKTNKSIIEATLLPYSEIIEAVKEFWE
```

(amino acid sequence encoded by CD3618)
SEQ ID NO: 8
```
MVMLTPYLIFNGTCEKAFNFYAEAFGGGKTIFARLDSNPNNPVMHASVTFTKYEGCIMGADTDKPVVI

SGMAICVVLPSREAIEEISVKLAEGGTLVQEFLPHPPPHQNDGAAEVLDRYGYTWYLST
```

(amino acid sequence encoded by CD3635)
SEQ ID NO: 9
```
MAMGFEFKIMRSLIYVGLAKEEYRPKLMDWLYRHHIPDSISTFGPYCTKYAFYQAYPTPNEGERFGAR

KMQLTEHYWLVDEHMPEMANRIMTEYMPMDVLRWQGCIPDVENKRVHENAESGDAGRAVGDNGCPPFI

FAFVPINWEEDFRGKGRTVQDGPNYRWQFMIKYPDGISKEEGEKWFYDEVVPYFTNCCYVNRFVSSKI

MINYGATAFDRVSELWFEGEEEWYKAVVEETKSFIKKPEWAQEEEFPYLKQFNIASVFLGDIATMDAY

SQYRGYIPMR
```

(amino acid sequence encoded by CD3638)
SEQ ID NO: 10
```
MEDKFYAKGNGNNGYIKNLEVCSFNNLDGTCGMFQMALYKRDEKYYLYGCCFGGNKKNGVMISDITDP

YNPQFIKHFQMLDPKEYPTTTTPKIQIADDLMIVAMSCGSGPGALVDQAKLANIKCEAGRIYSLKEDP

LNPKFLGYWDCGLKHVMGVHRFMYNGGRYVHLSSDCVGFEGLIYRVIDIINPTNPVEIGKWWRPDQYA

DGYPNRTFDAGAPHCPEFMDKGWLHGPPFVRDGKAYCGYGGAGLVVLDVELTRPRCLGELPFTPAFSS

RLAGARTHTALPLPGRDLVVVQNEGERFQFFKPDNITDVQAMNNIHMVDVSDPTKPTLIAQFPYPEVP

KDFPYPNFNVAGLGKPGPFGPHNLHEPMDNKPWLEQRGDRVCCYFHAGLRVYDVSDPYYIKELAYFIP

PNPNKTPEESYFPGFPGPRLAVTEDLIVDDRGYIIIDALDDGFYILKMKDD
```

(forward primer directed to SEQ ID NO: 1)
SEQ ID NO: 11
AGAAGGCAGTCACCGACAGT (reverse primer directed to SEQ ID NO: 1)
SEQ ID NO: 12
CCTTTCCAATAACCGCTTCA (forward primer directed to SEQ ID NO: 2)
SEQ ID NO: 13
GATGGATACTGGGGTGATGG -continued (reverse primer directed to SEQ ID NO: 2)
SEQ ID NO: 14
AAGGCAATAAAGTCGCTTCG (forward primer directed to SEQ ID NO: 3)
SEQ ID NO: 15
TTTAATGGTACTTGTGAAAAAGCAT (reverse primer directed to SEQ ID NO: 3)
SEQ ID NO: 16
GCCATCATTTTGATGTGGTG (forward primer directed to SEQ ID NO: 4)
SEQ ID NO: 17
CATATGCCTGAGATGGCAAA (reverse primer directed to SEQ ID NO: 4)
SEQ ID NO: 18
CTTGTGCCCATTCTGGTTTT (forward primer directed to SEQ ID NO: 5)
SEQ ID NO: 19
GGATGCTGTTTTGGAGGAAA (reverse primer directed to SEQ ID NO: 5)
SEQ ID NO: 20
AAATTCTGGGCAATGAGGTG (coding nucleotide sequence of CD0638)
SEQ ID NO: 21
TTGTTTATTTTGAATTTTGGAGGATTAATTATGGATTCAAATAATAATACTATAAAATCA

ACTGTTAAAAAGGGTATTTCTTTTGGTTCTTGTTTAGCAATGATTATTTCTTATACTGCA

TGGAAATCTATTCCATGGGCTATTTTTCATGGCTTAATGAGTTGGATATATGTACTTTAT

TATTGGGTTAAGTATGCATAG (coding nucleotide sequence of CD1424)
SEQ ID NO: 22
ATGTTTAGAGATGAAATGGATAAATGTACACACATGTTAACTGCTTATATTAGTAGTTTA

TATGATTATTGTGATTTTATAGATACACAGCTAGATGATTTTATACTAGAGTACGGAGAA

AATGTAGTAGAATCTTGTTTACATCAAGTGATGGTATTGGTAAGTAAGTATAATTAA (coding nucleotide sequence of CD1487)
SEQ ID NO: 23
ATGGAAAATGATACTATTAAGGCTGATGATATTCTCAATTATTGTCTATCAAACTTAGAT

GATGTTGTACTAATGGATAGTTGGGGGGAACGAGCAATTTACTACAATCCTAATGGTGTT

TTAAAGCGAGGGGTATATGTTCTTACCATTAAGGAAAAAGACAGTAATAATGATAAAGGT

TCGTTAGTTAGTCGTCCAAATGTATACCGTGTGAATATAGGATTAAAAAAAGAAACTTTT

ATTGAAATGTTTGGATATATTCCAAAGCGTCCAGGTGTAGGTCAAATAGTTGATATGGAT

TTTGATTTTACAAAATTGGACACAATCATGCCACATCCTATCTACTCATGGATGGGATGG

ATATGCGTCCTAAGCCCTACTGAAAAGACATTTGAGAACTTTAAAACTTTAATAGGAGAA

TCTTACAATTTTGCAAAACAAAAATTTAAAAAGAGAAAAAACAAGTAA (coding nucleotide sequence of CD1543a)
SEQ ID NO: 24
ATGCGAGAAGAAAAAAGTAATGAAAAGTATGATTGTTATTGGTGTAATCAAGAGAATAAT

TTCTGTGTAGAAATAAAAGATAATATAGTCATGATAGATGATGGCACTGGTACGTTAAAA

CAAGCCGTTTTCATAGGGTATAAACAAATCCAAATTAATTTAAACTGTTCACATTGTCAA

AACTTAAATAGAATAAAATTAAATTTGTAG (coding nucleotide sequence of CD1794)
SEQ ID NO: 25
TTGTTTATAGATGAAGAATTAGAAGGTTATATATTAACATGTAAAATATCTGAAGACTTT

AAAAATATACCTGAATATAGTGATGAAGAGTTTTATGTTACAGTCTATAAAGATGAAAGT

TCTGACTCTGGGTACTATGCTTTATTAGAAAATAAAGAAGAAAGAGTTGTATGGGATGGA

-continued

GAAGTTGTTGCCAATAATATTTTTAATAACCTTTGGATTGTAGTAAATAAGGTTAAAACT

GGATAA (coding nucleotide sequence of CD1906)

SEQ ID NO: 26

TTGCATATGGAAATCAATGTTATAGAAATTTTCCCTAAAGATAAAGCTAAACTTAATAAA

ATAGAAATGGATAAAGCTAGTTGGTTTGTAAATATAATAAGTAAAAAATATCCTAAAGAA

GCTTTAAATGAAGCATTTAGTACTTTAGAAAAAGAATTAAATATAAGTAAAGCTAATACA

TAA (coding nucleotide sequence of CD2046)

SEQ ID NO: 27

GTGGATGAAATGCTTGTATATAATAAAAGTTTTTATCCTAATGACATATTTCCAAGATTA

GATTTTTCAAAAATAAAAAAACAGTTAAAATTGATAGATAATGACCTGTCAGATTTTGGA

AGCATATGTATAATAGAAAAGAACATTATACGATAAGTGTAAACAGTATAGGTGAAATA

AATGTGTACTATGATTTAGAGTACGAAAATAAGGTGTATAGAATAGTTTATGAGATTGAA

AAGTTATTTAAATCTCAAGTTGGAAGGTTTAGCATATCTACATACAGAAATTGA (coding nucleotide sequence of CD2098)

SEQ ID NO: 28

TTGGCTGGTAATCTAAATAATATGAGAGCAGTAAATAATTTTAGAGGAGATAAGAACATT

TTAGAATGTTTAGTCAGCTTTGAGGGTCGTTCAATAAGTCAGAGAAAAGTAAGGGTATTT

TTTAAAGAAAAACAAAATCAAATAGAAATTGATTTTGCAGAAGAGGAAATTTCTAAATTG

GTTGAAAATGTTGTTTTAAATACATCATATCAAGAAATGTTATATGATGAAATAGAGAAA

CAACTGGAAATTGATTGTATAGGTACTTGGATGATATTATCTAAATTAAAAGATGGTAGT

AGAGTTCACTGA (coding nucleotide sequence of CD2216)

SEQ ID NO: 29

ATGATTGTGATTGAAGGTAGCGATAAATTTAAGATTGCAAAAGAATATATTGATGTAGAA

TATACTCTTTTTAGCAAAGTAACTTTTAGGTATGAAAAGTTGAAATTTAAAGATAATGCT

GAATTGGAAAAAATTAAGATGTTTAAATATAAAAATGGCTACATCCCTAATAAATTAAAC

CTTTCTTTTGGATATGGATTCTCTTCTTATAAAAAGCAAATAATTAGAGAAACTGTAGAT

ACTTTAAGATTGACAGAAATTTTTTCAAGCGAGAACATAGAAGATATTAAATTTATAAAA

GATGGTACAAAAAAATTAGAAATTAGCATAGAGAAAGTTGTGAAATTTAAACGTCGAAAA

AAAAGAAATTATGTTTGTTGCTATTGCCCTGATATGTATAGGGACATAAAACTCGACAAA

GAATCTATCAATAAGATATACAACAGAAAAATAAAAATAGAAAGAGAAGTTAATATTTTT

GAAGATGAGGATGTTATAATAAACAAAAAAGTATTGAAGTTTCCAAAGTCTTGGACAAAG

AATATGCAAAAATATTGGTTAAGTGAAAATAAGTATCCCATACATTCTACTGTAATTGAT

GATGATAGATATAAATGTTGTAATGTACAATATACAAAAAATAGAGTGATAATATTTATAT

TACATATATAACCATTAA (coding nucleotide sequence of CD2264)

SEQ ID NO: 30

GTGTTAAAAAAGTGGTTTGGTATTGTGAAAAAAAGACAAAAAAGTGAGTCAGTAAAAGAA

GAAGGTGAAGTAATATTAAAAAACGAAAAAATATTATCTGAAGAAAAGTTGATAGATGAA

GAAGGAGTTGTAGTTAATATTGATAATGAAATATTAACTAAAGTAGAAGTAGTAAATGAT

GACAATGAAATAGAAGAAAAATAATAGAAGAAGATTGGTTAATTAGTGAAAATACCATA

AAATTAGATGATAAAGAAGCAATTATTAATGATAAAAACATAGAATTATGTAAAAAAGAA

GTTCAAGTTGAAGGTGAAAAAATAGATTTAAATAAGTTTGAAGGACTTGACCAAAATGAA

```
AATTATAATCTAGAAAAAAATGTTATTGAAGAAAAAGAAGTAAGTGAATGTTTGACAGAA

GAAGATTTAGAGTACATAAAAGAAATTAAAATAAAAAGAGGAAAAAGTATAAAAGCTATA

AACTTGTATACTAAAGAAGAGTGGGTTTTTGACACTCATATACAGTGTAGTAAAAAACTC

AAAGTTCCATTAGGGTACATAAGAGAAAATTTAAAATATGGATATATGGATTACTTTGGA

GATGCAATAAATTATTTAAGTGAAGTATTAAATATAGATGAATACTGCAAAAGTGAATGG

AGCTATCTCGATAATAGCAAATCTCCATCTGAGATATTTAATATTCTAAACAATAAAATA

TTTAGTATAAGGCTTTCTAATGAAAAAGAAATGAAATTTTGACAAATGATAAAATTGAA

GCATTAAAAATGAATTATAGATTTGAATGTATTGATGAAGAATATGATGAATATTTTAAA

AAATATAAGTCTATAATCAAAAGAGGTGGAAAGAAAAAAGTTGAATTAGTAAATAAAAAA

GGTGACATTTTAGAAATATTTAAGTCTTTAGAAGAATGTGCCATTTATTTGCAAAAGGAA

AAGAATGAAGTTATACAAATGTTAAAATATGGAGATACAAAAGTAGGAAGAAACTTTATA

AGGTATAGTTTGAGAAGTATTTAA (coding nucleotide sequence of CD2274)
                                                    SEQ ID NO: 31
ATGGATTTAAGTGGCATATTTAAATACTATTGTAAAGAGTGTGAAAATACATGGAATAAT

TCGAGTGTTGAATTATTTGAGAATATAGAAACGTATAGTAAAGATTCACAAAAAAAGAGG

GAAAAAGAATTAGATAAATTGCTAAATACAATATCAGTTCATTTAGAGAGGTATCCAAGT

GATGCTGTATTGAGAAAATGTGGGTAAAAAGGGCGAGGTTTTCTTACAAAAGACATTG

GAAAAAGAAATATTTTTAAGTTAGAAAAAATGGATGTAGAGGATAGAAAAAAATTTTTA

GATATAACAAAACAGTTTATTAGAGATGCTAGAAAATTTGATGATGATTTACCTATAGGT

GATATTATGCAAGCTATGAGGAATGTATGGATTTCAAATGCATTACAATTATTATTTGGT

AAAGAAGTATATTATTCAAAAGCTAACTTTGCATATAGTATGTTATATCCATATACTGAT

AATTATTTAGACAATACAAATATAGATAAAAATGATAAGATTTTATTTAATAACTGGTTA

GAAAAAAGGCTCCTGGGAGAACACATTAAATCTAAGGATTATCATGAAAGTAAAGTATCT

CAAATGATAGATTATATTGAAAGTGTATACCCTAGAGAAAAGTTTACAGAAGTTTATGAA

TCGTTATTATTAATATTTAAAAGTCAAGTAAATAGTTTAAAACAACATGGTAAGGAAAAT

CATTTGTGTAAAGAAGATTTATTATCCATTTCTATTGAAAAAGGAGGTTCATCCGTTTTA

GTAGATGGATATTTAATAAGTGGATTGATGACAAAGGAAGAAATAGAGTTTTGTATAGGA

TATGGATTTTTATTACAAATATCTGATGATTTACAAGATATAAAAGAAGATTTAAAATAC

AACCATAAAACTATTATTACAGAGATGTCAAAAGAGGGTACTTTAGATAAAGTTGTAAAT

AAACTAATAAATTTTACTATTGAGTTAATAGATAGTTTTAAAATTAATAATAAAAATAAA

TCTGTAATAACTATGATAAAGAATGATTGCTTAATGTTAATTTTATTTTCTGTAGTTTAT

AATGCTGAATTTTTTTCTGTAGGATATATAAAAGAAGTAGAGAAATTTATTCCATATACA

ATAGATTATTCATTAGAGATTGAAGAAAAAATAAAAGAAAAATTTAAAAATATAGATGTT

TTAAATAATGAAAATGAATATAAAGAAATGATTGATATTATTTGTGCAGAGTAG (coding nucleotide sequence of CD2309)
                                                    SEQ ID NO: 32
ATGTTTAGAGATAAAATGGATAAATGTACACATATGTTAACTGCTTATATTGGTAGTTCA

TATGATTATTGTGATTTTATAGATACACAGTTAGATGATTTTATATTAGAGTACGGAGAA

AAAGTTGTGGAATCTTGCTTGCATCAAGTGATGGTATTGGTAAGTAAGTATAATTAG (coding nucleotide sequence of CD3188)
                                                    SEQ ID NO: 33
ATGAGCAAAAGTGAATTAACAGCAGAAACAACAGAAGAAATGTTAGAAGTACTAAGTGGT

AAAGATTATGATATTGCATGTCATTTACATGAACTTGGTAAATCATTAGATTGTAAAATT
```

```
GAACCAAAAACAGGTGCTCGTTCTTACAAAATAGTATATTCAACTAAGAAACCAAAACGT

AGCTTATTTACTATTGAATGTAATGAAAAAAAATGGAGAGTTAAAGCAAATCTTTTTCAT

CTAAATACATATAAAGATGCTGTGGAGGAATGCTCTAAAACTATTAAAGATAGTATAACT

AAAACTCGTACTTGTAAGAAATGTAATTCAAAGTGTATTGGAGGTTCTTCGTTTGAATTA

GATGGAAAGTCTTACCTGACTTGCATAGGAAGTGGTCATTATTTTGCAAATATGGAAGAA

ATGGATTGGAAAAACCTAGAAAAATTAATTACTAAAGAAAATAATATTATGCAGGAATCT

GTATAG (coding nucleotide sequence of CD3288)
                                                    SEQ ID NO: 34
ATGGACTATATAGGAATAGAAAATATAACACCTTATGAAAATACATATGAATTTAGTGTA

TATGAATATGATGATGAAATCACCTTAGGTAGTGAAAAGTTATATGTATGTGAATTAAGG

GTTGTATTGATTAAAGTTAATTCTCTGTATGTTGAAAGATTGCATAAATCAGTTGAAGCA

ATGGTCTTAGTAAAAAATTTGAAAAAAGATTTAGATAAAACACTTGTTGTAAACAAAATA

AAGAATTTTGTGCTAGATGAGATTTGGGTAGAAAATCTAGTAAAAGAGAATATAGAAGTT

ATATTTGTAGAAAGCTAG (coding nucleotide sequence of CD3367)
                                                    SEQ ID NO: 35
ATGAAAATATCTAGTCAATATAGAAGTCAATATTCATTTAGATATGAAAGTAATATAAAT

AATACAAGAATAAATGAAAGTATGGTTAAGAAAAATGAAACTGTAGGAAAAGACACTTAT

TTATCTAATATTATGAAACAAAAGCAAGAACTTAATGATAGAATTAGAGATTTAAAATAT

AGACAAGAGGTTTATACTAAAAAAATAAATGACGCAATTAAGAACTTATGTAAATCAGAA

ATAAGAGAAACAACTAATAATTTTTCTAATATAGAAATAGGTATTAAAAATAGCATTATA

GAAGAGAAAATAAAAGTACAATGTTAGATGAAAATTCAACTTATCTAAATACAAATGAT

GAAAAAGAATCTTTAATCACTAAAGAGTCTAATGAAAAAATTGAAGAAGAAATATTTAAT

GATGAAAAATTAGAAGAGTTAGAACAAAAAAAGGATTATAAAGAGGATTCTAATAAAAAA

GAGAAAGTATCTGAGGACTTATCTTTAGTAGGTAAAACTCGTGAAGAGCTTGAAAATATG

CTTAAAAATTTTATAAATTTAACACAAGAAGAAATAATGAAACTTGAGTCGAGAATAGAA

AAGTTAGATAAAAATGCTGAAGAATACAAACAAAATTCAAAGACTAATATATTTGATAAA

ACAGATGAACAAAAAAAACATATAAATGTACTGATTTAA (coding nucleotide sequence of CD3609)
                                                    SEQ ID NO: 36
ATGTTTAAGAAAATGGCAGTACTAAAAGATATAGCAACTAAAATAGGTCGTAAAAAAGCG

TATGAACTATTAGAAATGGTTGAAGGTAATGATGCCTTTGTAGCTGAGGTAAAGATAAAA

AAGAATGGAATAGAATCTAAAAAAGAAGAAATTATGTTAAAAGATAATCAAAAAATAATA

TTAGAGTATATAGAAGGTTAA (forward primer directed to SEQ ID NO: 21)
                                                    SEQ ID NO: 37
TGTTTATTTTGAATTTTGGAGGATT (reverse primer directed to SEQ ID NO: 21)
                                                    SEQ ID NO: 38
CATGAAAAATAGCCCATGGAA (forward primer directed to SEQ ID NO: 22)
                                                    SEQ ID NO: 39
AGATGAAATGGATAAATGTACACACA (reverse primer directed to SEQ ID NO: 22)
                                                    SEQ ID NO: 40
CCATCACTTGATGTAAACAAGATTC
```

-continued

| | |
|---|---|
| (forward primer directed to SEQ ID NO: 23) GGGGGAACGAGCAATTTACTA | SEQ ID NO: 41 |
| (reverse primer directed to SEQ ID NO: 23) ACCTACACCTGGACGCTTTG | SEQ ID NO: 42 |
| (forward primer directed to SEQ ID NO: 24) TGATTGTTATTGGTGTAATCAAGAGAA | SEQ ID NO: 43 |
| (reverse primer directed to SEQ ID NO: 24) ACCCTATGAAAACGGCTTGTT | SEQ ID NO: 44 |
| (forward primer directed to SEQ ID NO: 25) ATAAAGATGAAAGTTCTGACTCTGG | SEQ ID NO: 45 |
| (reverse primer directed to SEQ ID NO: 25) TTAACCTTATTTACTACAATCCAAAGG | SEQ ID NO: 46 |
| (forward primer directed to SEQ ID NO: 26) TGCATATGGAAATCAATGTTATAGAAA | SEQ ID NO: 47 |
| (reverse primer directed to SEQ ID NO: 26) TGCTTCATTTAAAGCTTCTTTAGGATA | SEQ ID NO: 48 |
| (forward primer directed to SEQ ID NO: 27) ACCTGTCAGATTTTGGAAGCA | SEQ ID NO: 49 |
| (reverse primer directed to SEQ ID NO: 27) TGCTAAACCTTCCAACTTGAGAT | SEQ ID NO: 50 |
| (forward primer directed to SEQ ID NO: 28) GTCAGCTTTGAGGGTCGTTC | SEQ ID NO: 51 |
| (reverse primer directed to SEQ ID NO: 28) ACAATCAATTTCCAGTTGTTTCTCT | SEQ ID NO: 52 |
| (forward primer directed to SEQ ID NO: 29) CCTTTCTTTTGGATATGGATTCTC | SEQ ID NO: 53 |
| (reverse primer directed to SEQ ID NO: 29) CAGGGCAATAGCAACAAACA | SEQ ID NO: 54 |
| (forward primer directed to SEQ ID NO: 30) AAGAGTGGGTTTTTGACACTCA | SEQ ID NO: 55 |
| (reverse primer directed to SEQ ID NO: 30) AGCTCCATTCACTTTTGCAGT | SEQ ID NO: 56 |
| (forward primer directed to SEQ ID NO: 31) AAAAAGGCTCCTGGGAGAAC | SEQ ID NO: 57 |
| (reverse primer directed to SEQ ID NO: 31) CGGATGAACCTCCTTTTTCA | SEQ ID NO: 58 |
| (forward primer directed to SEQ ID NO: 32) GGATAAATGTACACATATGTTAACTGC | SEQ ID NO: 59 |
| (reverse primer directed to SEQ ID NO: 32) GCAAGCAAGATTCCACAACT | SEQ ID NO: 60 |

(forward primer directed to SEQ ID NO: 33)

ACCAAAAACAGGTGCTCGTT                              SEQ ID NO: 61

(reverse primer directed to SEQ ID NO: 33)

AGAGCATTCCTCCACAGCAT                              SEQ ID NO: 62

(forward primer directed to SEQ ID NO: 34)

TGATGAAATCACCTTAGGTAGTGAA                         SEQ ID NO: 63

(reverse primer directed to SEQ ID NO: 34)

CCCAAATCTCATCTAGCACAAA                            SEQ ID NO: 64

(forward primer directed to SEQ ID NO: 35)

AAAACTCGTGAAGAGCTTGAAAA                           SEQ ID NO: 65

(reverse primer directed to SEQ ID NO: 35)

TGAATTTTGTTTGTATTCTTCAGCA                         SEQ ID NO: 66

(forward primer directed to SEQ ID NO: 36)

AAAATGGCAGTACTAAAAGATATAGCA                       SEQ ID NO: 67

(reverse primer directed to SEQ ID NO: 36)

CCTCAGCTACAAAGGCATCA                              SEQ ID NO: 68

The invention will now be further described in the following non-limiting Examples with reference to the following drawings in which:

FIG. 1 shows the layout of *Clostridium difficile* genomic templates on an LC480 plate. 1-41—clinical *C. difficile* isolates; 630 —*C. difficile* 630 (positive control); *E. coli*—*Escherichia coli*; Staph—*Staphylococus epidermidis*; −ve—no template negative control.

Figure 2A:
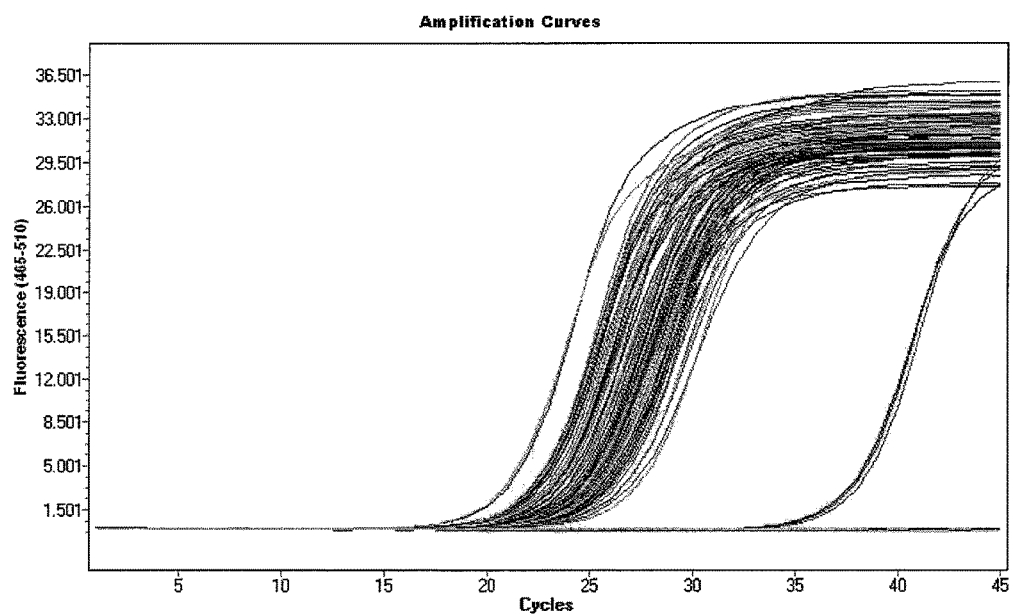
FIG. 2A is an amplification graph of the real-time PCR reaction for the CD2961 gene.
Figure 2B:
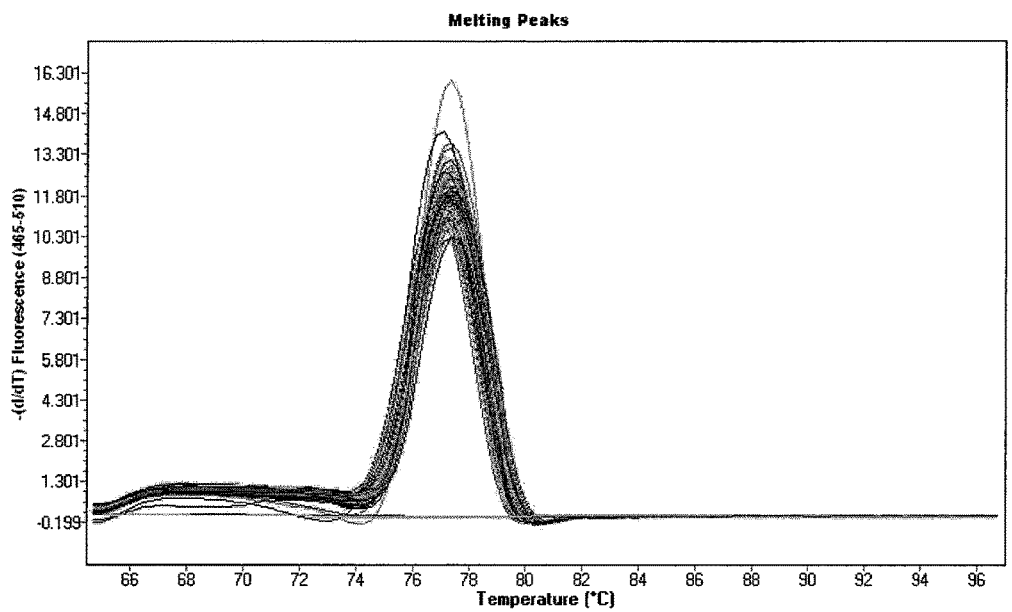
FIG. 2B is a melting curve of the real-time PCR reaction for the CD2961 gene.
Figure 2C:
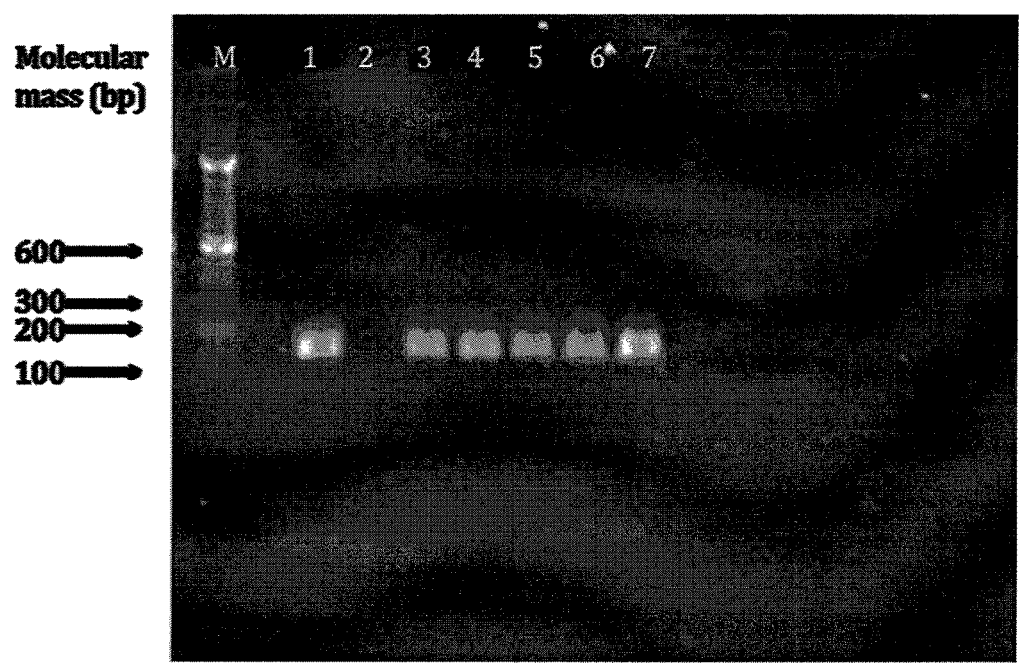

FIG. 2C is a gel photograph showing real-time PCR products from the CD2961 plate. Lane M: 100 bp molecular mass ladder; Lane 1, positive control; Lane 2, blank, Lanes 3-7: clinical isolates.

EXAMPLES

Example 1

Introduction

Using an in silico comparative genomics approach the presence of proteins that are unique to *Clostridium difficile* have been identified. 53 genes annotated as encoding "hypothetical proteins"—i.e. those whose biological function has yet to be experimentally verified—in both *C. difficile* strain 630 and *C. difficile* strain qcd32_g58 (a hypervirulent strain which produces higher levels of toxins) are absent from all other *Clostridium* species and related organisms whose genome sequences are available at the Clostridb database (http://xbase.bham.ac.uk/clostridb/). Crucially, no significant matches to any other gene products were found when a BlastP search was made of the NCBI non redundant sequence database. This led the inventors to hypothesise that some of these 53 genes (and DNA molecules, RNA molecules or polypeptides derived therefrom) would be potential biomarkers unique to, and therefore likely to be extremely specific for, *C. difficile*.

In this investigation, PCR primer sets were designed against 52 potential biomarker genes. These 52 genes are CD0588, CD0589, CD0590, CD0638, CD1124, CD1234, CD1423, CD1424, CD1487, CD1543a, CD1581, CD1586, CD1597, CD1613, CD1728, CD1757, CD1794, CD1897, CD1906, CD2046, CD2098, CD2133, CD2216, CD2248, CD2264, CD2274, CD2300, CD2306, CD2309, CD2454, CD2547, CD2563, CD2815, CD2961, CD2972, CD3022, CD3023, CD3024, CD3163, CD3188, CD3288, CD3321, CD3367, CD3369, CD3573, CD3609, CD3617, CD3618, CD3635, CD3638, CD3641, and CD3656.

The ability of these primer sets to direct primer directed amplification was assessed by carrying out PCR reactions on the genomic DNA of *C. difficile* strain 630. Some of these primer sets were then used to screen 41 clinical *C. difficile* isolates for the presence of the relevant biomarker (gene of interest).

Materials and Methods

Reagents:

All chemicals and reagents used were of Analar grade or better. Brain Heart Infusion (BHI) agar was purchased from Oxoid, UK. All reagents necessary for standard PCR master mix and 100 base pair ladder were purchased from Invitrogen, UK; Agarose QA was from Qbiogene. All reagents necessary for qPCR were purchased from Roche Diagnostics, UK. All apparatus was sterilised and cleaned with Virkon (Antec Intl Ltd., UK) and soaked in 2% Decon (Decon Labs Ltd., UK) overnight before use.

Growth of Bacterial Strains:

*Clostridium difficile* strain 630 was obtained from Dr Peter Mullany of the Eastman Dental Institute, London. A further 41 *Clostridium difficile* strains were obtained from Dr Derek Fairley of the Northern Ireland Ribotyping Network, based in the Bacteriology department of The Royal Victoria Hospital (RVH), Belfast. All strains were routinely grown on Brain Heart Infusion (BHI) agar plates within a Don Whitely MG500 anaerobic cabinet (Don Whitely Scientific Ltd, Yorkshire, UK), in addition to being kept frozen on cryobeads at −70° C. The anaerobic conditions within the cabinet were 80% $N_2$, 10% $CO_2$ and 10% $H_2$ at 37° C. The agar plates were incubated for 48 h to allow growth of the organisms. Resazurin (1 mg/L) was used as an anaerobic indicator and was added to the BHI agar prior to autoclaving. *Escherichia coli* and *Staphylococcus epidermidis* were used as negative controls in this study; they were grown on nutrient agar plates at 37° C. under aerobic conditions.

DNA Extraction:

DNA was extracted using the Fast DNA Spin Kit for Soil (MP Biomedicals, USA) from a loop of bacterial biomass, according to the manufacturer's instructions. The extracted DNA was then quantified using a Nanodrop™ 1000 Spectrophotometer (Thermo Fisher Scientific, Wilmington, USA). For qPCR the extracted DNA was diluted to 1 ng/µl and stored at −70° C. until needed. Prior to use, genomic DNA was diluted four-fold to enable the addition of 4 µA template to each reaction well.

Primer Design and Validation:

The primers used in this study were designed using the OligoPerfect™ tool (Invitrogen, UK). The forward and reverse primers were designed against *C. difficile* gene sequences downloaded from NCBI. A total of 52 primer sets were ordered from Invitrogen, UK, i.e. a primer set was designed for each of the potential *Clostridium difficile* biomarker genes. The primers were then validated by standard endpoint PCR using *Clostridium difficile* 630 genomic DNA as template in a TGradient Thermocycler (Whatman Biometra, Goetigen, Germany). The PCR master mix (96.5 µl) was made up of PCR buffer, $MgCl_2$, dNTPs and millipore water as per the kit instructions; to this 2.5U Taq polymerase, 1 µl forward and reverse primers and 1 µk genomic DNA template was added to make up a 100 µl PCR reaction. The PCR cycling conditions used were as follows: an initial denaturation stage for 5 minutes at 95° C. followed by 30 cycles of 95° C. for 30 s, an annealing stage at a range of temperatures between 54° C.-58° C. (depending on primers) for 30 s and extension at 72° C. for 30 s; with a final extension at 72° C. for 5 minutes. The thermocycler then held the temperature at 4° C. The PCR products were then mixed with 6× loading dye (Invitrogen) and visualised by gel electrophoresis/UV transillluminator on a 1% TBE agarose gel containing 4 µg ethidium bromide/100 ml gel (Sigma-Aldrich, UK) to determine band size in comparison to 100 bp markers (Invitrogen), and the image was recorded using Alpha-Imager 2200 software (Mason Technologies, Dublin, Ireland).

Quantitative PCR:

All quantitative PCR (qPCR) was carried out using the LightCycler480 (Roche Diagnostics, UK), following the manufacturer's instructions for cycling conditions and preparation of mastermix. A mix of Master SYBR Green 1 (Roche Diagnostics, UK) and the primers specific to that plate was prepared and 6 µl of this was added to 90 of the 96 wells and to this 4 µl of the appropriate DNA was added to the well. FIG. 1 shows the order in which the genomic DNA templates were added to the LC480 plate.

The cycling conditions used for the qPCR were: an initial denaturation stage of 95° C. for 5 minutes followed by 40 cycles of 95° C. for 10 seconds, annealing at 55° C.-60° C. (depending on primers) for 10 seconds and extension at 72° C. for between 10-20 seconds (dependent upon expected product size). Once the amplification programme had finished, a melting curve analysis was performed to determine if one or multiple products had been produced. Data was stored in the form of a printable pdf file generated by the LC480 instrument and contained all relevant details including crossing point in the amplification step and melting profile for the amplicons produced from each template. This allowed screening of a given gene against 41 *Clostridium difficile* genomes at once in a single lightcycler 480 run, thus aiding throughput.

Gel Electrophoresis of qPCR Products:

As a confirmatory step, a number of samples from each plate, including the positive and negative controls were electrophoresed on a 1.5% TBE/agarose gel as described above.

Results

Primer Design and Validation.

The genome of *Clostridium difficile* 630 was downloaded from the NCBI website; from this, a total of 683 genes annotated as "conserved hypothetical protein" were identified. A BlastP search was then performed using the ClostriDB website to determine which of these 683 conserved hypothetical proteins were unique to *C. difficile*. A total of 53 of these "hypothetical" proteins were identified as being unique to *C. difficile*.

Primers were subsequently designed to amplify 100-500 bp amplicons from 52 of these genes as per the Materials and Methods section of this example. Validation of the primers was by endpoint PCR using *C. difficile* 630 DNA. In the present study, PCR reactions were performed using 24 of the 52 primer sets and these 24 primer sets produced clear bands (amplicons) of the expected size on agarose gels following electrophoresis. These 24 genes and their associated primer sequences are identified in Table 1.

Clinical Isolates.

42 clinical isolates of *C. difficile*, of varying ribotypes, including 106, 078, 020, 001, 005, 026 and 014, were obtained from The Royal Victoria Hospital (RVH), Belfast under the terms of a material transfer agreement between UUTech and the RVH. The strains were sub-cultured on BHI agar plates in an anaerobic cabinet at 37° C.; one strain (clinical isolate) failed to grow, thus genomic DNA was extracted from 41 strains (clinical isolates). These 41 strains (clinical isolates) are listed in Table 2). The strains were also transferred onto cryobeads (TSC Ltd, UK) and archived at −70° C. for future reference. The extracted DNA was diluted to 1 ng/µl for real-time PCR use and stored in aliquots at −70° C.

Lightcycler 480 qPCR

Real-time (quantitative) PCR (qPCR) was performed using the Lightcycler480 instrument (Roche Diagnostics, UK). A 96 well plate was used to carry out the PCR with 90 of the wells containing master mix with the specific primers for the gene of interest; the template genomic DNA samples were then added to the appropriate well in a specific order (as per FIG. 1), with each DNA sample on the plate being analysed in duplicate. Laboratory strains of *Escherichia coli* and *Staphylococcus epidermidis* were used as negative controls. Each plate was run on the Lightcyler480 with cycling conditions specific to the primers i.e. with an annealing temperature and an extension time specific to the primer set being used. Results were obtained in the form of amplification graphs and melting curves (see FIGS. 2A and 2B for representative examples for the gene CD2961). If a crossing point of greater than 40 was recorded in the analysis the result was left as a question mark (?) in the data Table (Table 3) instead of a definite negative result as the late crossing point may have been due to other factors such as primer specificity, template variability, or not enough cycles. Agarose gel electrophoresis, to check for bands (amplicons) of expected size, was used as an extra confirmatory step to enhance the accuracy of the results obtained (see FIG. 2C for a representative example for the gene CD2961).

From Table 3 it is evident that five of the genes of interest (CD2961, CD3617, CD3618, CD3635 and CD3638) yielded amplicons of the expected sizes from all the *C. difficile* genomic DNA templates tested.

SUMMARY

In summary, 53 genes annotated as encoding "hypothetical proteins" that are unique to *Clostridium difficile* have been identified. It has been demonstrated CD2961, CD3617, CD3618, CD3635 and CD3638 are detectable in 41 clinical *C. difficile* isolates of varying ribotypes.

TABLE 1

24 conserved hypothetical protein encoding genes and their associated primer sequences. Whether or not a primer set could direct amplification of the target gene was determined by endpoint PCR using C. difficile 630 genomic DNA template. The presence of a "Y" in the "Amplicon" column indicates that a clear band (amplicon) of the expected size was visualised on an agarose gel following electrophoresis of the PCR product.

| Gene No. | CD No. (Gene) | CD630 | CD-QCD-32g58 | fwd primer | rev primer | Annealing temperature (° C.) | Amplicon Size (bp) | Amplicon |
|---|---|---|---|---|---|---|---|---|
| 2 | CD0589 | √ | √ (97%) | TGGAAGAGCGGAGAACTTG (SEQ ID NO: 69) | GATAGCCACCACTTCCTCCA (SEQ ID NO: 70) | 57 | 470 | Y |
| 3 | CD0590 | √ | √ (97%) | GGTGAAATGGACAAGATGG (SEQ ID NO: 71) | TCTCCATCATCTGCTGCTTG (SEQ ID NO: 72) | 57 | 476 | Y |
| 5 | CD1124 | √ | √ (99%) | TCTGTGGCCAAAGAAAACA (SEQ ID NO: 73) | CCACAATTAAATCAAAATGTCT (SEQ ID NO: 74) | 57 | 500 | Y |
| 11 | CD1581 | √ | √ (95%) | TCAGAAGATTGGTATGAAAGAGAA (SEQ ID NO: 75) | TGGCATTTATGGCAACAATTA (SEQ ID NO: 76) | 57 | 431 | Y |
| 12 | CD1586 | √ | √ (98%) | TTTTGAGTTTTATTGCCCAAAT (SEQ ID NO: 77) | GGTAAACCAGCTGGAGCTTT (SEQ ID NO: 78) | 57 | 531 | Y |
| 13 | CD1597 | √ | √ (98%) | ATGGAGTGGCGAAACAAAAC (SEQ ID NO: 79) | GCATGTGCAGTTTCATGTAATTCT (SEQ ID NO: 80) | 57 | 513 | Y |
| 14 | CD1613 | √ | √ (100%) | GGTATAGAGATCTTTCAGCTCCTCCA (SEQ ID NO: 81) | CAACAGCAATCATCACAATCG (SEQ ID NO: 82) | 57 | 452 | Y |
| 16 | CD1757 | √ | √ (100%) | TGGCATAAGGATTTAATTGATGT (SEQ ID NO: 83) | AAACATGATATTCCAGACCACAA (SEQ ID NO: 84) | 57 | 450 | Y |
| 22 | CD2133 | √ | √ (98%) | ACTATATGGAATTTGAAGATATTCCTG (SEQ ID NO: 85) | TTTGATTGTTCTCTTATTCAACTGC (SEQ ID NO: 86) | 54 | 397 | V faint |
| 30 | CD2454 | √ | √ (98%) | TGGTTTTTGCATATACGAATGA (SEQ ID NO: 87) | CCTCCCTTCCATCATCACAATCC (SEQ ID NO: 88) | 58 | 453 | Y |
| 31 | CD2547 | √ | √ (98%) | GGGCAGGGCAAAGTTGTTAT (SEQ ID NO: 89) | TTTTGGTCGTGAGTTGCTGA (SEQ ID NO: 90) | 58 | 478 | Y |
| 33 | CD2815 | √ | √ (98%) | GCATGCAAACATTTTGGTGA (SEQ ID NO: 91) | TTCAGATACCTTGTCATCATGGA (SEQ ID NO: 92) | 58 | 438 | Y |
| 34 | CD2961 | √ | √ (99%) | AGAAGGCAGTCACCGACAGT (SEQ ID NO: 11) | CCTTTCCAATAACCGCTTCA (SEQ ID NO: 12) | 58 | 129 | Y |
| 35 | CD2972 | √ | √ (99%) | CCTAGATGAAAGACCAATTTTAGATGA (SEQ ID NO: 93) | CAGAGTCACAATTTCCACAACAG (SEQ ID NO: 94) | 58 | 413 | Y |
| 36 | CD3022 | √ | √ (97%) | ATCTTGTGGGCTGGGTATTG (SEQ ID NO: 95) | CCTCCTCCATGTACCGATTT (SEQ ID NO: 96) | 58 | 540 | Y |
| 37 | CD3023 | √ | √ (96%) | CCTCCAACAGATGGAAAACC (SEQ ID NO: 97) | GTACTGCCCACACCTTGTGA (SEQ ID NO: 98) | 58 | 456 | Y |
| 38 | CD3024 | √ | √ (95%) | CAACCAATCATAGGAACAACCA (SEQ ID NO: 99) | TCCACAATATCCACATTGGTC (SEQ ID NO: 100) | 58 | 480 | Y |
| 39 | CD3163 | √ | √ (97%) | TGGGGATGATAGGATGTTATACTAAA (SEQ ID NO: 101) | TCCATCATCAGATGCTTCTTGTA (SEQ ID NO: 102) | 58 | 464 | Y |
| 45 | CD3573 | √ | √ (98%) | TGGATATAAGAGCGTTACCTATAAGA (SEQ ID NO: 103) | TCAACTCCACCTTTCCAAAAA (SEQ ID NO: 104) | 57 | 474 | Y |
| 47 | CD3617 | √ | √ (99%) | GATGGATACTGGGGTGATGG (SEQ ID NO: 13) | AAGGCAATAAAGTCGCTTCG (SEQ ID NO: 14) | 57 | 475 | Y |
| 48 | CD3618 | √ | √ (99%) | TTTAATGGTACTTGTGAAAAAGCAT (SEQ ID NO: 15) | GCCATCATTTTGATGTGGTG (SEQ ID NO: 16) | 57 | 306 | Y |

TABLE 1-continued 24 conserved hypothetical protein encoding genes and their associated primer sequences. Whether or not a primer set could direct amplification of the target gene was determined by endpoint PCR using C. difficile 630 genomic DNA template. The presence of a "Y" in the "Amplicon" column indicates that a clear band (amplicon) of the expected size was visualised on an agarose gel following electrophoresis of the PCR product.

| Gene No. | CD No. (Gene) | CD630 | CD-QCD-32g58 | fwd primer | rev primer | Annealing temperature (° C.) | Amplicon Size (bp) | Amplicon |
|---|---|---|---|---|---|---|---|---|
| 49 | CD3635 | √ | √ (95%) | CATATGCCTGAGATGGCAAA (SEQ ID NO: 17) | CTTGTGCCCATTCTGGTTTT (SEQ ID NO: 18) | 57 | 499 | Y |
| 50 | CD3638 | √ | √ (99%) | GGATGCTGTTTTGGAGGAAA (SEQ ID NO: 19) | AAATTCTGGGCAATGAGGTG (SEQ ID NO: 20) | 57 | 525 | Y |
| 51 | CD3641 | √ | √ (98%) | CTTGTGACGGGCATGTATTG (SEQ ID NO: 105) | TGTTTTAAGCCCTCCCATTG (SEQ ID NO: 106) | 57 | 419 | Y |

TABLE 2

List of *Clostridium difficile* strains obtained from Royal Victoria Hospital

| | RVH ref No | Ribotype |
|---|---|---|
| 1. | 100058-106 | 106 |
| 2. | 100048-106 | 106 |
| 3. | 090092-106 | 106 |
| 4. | 100059-106 | 106 |
| 5. | 100150-078 | 078 |
| 6. | 090126-106 | 106 |
| 7. | 090269-106 | 106 |
| 8. | 100149-078 | 078 |
| 9. | 090160-106 | 106 |
| 10. | 100162-020 | 020 |
| 11. | 090389-106 | 106 |
| 12. | 090361-106 | 106 |
| 13. | 090183-106 | 106 |
| 14. | 090391-106 | 106 |
| 15. | 090129-106 | 106 |
| 16. | 090217-106 | 106 |
| 17. | 090225-106 | 106 |
| 18. | 090223-106 | 106 |
| 19. | 090645-106 | 106 |
| 20. | 090294-106 | 106 |
| 21. | 090540-106 | 106 |
| 22. | 100063-106 | 106 |
| 23. | 100158-078 | 078 |
| 24. | 100170-001 | 001 |
| 25. | 100171-001 | 001 |
| 26. | 100172-020 | 020 |
| 27. | 100173-078v | 078v |
| 28. | 100177-005 | 005 |
| 29. | 100163-026 | 026 |
| 30. | 100178-106 | 106 |
| 31. | 100164-014 | 014 |
| 32. | 100167-001 | 001 |
| 33. | 100168-001 | 001 |
| 34. | 100169-078 | 078 |
| 35. | 100143-026 | 026 |
| 36. | 100144-014 | 014 |
| 37. | 100146-005 | 005 |
| 38. | 100147-014 | 014 |
| 39. | 100142-005 | 005 |
| 40. | 100140ii-020 | 020 |
| 41. | 100153-001 | 001 |

TABLE 3

(shown overleaf) - qPCR screening of CD2961, CD3617, CD3618, CD3635 and CD3638 across 41 strains of *C. difficile*, with *E. coli* and *Staphylococcus aureus* as negative controls and *C. difficile* strain 630 as a positive control. For all of the qPCR reactions for genes CD3617, CD3618, CD3635 and CD3638 and some of the PCR reactions for gene CD2961, the PCR product produced by the qPCR reaction was subjected to agarose gel electrophoresis to further assess whether an amplicon of the expected size was produced. In all cases in which the template DNA was *C. difficile* genome, bands of the expected size were observed (as shown by a "G+" in the "GEL" column). Note that no amplification from the *E. coli* or *Staphylococcus epidermidis* samples was observed.

| Strain/gene | CD2961 qPCR | CD2961 GEL | CD3617 qPCR | CD3617 GEL | CD3618 qPCR | CD3618 GEL | CD3635 qPCR | CD3635 GEL | CD3638 qPCR | CD3638 GEL |
|---|---|---|---|---|---|---|---|---|---|---|
| 1-106 | YY | | ?? | G+ | Y? | G+ | ?? | G+ | ?? | G+ |
| 2-106 | YY | G+ | ?? | G+ | ?Y | G+ | Y? | G+ | ?? | G+ |
| 3-106 | YY | | ?? | G+ | ?Y | G+ | Y? | G+ | ?N | G+ |
| 4-106 | YY | | YY | G+ | YY | G+ | ?? | G+ | ?? | G+ |
| 5-078 | YY | | ?? | G+ | YY | G+ | ?? | G+ | ?? | G+ |
| 6-106 | YY | | ?? | G+ | YY | G+ | ?? | G+ | ?N | G+ |
| 7-106 | YY | | Y? | G+ | Y? | G+ | YY | G+ | ?? | G+ |
| 8-078 | YY | | YY | G+ | YY | G+ | ?? | G+ | N? | G+ |
| 9-106 | YY | | ?? | G+ | ?Y | G+ | ?? | G+ | ?? | G+ |
| 10-020 | YY | | ?? | G+ | YY | G+ | Y? | G+ | ?? | G+ |
| 11-106 | YY | | ?? | G+ | YY | G+ | YY | G+ | ?? | G+ |
| 12-106 | YY | | ?Y | G+ | YY | G+ | ?Y | G+ | ?N | G+ |
| 13-106 | YY | | Y? | G+ | YY | G+ | YY | G+ | ?? | G+ |
| 14-106 | YY | | YY | G+ | YY | G+ | Y? | G+ | N? | G+ |
| 15-106 | YY | | ?? | G+ | YY | G+ | YY | G+ | ?? | G+ |
| 16-106 | YY | | ?? | G+ | YY | G+ | YY | G+ | ?? | G+ |
| 17-106 | YY | G+ | ?Y | G+ | YY | G+ | YY | G+ | ?? | G+ |
| 18-106 | YY | | ?? | G+ | Y? | G+ | ?? | G+ | N? | G+ |
| 19-106 | YY | | ?Y | G+ | YY | G+ | ?? | G+ | ?? | G+ |
| 20-106 | YY | | ?? | G+ | ?Y | G+ | ?? | G+ | ?? | G+ |
| 21-106 | YY | | ?Y | G+ | YY | G+ | ?? | G+ | ?? | G+ |
| 22-106 | YY | | ?? | G+ | YY | G+ | YY | G+ | ?? | G+ |
| 23-078 | YY | | YY | G+ | YY | G+ | ?? | G+ | ?? | G+ |
| 24-001 | YY | | ?? | G+ | YY | G+ | Y? | G+ | ?? | G+ |
| 25-001 | YY | | YY | G+ | Y? | G+ | YY | G+ | ?? | G+ |
| 26-020 | YY | | ?Y | G+ | YY | G+ | YN | G+ | ?? | G+ |
| 27-078v | YY | | YY | G+ | YY | G+ | ?? | G+ | ?Y | G+ |
| 28-005 | YY | | ?? | G+ | YY | G+ | YY | G+ | ?? | G+ |
| 29-026 | YY | | ?Y | G+ | YY | G+ | YY | G+ | ?? | G+ |
| 30-106 | YY | | ?? | G+ | YY | G+ | YY | G+ | ?? | G+ |
| 31-014 | YY | G+ | YY | G+ | YY | G+ | YY | G+ | ?? | G+ |
| 32-001 | YY | | YY | G+ | YY | G+ | Y? | G+ | ?? | G+ |
| 33-001 | YY | | YY | G+ | YY | G+ | YY | G+ | ?Y | G+ |
| 34-078 | YY | | YY | G+ | YY | G+ | ?? | G+ | ?? | G+ |

TABLE 3-continued (shown overleaf) - qPCR screening of CD2961, CD3617, CD3618, CD3635 and CD3638 across 41 strains of *C. difficile*, with *E. coli* and *Staphylococcus aureus* as negative controls and *C. difficile* strain 630 as a positive control. For all of the qPCR reactions for genes CD3617, CD3618, CD3635 and CD3638 and some of the PCR reactions for gene CD2961, the PCR product produced by the qPCR reaction was subjected to agarose gel electrophoresis to further assess whether an amplicon of the expected size was produced. In all cases in which the template DNA was *C. difficile* genome, bands of the expected size were observed (as shown by a "G+" in the "GEL" column). Note that no amplification from the *E. coli* or *Staphylococcus epidermidis* samples was observed.

| Strain/gene | CD2961 | | CD3617 | | CD3618 | | CD3635 | | CD3638 | |
|---|---|---|---|---|---|---|---|---|---|---|
|  | qPCR | GEL | qPCR | GEL | qPCR | GEL | qPCR | GEL | qPCR | GEL |
| 35-026 | YY |  | YY | G+ | YY | G+ | YY | G+ | ?? | G+ |
| 36-014 | YY |  | YY | G+ | YY | G+ | YY | G+ | ?? | G+ |
| 37-005 | YY |  | Y? | G+ | YY | G+ | YY | G+ | ?? | G+ |
| 38-014 | YY |  | ?Y | G+ | YY | G+ | YY | G+ | ?? | G+ |
| 39-005 | YY |  | YY | G+ | YY | G+ | YY | G+ | ?? | G+ |
| 40-020 | YY |  | YY | G+ | YY | G+ | YY | G+ | ?? | G+ |
| 41-001 | YY |  | YY | G+ | YY | G+ | YY | G+ | ?? | G+ |
| 630 | YY | G+ | YY | G+ | YY | G+ | YY | G+ | YY | G+ |
| *E. coli* | NN |  | NN | G− | NN | G− | NN | G− | NN | G− |
| *Staph* | NN |  | NN | G− | NN | G− | NN | G− | NN | G− |

Example 2 (Prophetic Example)

The methods of Example 1 are performed with primer pairs designed to target each of genes CD0588, CD0638, CD1234, CD1423, CD1424, CD1487, CD1543a, CD1728, CD1794, CD1897, CD1906, CD2046, CD2098, CD2216, CD2248, CD2264, CD2274, CD2300, CD2306, CD2309, CD2563, CD3188, CD3288, CD3321, CD3367, CD3369, CD3609 and CD3656. Primers for each gene are described in Table 4.

TABLE 4

Nucleotide sequences of primers directed to the genes listed in Example 2

| CD No. | fwd primer | rev primer |
|---|---|---|
| CD0588 | AGGTTGAAAATAGTAGAAAAGAAGATG (SEQ ID NO: 107) | TGGCTTAAACATTATACTACCATGA (SEQ ID NO: 108) |
| CD0638 | TGTTTATTTTGAATTTTGGAGGA (SEQ ID NO: 109) | CATATATCCAACTCATTAAGCCATGA (SEQ ID NO: 110) |
| CD1234 | TTCATATTTTATAACAAGGGGTGATG (SEQ ID NO: 111) | TTCTACTGTCTCAACTTTCTTCATAGC (SEQ ID NO: 112) |
| CD1423 | TGAAATGTTCTAATTGTGGAAGTGT (SEQ ID NO: 113) | TTCTTATCTTTACACCAATTCCTATCA (SEQ ID NO: 114) |
| CD1424 | GATGAAATGGATAAATGTACACACA (SEQ ID NO: 115) | CCAATACCATCACTTGATGTAAAC (SEQ ID NO: 116) |
| CD1487 | TGGAAAATGATACTATTAAGGCTGA (SEQ ID NO: 117) | TTGCAAAATTGTAAGATTCTCCT (SEQ ID NO: 118) |
| CD1543a | AATGAAAAGTATGATTGTTATTGGTG (SEQ ID NO: 119) | TTAATTTGGATTTGTTTATACCCTATG (SEQ ID NO: 120) |
| CD1728 | AAAATTACACCCTTAGAGGCACA (SEQ ID NO: 121) | TTACTCTTTTAAGTAAATTTCCACCTG (SEQ ID NO: 122) |
| CD1794 | AAGATGAAAGTTCTGACTCTGGGTA (SEQ ID NO: 123) | ACCTTATTTACTACAATCCAAAGGTT (SEQ ID NO: 124) |
| CD1897 | TCAGGTTGTGGATTATTTTGGA (SEQ ID NO: 125) | TGGTAATATTCCTCTTTATCATTTGAA (SEQ ID NO: 126) |
| CD1906 | TGCATATGGAAATCAATGTTATAGAAA (SEQ ID NO: 127) | TTTACAAACCAACTAGCTTTATCCA (SEQ ID NO: 128) |
| CD2046 | TTTTTATCCTAATGACATATTTCCAA (SEQ ID NO: 129) | AGATATGCTAAACCTTCCAACTTGA (SEQ ID NO: 130) |
| CD2098 | GGCTGGTAATCTAAATAATATGAGAGC (SEQ ID NO: 131) | CCAAGTACCTATACAATCAATTTCCA (SEQ ID NO: 132) |
| CD2216 | TTGTGATTGAAGGTAGCGATAAA (SEQ ID NO: 133) | TCCAAGACTTTGGAAACTTCA (SEQ ID NO: 134) |
| CD2248 | GCATTGGATAAAGGACTGTGC (SEQ ID NO: 135) | CAAGCTCTGTCTTTGGAGCA (SEQ ID NO: 136) |
| CD2264 | TGAAGGACTTGACCAAAATGAA (SEQ ID NO: 137) | TTTTTCTTTCCACCTCTTTTGA (SEQ ID NO: 138) |
| CD2274 | CATGGAATAATTCGAGTGTTGAA (SEQ ID NO: 139) | GTTCTCCCAGGAGCCTTTTT (SEQ ID NO: 140) |
| CD2300 | TGAATGATATGGCAAGAGATGT (SEQ ID NO: 141) | CCTGTTCCCCAATCAATCTG (SEQ ID NO: 142) |
| CD2306 | TGCACCATAATTGTTAGAGCAAA (SEQ ID NO: 143) | TTTTTATTTTAGTGCACACTCTCC (SEQ ID NO: 144) |
| CD2309 | GGATAAATGTACACATATGTTAACTGC (SEQ ID NO: 145) | CTTGATGCAAGCAAGATTCC (SEQ ID NO: 146) |

TABLE 4-continued

Nucleotide sequences of primers directed to the genes listed in Example 2

| CD No. | fwd primer | rev primer |
|---|---|---|
| CD2563 | AAAGAAGCAATGAAAAACGAGAA (SEQ ID NO: 147) | TTTTCTACTTAACCTTTCAGGTCCA (SEQ ID NO: 148) |
| CD3188 | TGAGCAAAAGTGAATTAACAGCA (SEQ ID NO: 149) | TTTTCCAATCCATTTCTTCCA (SEQ ID NO: 150) |
| CD3288 | GATGATGAAATCACCTTAGGTAGTGA (SEQ ID NO: 151) | ACCCAAATCTCATCTAGCACAAA (SEQ ID NO: 152) |
| CD3321 | AATGTTCCATTTGACTATGTTCG (SEQ ID NO: 153) | GGAGGAAATTCATCATCTCCA (SEQ ID NO: 154) |
| CD3367 | TGGTTAAGAAAAATGAAACTGTAGGA (SEQ ID NO: 155) | GCATATTTTCAAGCTCTTCACG (SEQ ID NO: 156) |
| CD3369 | TTCAAGAAAGCATTCCTATCACA (SEQ ID NO: 157) | TCTTTGCTTACAACTATACCACCTTTT (SEQ ID NO: 158) |
| CD3609 | TGTTTAAGAAAATGGCAGTACTAAAAG (SEQ ID NO: 159) | TTTTTATCTTTACCTCAGCTACAAAGG (SEQ ID NO: 160) |
| CD3656 | TTGTTGTTTATGCTAATAATGTGGA (SEQ ID NO: 161) | TTCTATTTTTGAAAACTCTTCTTTCTC (SEQ ID NO: 162) |

Example 3

Introduction

Using microarray analysis, expression of CD3635, CD3638, CD0638, CD1424, CD1487, CD1543a, CD1794, CD1906, CD2046, CD2098, CD2216, CD2264, CD2274, CD2309, CD3188, CD3288, CD3367 and CD3609 was assessed in *Clostridium difficile* strain 630.

Materials and Methods

Bacterial Cell Culture.

*Clostridium difficile* strain 630 was routinely maintained on BHI agar or grown in BHI broth (Oxoid) at 37° C. in a MACS MG500 Anaerobic workstation fitted with an airlock (Don Whitley Scientific, UK). Heat stress was induced in broth cultures in the early exponential phase of growth using a water bath set at 41° C. and cells were harvested in biological triplicates at late log phase ($D_{650}$=1.1) of anaerobic growth as described by Jain et al (Jain S, Graham C, Graham R L J, McMullan G, Ternan, NG (2011) A quantitative proteomic analysis of the heat stress response in *Clostridium difficile* strain 630. J Proteome Res 10(9): 3880-3890).

Total RNA Isolation.

RNA was extracted from aliquots of $4 \times 10^8$ cells from both control and heat-stressed triplicate cultures of *C. difficile* strain 630 using a Qiagen RNEasy mini kit. The Qiagen protocol was modified to include a mechanical lysis step—cells in TE buffer with proteinase K and lysozyme were added to a Lysing Matrix A tube (MP Biomedicals) and treated in a Fastprep FP120 machine (MP Biomedical) at speed 5.5 for 30 s to break open the cells. Following both on-column and in-solution DNAse digestions, and a final on column cleanup, RNA samples were confirmed free of contaminating genomic DNA by performing PCR with tpi primers (Lemeé L, Dhalluin A, Pestel-Caron M, Lemeland J F, Pons J L (2004) Multilocus sequence typing analysis of human and animal *Clostridium difficile* isolates of various toxigenic types. J Clin Microbiol 42: 2609-2617). RNA Samples were stored at −70° C. until required for microarray experiments or for qRT-PCR.

Template Labelling and Microarray Hybridisations.

Microarray experimentation was out-sourced to Oxford Gene Technology (OGT; Begbroke Science Park, Oxford, UK). RNA samples were sent on dry ice to OGT where the quality and integrity of the 16S and 23S ribosomal RNA (rRNA) subunits was verified by using the 2100 Bioanalyzer system (Agilent Technologies). For all six RNA samples, an RNA integrity number of >9.6 was obtained, with A260/280 values of >2.0, and 23S:16S rRNA ratios of >1.4. Using Ambion's MessageAmp™ II-Bacteria RNA Amplification Kit, the template mRNA samples were: (a) polyadenylated; (b) the mRNA samples with a stable poly(A) tail were reverse-transcribed into first strand cDNA using an oligo (dT)-primer bearing a T7 promoter; (c) the cDNA samples were then converted into double-stranded DNA (dsDNA); (d) dsDNA was then used as a template for in vitro transcription with T7 RNA polymerase to generate antisense RNA (aRNA); (e) aRNA was then finally labelled with fluorescent dyes (Cy3 and Cy5) to create labelled probes for hybridisation. In this investigation, a dye-swap (i.e. control samples labelled with Cy3 and heat-stress samples labelled with Cy5 and vice versa) was performed in order to generate technical replicates and to compensate for any potential bias introduced as a result of inherent discrepancies in Cy dye incorporation (Do J H, Choi D K (2007) cDNA Labeling Strategies for Microarrays Using Fluorescent Dyes. Eng Life Sci 7(1): 26-34). Prior to hybridisation, labelled aRNA was purified using Qiagen's RNeasy® MinElute Cleanup Kit as per the manufacturer's instructions. The labelled probes were then hybridised to a *C. difficile* strain 630 array (BUGS CD630 gene expression array plus Plasmid pCD630, 8×15 k array, v2.01) comprising 3,776 genes using the Gene Expression Hybridisation Kit (Agilent Technologies) as described in the manufacturer's protocol.

Microarray Data Analysis.

The hybridised arrays were subsequently scanned at 532 nm and 635 nm, corresponding to Cy3 and Cy5 excitation maxima, using an Agilent C Microarray Scanner equipped with the extended dynamic range (XDR) software for improved resolution. The data was then extracted from raw microarray image files and the probe signals were subsequently quantified using Agilent's Feature Extraction Software version 10.5.1.1. Upon normalisation by the locally weighted scatterplot smoothing (LOWESS) algorithm, the data was imported to GeneSpring GX version 11.0 (Agilent Technologies) where the minimum fluorescence intensity was set to 1. The mean normalised $\log_2$ fluorescence ratios and standard errors of mean were then calculated across all probes for an individual gene and concatenated to gene level. The microarray data has been deposited in NCBI's Gene Expression Omnibus (Edgar R, Domrachev M, Lash AE (2002) Gene Expression Omnibus: NCBI gene expression and hybridization array data repository. Nucl Acid Res 30(1): 207-210) and is accessible through GEO Series accession number GSE37442 (http://www.ncbi.nlm.nih-.gov/geo/query/acc.cqi?acc=GSE37442).

Results and Conclusion

The data in Table 5 below shows the raw average fluorescence (raw avg fluor) and the expression relative to triosephosphate isomerase (tpi) expression (relative exp) for each of the genes CD3635, CD3638, CD0638, CD1424, CD1487, CD1543a, CD1794, CD1906, CD2046, CD2098, CD2216, CD2264, CD2274, CD2309, CD3188, CD3288, CD3367 and CD3609. These data show that each of these genes is expressed in *Clostridium difficile* strain 630.

TABLE 5

| Gene | Name | raw avg fluor | relative exp |
|---|---|---|---|
| tpi | triosephosphate isomerase (reference gene) | 1946 | 1.00 |
| CD3609 | hypothetical protein | 40428 | 20.77 |
| CD2309 | hypothetical protein | 28239 | 14.51 |
| CD1543A | hypothetical protein | 4363 | 2.24 |
| CD2046 | hypothetical protein | 2593 | 1.33 |
| CD1424 | hypothetical protein | 1028 | 0.53 |
| CD2098 | hypothetical protein | 567 | 0.29 |
| CD3288 | hypothetical protein | 522 | 0.27 |
| CD0638 | hypothetical protein | 278 | 0.14 |
| CD2274 | hypothetical protein | 231 | 0.12 |
| CD2216 | hypothetical protein | 71 | 0.04 |
| CD3188 | hypothetical protein | 39 | 0.02 |
| CD1487 | hypothetical protein | 33 | 0.02 |
| CD3635 | hypothetical protein | 30 | 0.02 |
| CD2264 | hypothetical protein | 26 | 0.01 |
| CD3367 | hypothetical protein | 22 | 0.01 |
| CD1794 | hypothetical protein | 19 | 0.01 |
| CD3638 | hypothetical protein | 18 | 0.01 |
| CD1906 | hypothetical protein | 17 | 0.01 |

Example 4

Introduction

The study described in Example 1 was expanded. In this expanded study, the presence of each of CD0588, CD0638, CD1234, CD1423, CD1424, CD1487, CD1543a, CD1728, CD1794, CD1897, CD1906, CD2046, CD2098, CD2216, CD2248, CD2264, CD2274, CD2300, CD2306, CD2309, CD2563, CD3188, CD3288, CD3321, CD3367, CD3369, CD3609, CD3656, CD3617, CD3618, CD3635 and CD3638 was screened for in the 41 *Clostridium difficile* clinical isolates of Example 1 and, where a gene was detected as being present in those 41 clinical isolates, the presence of that gene was screened for in 41 further *Clostridium difficile* clinical isolates.

Methodology

In this expanded study, the materials and methods used were the same as the materials and methods described in Example 1.

For the genes detected in all of the clinical isolates tested, the nucleotide sequences of the primers used, the coding nucleotide sequences of the genes, the amplicon sizes and the melting temperatures of the primers are set forth in Table 6.

A list of the 82 *Clostridium difficile* clinical isolates obtained from the Royal Victoria Hospital (RVH) which were used in this study and the ribotypes thereof are set forth in Table 7. Note that the clinical isolates numbered 1-41 are the clinical isolates (strains) used in Example 1 (as listed in Table 2).

A list of the negative control strains used are set forth in Table 8.

In a first screen, each of the *Clostridium difficile* clinical isolates numbered 1-41 in Table 7 was screened for the presence of each of the genes CD0588, CD0638, CD1234, CD1423, CD1424, CD1487, CD1543a, CD1728, CD1794, CD1897, CD1906, CD2046, CD2098, CD2216, CD2248, CD2264, CD2274, CD2300, CD2306, CD2309, CD2563, CD3188, CD3288, CD3321, CD3367, CD3369, CD3609, CD3656, CD3617, CD3618, CD3635 and CD3638. If a given gene was detected as present in all of the *Clostridium difficile* clinical isolates numbered 1-41, then, in a second screen, each of the *Clostridium difficile* clinical isolates numbered 42-82 in Table 7 was screened for the presence of that gene. If a given gene was detected in all 82 *Clostridium difficile* clinical isolates, negative control strains as set forth in Table 8 were screened (in a third screen) for the presence of that gene.

Results and Discussion

The results of this study are presented in Table 9. In Table 9, a "+" sign indicates that a gene was detected as present in all of the clinical isolates in the relevant screen, and a "−" sign indicates that a gene was not detected in all of the clinical isolates in the relevant screen. "Low sensitivity levels" means that the sensitivity of the PCR was such that a conclusion could not be drawn as to whether a gene was present or not; in these cases optimization of PCR cycling conditions will be required in order to determine whether these genes are present in the tested *Clostridium difficile* clinical isolates.

In this study it has been demonstrated that CD0638, CD1424, CD1487, CD1543a, CD1794, CD1906, CD2046, CD2098, CD2216, CD2264, CD2274, CD2309, CD3188, CD3288, CD3367, CD3609, CD3635 and CD3638 are detectable in 82 *Clostridium difficile* clinical isolates of varying ribotypes.

TABLE 6

Nucleotide sequences of primers, coding nucleotide sequences of genes, amplicon sizes and melting temperatures (Tm) of primers

| Gene | Sequence | F primer | R primer | Amp size | Tm |
|---|---|---|---|---|---|
| CD0638 | TTGTTTATTTTGAATTTTGGAGGATTAATTATGGATTCAAATAATAATACTATAAAATCA ACTGTTAAAAGGGTATTTCTTTTGGTTCTTGTTTAGCAATGATTATTTCTTATACTGCA TGGAAATCTATTCCATGGGCTATTTTTCATGGCTTAATGAGTTGGATATATGTACTTTAT TATTGGGTTAAGTATGCATAG (SEQ ID NO: 21) | TGTTTATT TTGAATTT TGGAGGA TT (SEQ ID NO: 37) | CATGAAA AATAGCCC ATGGAA (SEQ ID NO: 38) | 150 | 59 |

TABLE 6 -continued

Nucleotide sequences of primers, coding nucleotide sequences of genes, amplicon sizes and melting temperatures (Tm) of primers

| Gene | Sequence | F primer | R primer | Amp size | Tm |
|---|---|---|---|---|---|
| CD1424 | ATGTTTAGAGATGAAATGGATAAATGTACACACATGTTAACTGCTTATATTAGTAGTTTA TATGATTATTGTGATTTTATAGATACACAGCTAGATGATTTTATACTAGAGTACGGAGAA AATGTAGTAGAATCTTGTTTACATCAAGTGATGGTATTGGTAAGTAAGTATAATTAA (SEQ ID NO: 22) | AGATGAA ATGGATA AATGTAC ACACA (SEQ ID NO: 39) | CCATCACT TGATGTAA ACAAGATT C (SEQ ID NO: 40) | 146 | 59 |
| CD1487 | ATGGAAAATGATACTATTAAGGCTGATGATATTCTCAATTATTGTCTATCAAACTTAGAT GATGTTGTACTAATGGATAGTTGGGGGAACGAGCAATTTACTACAATCCTAATGGTGTT TTAAAGCGAGGGGTATATGTTCTTACCATTAAGGAAAAAGACAGTAATAATGATAAAGGT TCGTTAGTTAGTCGTCCAAATGTATACCGTGTGAATATAGGATTAAAAAAAGAAACTTTT ATTGAAATGTTTGGATATATTCCAAAGCGTCCAGGTGTAGGTCAAATAGTTGATATGGAT TTTGATTTTACAAAATTGGACACAATCATGCCACATCCTATCTACTCATGGATGGGATGG ATATGCGTCCTAAGCCCTACTGAAAAGACATTTGAGAACTTTAAAACTTTAATAGGAGAA TCTTACAATTTTGCAAAACAAAAATTTAAAAAGAGAAAAAACAAGTAA (SEQ ID NO: 23) | GGGGGAA CGAGCAA TTTACTA (SEQ ID NO: 41) | ACCTACAC CTGGACGC TTTG (SEQ ID NO: 42) | 199 | 60 |
| CD1543a | ATGCGAGAAGAAAAAAGTAATGAAAAGTATGATTGTTATTGGTGTAATCAAGAGAATAAT TTCTGTGTAGAAATAAAAGATAATATAGTCATGATAGATGATGGCACTGGTACGTTAAAA CAAGCCGTTTTCATAGGGTATAAACAAATCCAAATTAATTTAAACTGTTCACATTGTCAA AACTTAAATAGAATAAAATTAAATTTGTAG (SEQ ID NO: 24) | TGATTGTT ATTGGTGT AATCAAG AGAA (SEQ ID NO: 43) | ACCCTATG AAAACGG CTTGTT (SEQ ID NO: 44) | 110 | 60 |
| CD1794 | TTGTTTATAGATGAAGAATTAGAAGGTTATATATTAACATGTAAAATATCTGAAGACTTT AAAAATATACCTGAATATAGTGATGAAGAGTTTTATGTTACAGTCTATAAAGATGAAAGT TCTGACTCTGGGTACTATGCTTTATTAGAAAATAAAGAAGAAAGAGTTGTATGGGATGGA GAAGTTGTTGCCAATAATATTTTTAATAACCTTTGGATTGTAGTAAATAAGGTTAAAACT GGATAA (SEQ ID NO: 25) | ATAAAGA TGAAAGT TCTGACTC TGG (SEQ ID NO: 45) | TTAACCTT ATTTACTA CAATCCAA AGG (SEQ ID NO: 46) | 130 | 57 |
| CD1906 | TTGCATATGGAAATCAATGTTATAGAAATTTTCCCTAAAGATAAAGCTAAACTTAATAAA ATAGAAATGGATAAAGCTAGTTGGTTTGTAAATATAATAAGTAAAAAATATCCTAAAGAA GCTTTAAATGAAGCATTTAGTACTTTAGAAAAAGAATTAAATATAAGTAAAGCTAATACA TAA (SEQ ID NO: 26) | TGCATAT GGAAATC AATGTTAT AGAAA (SEQ ID NO: 47) | TGCTTCAT TTAAAGCT TCTTTAGG ATA (SEQ ID NO: 48) | 134 | 60 |
| CD2046 | GTGGATGAAATGCTTGTATATAATAAAAGTTTTTATCCTAATGACATATTTCCAAGATTA GATTTTTCAAAAATAAAAAAACAGTTAAAATTGATAGATAATGACCTGTCAGATTTTGGA AGCATATGTATAATAGAAAAGAACATTATACGATAAGTGTAAACAGTATAGGTGAAATA AATGTGTACTATGATTTAGAGTACGAAAATAAGGTGTATAGAATAGTTTATGAGATTGAA AAGTTATTTAAATCTCAAGTTGGAAGGTTTAGCATATCTACATACAGAAATTGA (SEQ ID NO: 27) | ACCTGTC AGATTTTG GAAGCA (SEQ ID NO: 49) | TGCTAAAC CTTCCAAC TTGAGAT (SEQ ID NO: 50) | 171 | 59 |
| CD2098 | TTGGCTGGTAATCTAAATAATATGAGAGCAGTAAATAATTTTAGAGGAGATAAGAACATT TTAGAATGTTTAGTCAGCTTTGAGGGTCGTTCAATAAGTCAGAGAAAAGTAAGGGTATTT TTTAAAGAAAACAAAATCAAATAGAAATTGATTTTGCAGAAGAGGAAATTTCTAAATTG GTTGAAAATGTTGTTTTAAATACATCATATCAAGAAATGTTATATGATGAAATAGAGAAA CAACTGGAAATTGATTGTATAGGTACTTGGATGATATTATCTAAATTAAAAGATGGTAGT AGAGTTCACTGA (SEQ ID NO: 28) | GTCAGCTT TGAGGGT CGTTC (SEQ ID NO: 51) | ACAATCA ATTTCCAG TTGTTTCT CT (SEQ ID NO: 52) | 186 | 59 |
| CD2216 | ATGATTGTGATTGAAGGTAGCGATAAATTTAAGATTGCAAAAGAATATATTGATGTAGAA TATACTCTTTTTAGCAAAGTAACTTTTTAGGTATGAAAAGTTGAAATTTAAAGATAATGCT GAATTGGAAAAAATTAAGATGTTTAAATATAAAAATGGCTACATCCCTAATAAATTAAAC CTTTCTTTTGGATATGGATTCTCTTCTTATAAAAAGCAAATAATTAGAGAAACTGTAGAT ACTTTAAGATTGACAGAAATTTTTTCAAGCGAGAACATAGAGATATTAAATTTATAAAA GATGGTACAAAAAAATTAGAAATTAGCATAGAGAAAGTTGTGAAATTTAAACGTCGAAAA AAAAGAAATTATGTTTGTTGCTATTGCCCTGATATGTATAGGGACATAAAACTCGACAAA GAATCTATCAATAAGATATACAACAGAAAATAAAAATAGAAAGAGAAGTTAATATTTTT GAAGATGAGGATGTTATAATAAACAAAAAGTATTGAAGTTTCCAAAGTCTTGGACAAAG AATATGCAAAAATATTGGTTAAGTGAAAATAAGTATCCCATACATTCTACTGTAATTGAT GATGATAGATAAATGTTGTAATGTACAATATACAAAAAATAGAGTGATAATATTTATAT TACATATATAACCATTAA (SEQ ID NO: 29) | CCTTTCTT TTGGATAT GGATTCTC (SEQ ID NO: 53) | CAGGGCA ATAGCAA CAAACA (SEQ ID NO: 54) | 212 | 59 |
| CD2264 | GTGTTAAAAAAGTGGTTTGGTATTGTGAAAAAAAGACAAAAAAGTGAGTCAGTAAAAGAA GAAGGTGAAGTAATATTAAAAAACGAAAAAATATTATCTGAAGAAAAGTTGATAGATGAA GAAGGAGTTGTAGTTAATATTGATAATGAATATTAACTAAAGTAGAAGTAGTAAATGAT GACAATGAAATAGAAGAAAAAATAATAGAAGAAGATTGGTTAATTAGTGAAAATACCATA AAATTAGATGATAAAGAAGCAATTATTAATGATAAAAACATAGAATTATGTAAAAAAGAA GTTCAAGTTGAAGGTGAAAAAATAGATTTAAATAAGTTTGAAGGACTTGACCAAAATGAA | AAGAGTG GGTTTTTG ACACTCA (SEQ ID NO: 55) | AGCTCCAT TCACTTTT GCAGT (SEQ ID NO: 56) | 168 | 59 |

TABLE 6 -continued

Nucleotide sequences of primers, coding nucleotide sequences of genes, amplicon sizes and melting temperatures (Tm) of primers

| Gene | Sequence | F primer | R primer | Amp size | Tm |
|---|---|---|---|---|---|
| | AATTATAATCTAGAAAAAAATGTTATTGAAGAAAAGAAGTAAGTGAATGTTTGACAGAA<br>GAAGATTTAGAGTACATAAAAGAAATTAAAATAAAAAGAGGAAAAAGTATAAAAGCTATA<br>AACTTGTATACTAAAGAAGAGTGGGTTTTTGACACTCATATACAGTGTAGTAAAAAACTC<br>AAAGTTCCATTAGGGTACATAAGAGAAATTTAAAATATGGATATATGGATTACTTTGGA<br>GATGCAATAAATTATTTAAGTGAAGTATTAAATATAGATGAATACTGCAAAAGTGAATGG<br>AGCTATCTCGATAATAGCAAATCTCCATCTGAGATATTTAATATTCTAAACAATAAAATA<br>TTTAGTATAAGGCTTTCTAATGAAAAAAGAAATGAAATTTGACAAATGATAAAATTGAA<br>GCATTAAAAATGAATTATAGATTTGAATGTATTGATGAAGAATATGATGAATATTTTAAA<br>AAATATAAGTCTATAATCAAAAGAGGTGGAAAGAAAAAAGTTGAATTAGTAAATAAAAAA<br>GGTGACATTTTAGAAATATTTAAGTCTTTAGAAGAATGTGCCATTTATTTGCAAAAGGAA<br>AAGAATGAAGTTATACAAATGTTAAAATATGGAGATACAAAAGTAGGAAGAAACTTTATA<br>AGGTATAGTTTGAGAAGTATTTAA<br>(SEQ ID NO: 30) | | | | |
| CD2274 | ATGGATTTAAGTGGCATATTTAAATACTATTGTAAAGAGTGTGAAAATACATGGAATAAT<br>TCGAGTGTTGAATTATTTGAGAATATAGAAACGTATAGTAAAGATTCACAAAAAAAGAGG<br>GAAAAAGAATTAGATAAATTGCTAAATACAATATCAGTTCATTTAGAGAGGTATCCAAGT<br>GATGCTGTATTGAGAAAAATGTGGGTAAAAAAGGGCGAGGTTTTCTTACAAAAGACATTG<br>GAAAAAGAAAATATTTTTAAGTTAGAAAAAATGGATGTAGAGGATAGAAAAAATTTTTA<br>GATATAACAAAACAGTTTATTAGAGATGCTAGAAAATTTGATGATGATTTACCTATAGGT<br>GATATTATGCAAGCTATGAGGAATGTATGGATTTCAAATGCATTACAATTATTATTTGGT<br>AAAGAAGTATATTATTCAAAAGCTAACTTTGCATATAGTATGTTATATCCATATACTGAT<br>AATTATTTAGACAATACAAATATAGATAAAAATGATAAGATTTTATTTAATAACTGGTTA<br>GAAAAAAGGCTCCTGGGAGAACACATTAAATCTAAGGATTATCATGAAAGTAAAGTATCT<br>CAAATGATAGATTATATTGAAAGTGTATACCCTAGAGAAAAGTTTACAGAAGTTTATGAA<br>TCGTTATTATTAATATTTAAAAGTCAAGTAAAATAGTTTAAAACAACATGGTAAGGAAAT<br>CATTTGTGTAAAGAAGATTTATTATCCATTTCTATTGAAAAAGGAGGTTCATCCGTTTTA<br>GTAGATGGATATTTAATAAGTGGATTGATGACAAAGGAAGAAATAGAGTTTTGTATAGGA<br>TATGGATTTTTATTACAAATATCTGATGATTTACAAGATATAAAAGAAGATTTAAAATAC<br>AACCATAAAACTATTATTACAGAGATGTCAAAAGAGGGTACTTTAGATAAAGTTGTAAAT<br>AAACTAATAAATTTTACTATTGAGTTAATAGATAGTTTTAAAATTAATAATAAAAATAAA<br>TCTGTAATAACTATGATAAAGAATGATTGCTTAATGTTAATTTTATTTTCTGTAGTTTAT<br>AATGCTGAATTTTTTTCTGTAGGATATATAAAAGAAGTAGAGAAATTTATTCCATATACA<br>ATAGATTATTCATTAGAGATTGAAGAAAAATAAAAGAAAAATTTAAAAATATAGATGTT<br>TTAAATAATGAAATGAATATAAAGAAATGATTGATATTATTTGTGCAGAGTAG<br>(SEQ ID NO: 31) | AAAAAGG<br>CTCCTGG<br>GAGAAC<br>(SEQ ID<br>NO: 57) | CGGATGA<br>ACCTCCTT<br>TTTCA<br>(SEQ ID<br>NO: 58) | 228 | 60 |
| CD2309 | ATGTTTAGAGATAAAATGGATAAATGTACACATATGTTAACTGCTTATATTGGTAGTTCA<br>TATGATTATTGTGATTTTATAGATACACAGTTAGATGATTTTATATTAGAGTACGGAGAA<br>AAAGTTGTGGAATCTTGCTTGCATCAAGTGATGGTATTGGTAAGTAAGTATAATTAG<br>(SEQ ID NO: 32) | GGATAAA<br>TGTACAC<br>ATATGTTA<br>ACTGC<br>(SEQ ID<br>NO: 59) | GCAAGCA<br>AGATTCCA<br>CAACT<br>(SEQ ID<br>NO: 60) | 125 | 57 |
| CD3188 | ATGAGCAAAAGTGAATTAACAGCAGAAACAACAGAAGAAATGTTAGAAGTACTAAGTGGT<br>AAAGATTATGATATTGCATGTCATTTACATGAACTTGGTAAATCATTAGATTGTAAAATT<br>GAACCAAAAACAGGTGCTCGTTCTTACAAAATAGTATATTCAACTAAGAAACCAAAACGT<br>AGCTTATTTACTATTGAATGTAATGAAAAAAAATGGAGAGTTAAAGCAAATCTTTTTCAT<br>CTAAATACATATAAAGATGCTGTGGAGGAATGCTCTAAAACTATTAAAGATAGTATAACT<br>AAAACTCGTACTTGTAAGAAATGTAATTCAAAGTGTATTGGAGGTTCTTCGTTTGAATTA<br>GATGGAAAGTCTTACCTGACTTGCATAGGAAGTGGTCATTATTTTGCAAATATGGAAGAA<br>ATGGATTGGAAAAACCTAGAAAAATTAATTACTAAAGAAAATAATATTATGCAGGAATCT<br>GTATAG<br>(SEQ ID NO: 33) | ACCAAAA<br>ACAGGTG<br>CTCGTT<br>(SEQ ID<br>NO: 61) | AGAGCATT<br>CCTCCACA<br>GCAT<br>(SEQ ID<br>NO: 62) | 154 | 60 |
| CD3288 | ATGGACTATATAGGAATAGAAAATATAACACCTTATGAAAATACATATGAATTTAGTGTA<br>TATGAATATGATGATGAAATCACCTTAGGTAGTGAAAAGTTATATGTATGTGAATTAAGG<br>GTTGTATTGATTAAAGTTAATTCTCTGTATGTTGAAAGATTGCATAAATCAGTTGAAGCA<br>ATGGTCTTAGTAAAAAATTTGAAAAAAGATTTAGATAAAACACTTGTTGTAAACAAAATA<br>AAGAATTTTGTGCTAGATGAGATTTGGGTAGAAAATCTAGTAAAAGAGAATATAGAAGTT<br>ATATTTGTAGAAAAGCTAG<br>(SEQ ID NO: 34) | TGATGAA<br>ATCACCTT<br>AGGTAGT<br>GAA<br>(SEQ ID<br>NO: 63) | CCCAAATC<br>TCATCTAG<br>CACAAA<br>(SEQ ID<br>NO: 64) | 197 | 59 |
| CD3367 | ATGAAAATATCTAGTCAATATAGAAGTCAATATTCATTTAGATATGAAAGTAATATAAAT<br>AATACAAGAATAAATGAAAGTATGGTTAAGAAAAATGAAACTGTAGGAAAAGACACTTAT<br>TTATCTAATATTATGAAACAAAAGCAAGAACTTAATGATAGAATTAGAGATTTAAAATAT<br>AGACAAGAGGTTTATACTAAAAAAATAAATGACGCAATTAAGAACTTATGTAAATCAGAA<br>ATAAGAGAAACAACTAATAATTTTTCTAATATAGAAATAGGTATTAAAAATAGCATTATA<br>GAAGAGAAAATAAAGTACAATGTTAGATGAAAATTCAACTTATCTAAATACAAATGAT<br>GAAAAAGAATCTTTAATCACTAAAGAGTCTAATGAAAAATTGAAGAAGAAATATTAAAT<br>GATGAAAAATTAGAAGAGTTAGAACAAAAAAAGGATTATAAGAGGATTCTAATAAAAAA<br>GAGAAAGTATCTGAGGACTTATCTTTAGTAGGTAAAACTCGTGAAGAGCTTGAAAATATG | AAAACTC<br>GTGAAGA<br>GCTTGAA<br>AA<br>(SEQ ID<br>NO: 65) | TGAATTTT<br>GTTTGTAT<br>TCTTCAGC<br>A<br>(SEQ ID<br>NO: 66) | 126 | 60 |

TABLE 6 -continued

Nucleotide sequences of primers, coding nucleotide sequences of genes, amplicon sizes and melting temperatures (Tm) of primers

| Gene | Sequence | F primer | R primer | Amp size | Tm |
|---|---|---|---|---|---|
| | CTTAAAAATTTTATAAATTTAACACAAGAAGAAATAATGAAACTTGAGTCGAGAATAGAA<br>AAGTTAGATAAAAATGCTGAAGAATACAAACAAAATTCAAAGACTAATATATTTGATAAA<br>ACAGATGAACAAAAAAAACATATAAATGTACTGATTTAA<br>(SEQ ID NO: 35) | | | | |
| CD3609 | ATGTTTAAGAAAATGGCAGTACTAAAAGATATAGCAACTAAAATAGGTCGTAAAAAAGCG<br>TATGAACTATTAGAAATGGTTGAAGGTAATGATGCCTTTGTAGCTGAGGTAAAGATAAAA<br>AAGAATGGAATAGAATCTAAAAAAGAAGAAATTATGTTAAAAGATAATCAAAAAATAATA<br>TTAGAGTATATAGAAGGTTAA<br>(SEQ ID NO: 36) | AAAATGG<br>CAGTACT<br>AAAAGAT<br>ATAGCA<br>(SEQ ID<br>NO: 67) | CCTCAGCT<br>ACAAAGG<br>CATCA<br>(SEQ ID<br>NO: 68) | 100 | 59 |
| CD3635 | ATGGCTATGGGTTTTGAATTTAAAATAATGAGAAGTTTAATATATGTAGGACTTGCCAAG<br>GAAGAATATAGACCTAAGCTAATGGACTGGTTATATCGTCACCATATTCCAGATAGTATT<br>AGCACTTTTGGACCATATTGTACTAAATATGCCTTTTATCAAGCATATCCTACACCAAAT<br>GAAGGTGAGCGTTTTGGTGCACGTAAGATGCAACTAACAGAACATTATTGGCTTGTAGAT<br>GAACATATGCCTGAGATGGCAAATAGAATTATGACAGAATATATGCCTATGGATGTTCTA<br>CGTTGGCAAGGGTGTATACCAGATGTAGAAAATAAAAGGGTTCATGAAAATGCAGAAAGT<br>GGAGATGCAGGACGTGCGTAGGTGGAGATAATGGATGTCCACCATTTATATTTGCCTTT<br>GTTCCAATAAACTGGGAAGAAGACTTTAGAGGAAAAGGACGTACTGTACAAGATGGACCA<br>AACTATCGTTGGCAATTTATGATTAAGTATCCAGATGGTATCTCTAAAGAAGAAGGAGAA<br>AAATGGTTCTATGATGAGGTAGTGCCATACTTTACAAACTGTTGCTATGTTAATCGTTTT<br>GTCAGTAGTAAAATAATGATTAATTATGGAGCAACTGCTTTTGACCGTGTATCAGAACTA<br>TGGTTTGAAGGGGAAGAAGAATGGTATAAAGCTGTGGTTGAAGAAACAAAGTCGTTTATT<br>AAAAAACCAGAATGGGCACAAGAAGAGGAGTTCCCATATTTAAAACCACAATTCAATATC<br>GCATCAGTATTCTTAGGTGATATAGCAACTATGGATGCATACTCACAGTATCGTGGATAT<br>ATACCAATGAGATAA<br>(SEQ ID NO: 4) | CATATGC<br>CTGAGAT<br>GGCAAA<br>(SEQ ID<br>NO: 17) | CTTGTGCC<br>CATTCTGG<br>TTTT<br>(SEQ ID<br>NO: 18) | 499 | |
| CD3638 | ATGGAAGATAAATTTTATGCAAAAGGCAACGGAAATAACGGATATATTAAAAATCTTGAA<br>GTTGTTCCTTTAATAACTTAGATGGAACTTGTGGAATGTTTCAAATGGCTCTGTACAAA<br>AGAGATGAAAAATACTATTTATATGGATGCTGTTTTGGAGGAAATAAAAAAATGGAGTA<br>ATGATTAGCGATATTACAGACCCTTATAATCCACAATTTATAAAACATTTTCAAATGTTA<br>GACCCTAAAGAGTATCCTACAACAACAACTCCCAAAATTCAAATAGCAGATGATTTAATG<br>ATAGTAGCAATGAGTTGTGGAAGTGGACCAGGAGCACTTGTTGACCAAGCTAAATTAGCA<br>AATATTAAGTGTGAAGCAGGAATTAGAATATACAGTTTAAAAGAAGACCCTTTAAATCCT<br>AAGTTTTTAGGATATTGGGATTGTGGCTTAAAGCATGTAATGGGTGTTCATAGATTTATG<br>TACAATGGTGGAAGATATGTACATTTATCAAGTGATTGTGTTGGCTTTGAAGGTCTGATT<br>TATAGGGTCATAGATATAATAAATCCTACTAATCCAGTGGAAATAGGTAAATGGTGGAGA<br>CCAGACCAATATGCAGATGGATATCCAAATAGAACTTTTGATGCAGGAGCACCTCATTGC<br>CCAGAATTTATGGATAAAGGATGGCTTCATGGACCTCCATTTGTAAGAGACGGAAAAGCA<br>TATTGTGGTTATGGAGGAGCTGGTTTAGTTGTATTAGATGTTGAAGATTTAACAAGACCA<br>AGATGCTTAGGTGAATTGCCATTTACGCCTGCATTTTCTAGTAGACTTGCAGGTGCAAGA<br>ACTCATACAGCATTACCATTGCCAGGAAGAGATTTAGTCGTTGTTCAAAATGAGGGAGAA<br>AGATTCCAGTTCTTTAAACCAGATAACATTACAGATGTTCAAGCTATGAATAATATACAT<br>ATGGTTGATGTTAGTGACCCAACAAAACCAACATTAATTGCTCAATTTCCATATCCTGAA<br>GTTCCAAAAGATTTCCCTTATCCTAACTTTAATGTTGCGGGATTAGGAAAACCAGGGCCA<br>TTTGGCCCACATAATCTTCATGAACCAATGGATAATAAGCCATGGTTAGAGCAAAGAGGA<br>GATAGAGTATATTGCTGTTATTTCCATGCAGGGCTAAGGGTTTATGATGTATCAGACCCA<br>TATTATATCAAAGAGCTAGCATATTTTATACCACCAAATCCAATAAAACACCAGAAGAA<br>TCTTATTTCCCAGGATTCCCAGGACCACGCTTGGCAGTAACAGAAGATCTTATCGTTGAT<br>GATAGAGGCTACATCATCATAGATGCTTTAGATGATGGATTCTATATATTAAAAATGAAA<br>GATGATTAA<br>(SEQ ID NO: 5) | GGATGCT<br>GTTTTGGA<br>GGAAA<br>(SEQ ID<br>NO: 19) | AAATTCTG<br>GGCAATG<br>AGGTG<br>(SEQ ID<br>NO: 20) | 525 | |

TABLE 7

List of 82 Clostridium difficile clinical isolates

| | RVH ref No. | Ribotype |
|---|---|---|
| 1 | 100058-106 | 106 |
| 2 | 100048-106 | 106 |
| 3 | 090092-106 | 106 |
| 4 | 100059-106 | 106 |
| 5 | 100150-078 | 078 |
| 6 | 090126-106 | 106 |
| 7 | 090269-106 | 106 |
| 8 | 100149-078 | 078 |
| 9 | 090160-106 | 106 |
| 10 | 100162-020 | 020 |
| 11 | 090389-106 | 106 |
| 12 | 090361-106 | 106 |
| 13 | 090183-106 | 106 |
| 14 | 090391-106 | 106 |
| 15 | 090129-106 | 106 |
| 16 | 090217-106 | 106 |
| 17 | 090225-106 | 106 |
| 18 | 090223-106 | 106 |
| 19 | 090645-106 | 106 |
| 20 | 090294-106 | 106 |

TABLE 7-continued

List of 82 Clostridium difficile clinical isolates

|    | RVH ref No.     | Ribotype |
|----|-----------------|----------|
| 21 | 090540-106      | 106      |
| 22 | 100063-106      | 106      |
| 23 | 100158-078      | 078      |
| 24 | 100170-001      | 001      |
| 25 | 100171-001      | 001      |
| 26 | 100172-020      | 020      |
| 27 | 100173-078v     | 078v     |
| 28 | 100177-005      | 005      |
| 29 | 100163-026      | 026      |
| 30 | 100178-106      | 106      |
| 31 | 100164-014      | 014      |
| 32 | 100167-001      | 001      |
| 33 | 100168-001      | 001      |
| 34 | 100169-078      | 078      |
| 35 | 100143-026      | 026      |
| 36 | 100144-014      | 014      |
| 37 | 100146-005      | 005      |
| 38 | 100147-014      | 014      |
| 39 | 100142-005      | 005      |
| 40 | 100140ii-020    | 020      |
| 41 | 100153-001      | 001      |
| 42 | CD110020 015    | 015      |
| 43 | CD110040 015    | 015      |
| 44 | CD110050 015    | 015      |
| 45 | CD110055 015    | 015      |
| 46 | CD110060 027    | 027      |
| 47 | CD110072 026    | 026      |
| 48 | CD110107 015-19 | 015-19   |
| 49 | CD110119 026    | 026      |
| 50 | CD110147 026    | 026      |
| 51 | CD110166 015    | 015      |
| 52 | CD110172 023    | 023      |
| 53 | CD110183 023    | 023      |
| 54 | CD110185 023    | 023      |
| 55 | CD110235 027    | 027      |
| 56 | CD110243 026    | 026      |
| 57 | CD110244 027    | 027      |
| 58 | CD110251 015-19 | 015-19   |
| 59 | CD110272 023    | 023      |
| 60 | CD110373 027    | 027      |
| 61 | CD110379 015    | 015      |
| 62 | CD110425 027    | 027      |
| 63 | CD110441 015    | 015      |
| 64 | CD110446 023    | 023      |
| 65 | CD110460 015    | 015      |
| 66 | CD110465 023    | 023      |
| 67 | CD110729 002    | 002      |
| 68 | CD110732 002    | 002      |
| 69 | CD110779 002    | 002      |
| 70 | CD110798 002    | 002      |
| 71 | CD110800 023    | 023      |
| 72 | CD110811 002    | 002      |
| 73 | CD110830 053    | 053      |
| 74 | CD110831 053    | 053      |
| 75 | CD110835 053    | 053      |
| 76 | CD110837 002    | 002      |
| 77 | CD110840 015-19 | 015-19   |
| 78 | CD110849 015-19 | 015-19   |
| 79 | CD110851 002    | 002      |
| 80 | CD110856 002    | 002      |
| 81 | CD110862 ?tox-  | 140      |
| 82 | CD110863 ?tox-  | 140      |

TABLE 8

List of negative control strains

| Name | Number |
|---|---|
| Staphylococcus epidermidis | DSM 20044 |
| Staphylococcus aureus | ATCC 12600 |
| Escherichia coli | ATCC 11775 |
| Salmonella typhimurium | ATCC 14028 |
| Bacillus subtilis | ATCC 6051 |
| Clostridium acetobutylicum | DSM 792 |
| Roseburia inulinivorans | DSM 16841 |
| Eubacterium rectale | DSM 17629 |
| Clostridium novyi | DSM 14992 |
| Clostridium sporogenes | DSM 795 |
| Faecalibacterium prausnitzii | DSM 17677 |
| Streptococcus thermophilus | NCIMB 702681 |
| Bifidobacterium adolescentis | DSMZ 20083 |
| Bifidobacterium longum subsp. longum | DSMZ 20219 |
| Ruminococcus gauvreauii | DSMZ 19829 |
| Ruminococcus luti (Blautia luti) | DSMZ 14534 |
| Lactobacillus casei | DSMZ 20011 |
| Lactobacillus reuteri | DSMZ 20016 |
| Bacteroides vulgatus | DSMZ 1447 |
| Bacteroides intestinalis | DSMZ 17393 |

TABLE 9

Results of the Study described in Example 4

| Gene | First Screen (Clinical isolates 1-41) | Second Screen (Clinical isolates 42-82) | Third Screen (negative control) |
|---|---|---|---|
| CD0588 | Low Sensitivity Level | | |
| CD0638 | + | + | − |
| CD1234 | Low Sensitivity Level | | |
| CD1423 | − | | |
| CD1424 | + | + | − |
| CD1487 | + | + | − |
| CD1543a | + | + | − |
| CD1728 | Low Sensitivity Level | | |
| CD1794 | + | + | − |
| CD1897 | + | − | |
| CD1906 | + | + | − |
| CD2046 | + | + | − |
| CD2098 | + | + | − |
| CD2216 | + | + | − |
| CD2248 | Low Sensitivity Level | | |
| CD2264 | + | + | − |
| CD2274 | + | + | − |
| CD2300 | Low Sensitivity Level | | |
| CD2306 | Low Sensitivity Level | | |
| CD2309 | + | + | − |
| CD2563 | Low Sensitivity Level | | |
| CD3188 | + | + | − |
| CD3288 | + | + | − |
| CD3321 | Low Sensitivity Level | | |
| CD3367 | + | + | − |
| CD3369 | Low Sensitivity Level | | |
| CD3609 | + | + | − |
| CD3656 | Low Sensitivity Level | | |
| CD3617 | + | − | |
| CD3618 | + | − | |
| CD3635 | + | + | − |
| CD3638 | + | + | − |

The invention claimed is:

1. A method of detecting the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961 in a subject, said method comprising:
   a. obtaining a sample from said subject; and
   b. detecting whether one or more of said genes is present in the sample by contacting the sample with one or more oligonucleotide probes each capable of hybridizing to at least one of said genes and detecting binding of said one or more probes to said genes.

2. A method of detecting the presence of a product of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961 in a subject, said method comprising:
   a. obtaining a sample from said subject; and
   b. detecting whether the gene product of one or more of said genes is present in the sample by contacting the sample with one or more antibodies to said gene products and detecting binding of said one or more antibodies to said gene products.

3. A method of determining the efficacy of a therapeutic regime being used to treat a *Clostridium difficile* infection, said method comprising
   (i) performing the method of claim 1 on a sample that has been obtained from a subject being treated for a *Clostridium difficile* infection, wherein CD3609 has a coding nucleotide sequence of SEQ ID NO:36 or a sequence at least 90% identical to a contiguous sequence of SEQ ID NO:36, CD3617 has a coding nucleotide sequence of SEQ ID NO:2 or a sequence at least 90% identical to a contiguous sequence of SEQ ID NO:2, CD3618 has a coding nucleotide sequence of SEQ ID NO:3 or a sequence at least 90% identical to a contiguous sequence of SEQ ID NO:3, CD3635 has a coding nucleotide sequence of SEQ ID NO:4 or a sequence at least 90% identical to a contiguous sequence of SEQ ID NO:4, CD3638 has a coding nucleotide sequence of SEQ ID NO:5 or a sequence at least 90% identical to a contiguous sequence of SEQ ID NO:5, CD0638 has a coding nucleotide sequence of SEQ ID NO:21 or a sequence at least 90% identical to a contiguous sequence of SEQ ID NO:21, CD1424 has a coding nucleotide sequence of SEQ ID NO:22 or a sequence at least 90% identical to a contiguous sequence of SEQ ID NO:22, CD1487 has a coding nucleotide sequence of SEQ ID NO:23 or a sequence at least 90% identical to a contiguous sequence of SEQ ID NO:23, CD1543a has a coding nucleotide sequence of SEQ ID NO:24 or a sequence at least 90% identical to a contiguous sequence of SEQ ID NO:24, CD1794 has a coding nucleotide sequence of SEQ ID NO:25 or a sequence at least 90% identical to a contiguous sequence of SEQ ID NO:25, CD1906 has a coding nucleotide sequence of SEQ ID NO:26 or a sequence at least 90% identical to a contiguous sequence of SEQ ID NO:26, CD2046 has a coding nucleotide sequence of SEQ ID NO:27 or a sequence at least 90% identical to a contiguous sequence of SEQ ID NO:27, CD2098 has a coding nucleotide sequence of SEQ ID NO:28 or a sequence at least 90% identical to a contiguous sequence of SEQ ID NO:28, CD2216 has a coding nucleotide sequence of SEQ ID NO:29 or a sequence at least 90% identical to a contiguous sequence of SEQ ID NO:29, CD2264 has a coding nucleotide sequence of SEQ ID NO:30 or a sequence at least 90% identical to a contiguous sequence of SEQ ID NO:30, CD2274 has a coding nucleotide sequence of SEQ ID NO:31 or a sequence at least 90% identical to a contiguous sequence of SEQ ID NO:31, CD2309 has a coding nucleotide sequence of SEQ ID NO:32 or a sequence at least 90% identical to a contiguous sequence of SEQ ID NO:32, CD3188 has a coding nucleotide sequence of SEQ ID NO:33 or a sequence at least 90% identical to a contiguous sequence of SEQ ID NO:33, CD3288 has a coding nucleotide sequence of SEQ ID NO:34 or a sequence at least 90% identical to a contiguous sequence of SEQ ID NO:34, CD3367 has a coding nucleotide sequence of SEQ ID NO:35 or a sequence at least 90% identical to a contiguous sequence of SEQ ID NO:35, or CD2961 has a coding nucleotide sequence of SEQ ID NO:1 or a sequence at least 90% identical to a contiguous sequence of SEQ ID NO:1; and
   (ii) repeating step (i) on one or more further samples that have been obtained from the subject being treated for a *Clostridium difficile* infection, wherein a failure to detect the presence of, or a reduction in the amount of one or more of the genes in step (ii) relative to step (i) is indicative of the efficacy of the therapeutic regime.

4. The method of claim 1, wherein CD3609 has a coding nucleotide sequence of SEQ ID NO:36 or a sequence at least 90% identical to a contiguous sequence of SEQ ID NO:36, CD3617 has a coding nucleotide sequence of SEQ ID NO:2 or a sequence at least 90% identical to a contiguous sequence of SEQ ID NO:2, CD3618 has a coding nucleotide sequence of SEQ ID NO:3 or a sequence at least 90% identical to a contiguous sequence of SEQ ID NO:3, CD3635 has a coding nucleotide sequence of SEQ ID NO:4 or a sequence at least 90% identical to a contiguous sequence of SEQ ID NO:4, CD3638 has a coding nucleotide sequence of SEQ ID NO:5 or a sequence at least 90% identical to a contiguous sequence of SEQ ID NO:5, CD0638 has a coding nucleotide sequence of SEQ ID NO:21 or a sequence at least 90% identical to a contiguous sequence of SEQ ID NO:21, CD1424 has a coding nucleotide sequence of SEQ ID NO:22 or a sequence at least 90% identical to a contiguous sequence of SEQ ID NO:22, CD1487 has a coding nucleotide sequence of SEQ ID NO:23 or a sequence at least 90% identical to a contiguous sequence of SEQ ID NO:23, CD1543a has a coding nucleotide sequence of SEQ ID NO:24 or a sequence at least 90% identical to a contiguous sequence of SEQ ID NO:24, CD1794 has a coding nucleotide sequence of SEQ ID NO:25 or a sequence at least 90% identical to a contiguous sequence of SEQ ID NO:25, CD1906 has a coding nucleotide sequence of SEQ ID NO:26 or a sequence at least 90% identical to a contiguous sequence of SEQ ID NO:26, CD2046 has a coding nucleotide sequence of SEQ ID NO:27 or a sequence at least 90% identical to a contiguous sequence of SEQ ID NO:27, CD2098 has a coding nucleotide sequence of SEQ ID NO:28 or a sequence at least 90% identical to a contiguous sequence of SEQ ID NO:28, CD2216 has a coding nucleotide sequence of SEQ ID NO:29 or a sequence at least 90% identical to a contiguous sequence of SEQ ID NO:29, CD2264 has a coding nucleotide sequence of SEQ ID NO:30 or a sequence at least 90% identical to a contiguous sequence of SEQ ID NO:30, CD2274 has a coding nucleotide sequence of SEQ ID NO:31 or a sequence at least 90% identical to a contiguous sequence of SEQ ID NO:31, CD2309 has a coding nucleotide sequence of SEQ ID NO:32 or a sequence at least 90% identical to a contiguous sequence of SEQ ID NO:32, CD3188 has a coding nucleotide sequence of SEQ ID NO:33 or a sequence at least 90% identical to a contiguous sequence of SEQ ID NO:33, CD3288 has a coding nucleotide sequence of SEQ ID NO:34 or a sequence at least 90% identical to a contiguous sequence of SEQ ID NO:34, CD3367 has a coding nucleotide sequence of SEQ ID NO:35 or a sequence at least 90% identical to a contiguous sequence of SEQ ID NO:35, or CD2961 has a coding nucleotide sequence of SEQ ID NO:1 or a sequence at least 90% identical to a contiguous sequence of SEQ ID NO:1.

5. The method of claim 1, wherein the presence of one or more of said genes is detected by a primer-directed amplification reaction.

6. The method of claim 5, wherein said primer-directed amplification reaction is a polymerase chain reaction.

7. A method of detecting the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961 in an environmental sample, said method comprising contacting the sample with one or more oligonucleotide probes each capable of hybridizing to at least one of said genes and detecting binding of said one or more probes to said genes.

8. A method of detecting the presence of one or more genes selected from the group consisting of CD3609, CD3617, CD3618, CD3635, CD3638, CD0638, CD1424, CD1487, CD1543a, CD1794, CD1906, CD2046, CD2098, CD2216, CD2264, CD2274, CD2309, CD3188, CD3288, CD3367 and CD2961 in an environmental sample, said method comprising contacting the sample with one or more antibodies to said gene products and detecting binding of said one or more antibodies to said gene products.

9. The method of claim 1, wherein step b. comprises:
detecting whether one or more of said genes is present in the sample by contacting the sample with one or more oligonucleotide pairs selected from the group consisting of:
(i) a forward primer comprising SEQ ID NO: 11 and a reverse primer comprising SEQ ID NO: 12,
(ii) a forward primer comprising SEQ ID NO: 13 and a reverse primer comprising SEQ ID NO: 14,
(iii) a forward primer comprising SEQ ID NO: 15 and a reverse primer comprising SEQ ID NO: 16,
(iv) a forward primer comprising SEQ ID NO: 17 and a reverse primer comprising SEQ ID NO: 18,
(v) a forward primer comprising SEQ ID NO: 19 and a reverse primer comprising SEQ ID NO: 20,
(vi) a forward primer comprising SEQ ID NO: 37 and a reverse primer comprising SEQ ID NO: 38,
(vii) a forward primer comprising SEQ ID NO: 39 and a reverse primer comprising SEQ ID NO: 40,
(viii) a forward primer comprising SEQ ID NO: 41 and a reverse primer comprising SEQ ID NO: 42,
(ix) a forward primer comprising SEQ ID NO: 43 and a reverse primer comprising SEQ ID NO: 44,
(x) a forward primer comprising SEQ ID NO: 45 and a reverse primer comprising SEQ ID NO: 46,
(xi) a forward primer comprising SEQ ID NO: 47 and a reverse primer comprising SEQ ID NO: 48,
(xii) a forward primer comprising SEQ ID NO: 49 and a reverse primer comprising SEQ ID NO: 50,
(xiii) a forward primer comprising SEQ ID NO: 51 and a reverse primer comprising SEQ ID NO: 52,
(xiv) a forward primer comprising SEQ ID NO: 53 and a reverse primer comprising SEQ ID NO: 54,
(xv) a forward primer comprising SEQ ID NO: 55 and a reverse primer comprising SEQ ID NO: 56,
(xvi) a forward primer comprising SEQ ID NO: 57 and a reverse primer comprising SEQ ID NO: 58,
(xvii) a forward primer comprising SEQ ID NO: 59 and a reverse primer comprising SEQ ID NO: 60,
(xviii) a forward primer comprising SEQ ID NO: 61 and a reverse primer comprising SEQ ID NO: 62,
(xix) a forward primer comprising SEQ ID NO: 63 and a reverse primer comprising SEQ ID NO: 64,
(xx) a forward primer comprising SEQ ID NO: 65 and a reverse primer comprising SEQ ID NO: 66, and
(xxi) a forward primer comprising SEQ ID NO: 67 and a reverse primer comprising SEQ ID NO: 68,
amplifying said one or more genes, and
detecting a resultant amplified gene product.

10. The method of claim 7, wherein said method comprises contacting the sample with one or more oligonucleotide pairs selected from the group consisting of:
(i) a forward primer comprising SEQ ID NO: 11 and a reverse primer comprising SEQ ID NO: 12,
(ii) a forward primer comprising SEQ ID NO: 13 and a reverse primer comprising SEQ ID NO: 14,
(iii) a forward primer comprising SEQ ID NO: 15 and a reverse primer comprising SEQ ID NO: 16,
(iv) a forward primer comprising SEQ ID NO: 17 and a reverse primer comprising SEQ ID NO: 18,
(v) a forward primer comprising SEQ ID NO: 19 and a reverse primer comprising SEQ ID NO: 20,
(vi) a forward primer comprising SEQ ID NO: 37 and a reverse primer comprising SEQ ID NO: 38,
(vii) a forward primer comprising SEQ ID NO: 39 and a reverse primer comprising SEQ ID NO: 40, (viii) a forward primer comprising SEQ ID NO: 41 and a reverse primer comprising SEQ ID NO: 42,
(ix) a forward primer comprising SEQ ID NO: 43 and a reverse primer comprising SEQ ID NO: 44,
(x) a forward primer comprising SEQ ID NO: 45 and a reverse primer comprising SEQ ID NO: 46,
(xi) a forward primer comprising SEQ ID NO: 47 and a reverse primer comprising SEQ ID NO: 48,
(xii) a forward primer comprising SEQ ID NO: 49 and a reverse primer comprising SEQ ID NO: 50,
(xiii) a forward primer comprising SEQ ID NO: 51 and a reverse primer comprising SEQ ID NO: 52,
(xiv) a forward primer comprising SEQ ID NO: 53 and a reverse primer comprising SEQ ID NO: 54,
(xv) a forward primer comprising SEQ ID NO: 55 and a reverse primer comprising SEQ ID NO: 56,
(xvi) a forward primer comprising SEQ ID NO: 57 and a reverse primer comprising SEQ ID NO: 58,
(xvii) a forward primer comprising SEQ ID NO: 59 and a reverse primer comprising SEQ ID NO: 60,
(xviii) a forward primer comprising SEQ ID NO: 61 and a reverse primer comprising SEQ ID NO: 62,
(xix) a forward primer comprising SEQ ID NO: 63 and a reverse primer comprising SEQ ID NO: 64,
(xx) a forward primer comprising SEQ ID NO: 65 and a reverse primer comprising SEQ ID NO: 66, and
(xxi) a forward primer comprising SEQ ID NO: 67 and a reverse primer comprising SEQ ID NO: 68,
amplifying said one or more genes, and
detecting a resultant amplified gene product.

* * * * *

SEQUENCE LISTING

<160> NUMBER OF SEQ ID NOS: 162

<210> SEQ ID NO 1
<211> LENGTH: 312
<212> TYPE: DNA

<213> ORGANISM: Clostridium difficile

<400> SEQUENCE: 1

| | |
|---|---|
| atggcttttg aaataataaa aagcattgtt gaggcagagc agacagcaga cagtatcaaa | 60 |
| gtaaaagctg ttactgatgc agagtctatc agagctgatg ctgtaaacaa atgtgaaagc | 120 |
| atatttgctg atgtaaaaaa acaagcaaag cttatggaag aaactcttat tgagaaggca | 180 |
| gtcaccgaca gtagagcaga ggttgataaa atcttagcta atgctaaaag tgaatgtctg | 240 |
| aaaattgaaa aaactgctga agaagaaaa agtaaggcta ttgaagcggt tattggaaag | 300 |
| gtagtgagat aa | 312 |

<210> SEQ ID NO 2
<211> LENGTH: 918
<212> TYPE: DNA
<213> ORGANISM: Clostridium difficile

<400> SEQUENCE: 2

| | |
|---|---|
| atggtaaata tgaatattat agaaattcgc tcagataaaa tatacaagaa gataatggat | 60 |
| gcaccaataa acaaaaaaga agatatatac agatatgaat aatgaagcc ttttgaattt | 120 |
| aagtggaagt gtatgaatgt tccaatagtt gctagacaga aaggtggata tgatgtaatt | 180 |
| atagcaagtg aaatgttagg ggttttatcg cctaaggata ttgatgaaaa gcaaaaaaag | 240 |
| aatataaatg tgttatctgc tgataaaatt tgggccactt gtaaagaaac catagaaaac | 300 |
| tctataaatg cttttataaa agagggtat gatttaaaca ttaaggacta taaatattca | 360 |
| atattattgg cgaatccaaa tagtccttat acaatattaa gtgatggata ctgggggtgat | 420 |
| ggtgggattc ctggatatat atttctatca ttggttccta tgaatatac tatcaataga | 480 |
| ttaccagtat taatagcaca tgaatgtaat cacaatatta gatttcagtt tatagagtgg | 540 |
| aataataata taacattaga agaaatgatg ataaatgaag gtcttgcaga aaattttgca | 600 |
| acatggatgt ttggagagga aatgttagga ccttgggtca gtagaacaga tatcgaaaca | 660 |
| ttaaatactt atataaagcc aataataaaa agtgctttaa agaaactgg atttcaaaat | 720 |
| ataacatctt atctttatgg tgatgatata gctaaaatgc aaggatattt tccagtaggg | 780 |
| ttgcccttatt gtgcaggata tgcttgtgga tattatatga ttaagtatta tttagaaaag | 840 |
| acaaataaat caataatcga agcgacttta ttgcccttata gtgagataat cgaagcagta | 900 |
| aaagagttttt gggaataa | 918 |

<210> SEQ ID NO 3
<211> LENGTH: 384
<212> TYPE: DNA
<213> ORGANISM: Clostridium difficile

<400> SEQUENCE: 3

| | |
|---|---|
| ttggtcatgc taactccata tttaatattt aatggtactt gtgaaaaagc atttaattt | 60 |
| tatgctgagg ctttcggagg aggaaaaact atatttgcgc gattagacag caatccaaac | 120 |
| aatcctgtta tgcacgcaag tgttactttc acaaaatacg aaggttgtat aatgggtgcg | 180 |
| gatacagaca agcctgttgt aatttctggc atggcgattt gtgttgttct accatctcga | 240 |
| gaagcgatag aagaaatatc tgtaaaactt gccgaaggtg gtacacttgt acaagaattt | 300 |
| ttaccacacc caccaccaca tcaaaatgat ggcgctgctg aagtacttga taggtatggg | 360 |
| tatacttggt atttaagtac atag | 384 |

<210> SEQ ID NO 4
<211> LENGTH: 855
<212> TYPE: DNA
<213> ORGANISM: Clostridium difficile

<400> SEQUENCE: 4

| | | | | | |
|---|---|---|---|---|---|
| atggctatgg | gttttgaatt | taaaataatg | agaagtttaa | tatatgtagg | acttgccaag | 60 |
| gaagaatata | gacctaagct | aatggactgg | ttatatcgtc | accatattcc | agatagtatt | 120 |
| agcacttttg | gaccatattg | tactaaatat | gccttttatc | aagcatatcc | tacaccaaat | 180 |
| gaaggtgagc | gttttggtgc | acgtaagatg | caactaacag | aacattattg | gcttgtagat | 240 |
| gaacatatgc | ctgagatggc | aaatagaatt | atgacagaat | atatgcctat | ggatgttcta | 300 |
| cgttggcaag | ggtgtatacc | agatgtagaa | aataaaaggg | ttcatgaaaa | tgcagaaagt | 360 |
| ggagatgcag | gacgtgcagt | aggtggagat | aatggatgtc | caccatttat | atttgccttt | 420 |
| gttccaataa | actgggaaga | agactttaga | ggaaaaggac | gtactgtaca | agatggacca | 480 |
| aactatcgtt | ggcaatttat | gattaagtat | ccagatggta | tctctaaaga | agaaggagaa | 540 |
| aaatggttct | atgatgaggt | agtgccatac | tttacaaact | gttgctatgt | taatcgtttt | 600 |
| gtcagtagta | aaataatgat | taattatgga | gcaactgctt | ttgaccgtgt | atcagaacta | 660 |
| tggtttgaag | gggaagaaga | atggtataaa | gctgtggttg | aagaaacaaa | gtcgtttatt | 720 |
| aaaaaaccag | aatgggcaca | agaagaggag | ttcccatatt | taaaaccaca | attcaatatc | 780 |
| gcatcagtat | tcttaggtga | tatagcaact | atggatgcat | actcacagta | tcgtggatat | 840 |
| ataccaatga | gataa | | | | | 855 |

<210> SEQ ID NO 5
<211> LENGTH: 1389
<212> TYPE: DNA
<213> ORGANISM: Clostridium difficile

<400> SEQUENCE: 5

| | | | | | |
|---|---|---|---|---|---|
| atggaagata | aattttatgc | aaaaggcaac | ggaaataacg | gatatattaa | aaatcttgaa | 60 |
| gtttgttcct | ttaataactt | agatggaact | tgtggaatgt | ttcaaatggc | tctgtacaaa | 120 |
| agagatgaaa | aatactattt | tatggatgc | tgttttggag | gaaataaaaa | aaatggagta | 180 |
| atgattagcg | atattacaga | cccttataat | ccacaattta | taaaacattt | tcaaatgtta | 240 |
| gaccctaaag | agtatcctac | aacaacaact | cccaaaattc | aaatagcaga | tgatttaatg | 300 |
| atagtagcaa | tgagttgtgg | aagtggacca | ggagcacttg | ttgaccaagc | taaattagca | 360 |
| aatattaagt | gtgaagcagg | aattagaata | tacagtttaa | aagaagaccc | tttaaatcct | 420 |
| aagttttttag | gatattggga | ttgtggctta | aagcatgtaa | tgggtgttca | tagatttatg | 480 |
| tacaatggtg | aagatatgt | acatttatca | agtgattgtg | ttggctttga | aggtctgatt | 540 |
| tataggtca | tagatataat | aaatcctact | aatccagtgg | aaataggtaa | atggtggaga | 600 |
| ccagaccaat | atgcagatgg | atatccaaat | agaacttttg | atgcaggagc | acctcattgc | 660 |
| ccagaattta | tggataaagg | atggcttcat | ggacctccat | ttgtaagaga | cggaaaagca | 720 |
| tattgtggtt | atggaggagc | tggtttagtt | gtattagatg | ttgaagattt | aacaagacca | 780 |
| agatgcttag | gtgaattgcc | atttacgcct | gcatttccta | gtagacttgc | aggtgcaaga | 840 |
| actcatacag | cattaccatt | gccaggaaga | gatttagtcg | ttgttcaaaa | tgagggagaa | 900 |
| agattccagt | tctttaaacc | agataacatt | acagatgttc | aagctatgaa | taatatacat | 960 |
| atggttgatg | ttagtgaccc | aacaaaacca | acattaattg | ctcaatttcc | atatcctgaa | 1020 |

```
gttccaaaag atttccctta tcctaacttt aatgttgcgg gattaggaaa accagggcca    1080
tttggcccac ataatcttca tgaaccaatg gataataagc catggttaga gcaaagagga    1140
gatagagtat attgctgtta tttccatgca gggctaaggg tttatgatgt atcagaccca    1200
tattatatca aagagctagc atattttata ccaccaaatc caaataaaac accagaagaa    1260
tcttatttcc caggattccc aggaccacgc ttggcagtaa cagaagatct tatcgttgat    1320
gatagaggct acatcatcat agatgcttta gatgatggat tctatatatt aaaaatgaaa    1380
gatgattaa                                                           1389
```

<210> SEQ ID NO 6
<211> LENGTH: 103
<212> TYPE: PRT
<213> ORGANISM: Clostridium difficile

<400> SEQUENCE: 6

```
Met Ala Phe Glu Ile Ile Lys Ser Ile Val Glu Ala Glu Gln Thr Ala
1               5                   10                  15

Asp Ser Ile Lys Val Lys Ala Val Thr Asp Ala Glu Ser Ile Arg Ala
            20                  25                  30

Asp Ala Val Asn Lys Cys Glu Ser Ile Phe Ala Asp Val Lys Lys Gln
        35                  40                  45

Ala Lys Leu Met Glu Glu Thr Leu Ile Glu Lys Ala Val Thr Asp Ser
    50                  55                  60

Arg Ala Glu Val Asp Lys Ile Leu Ala Asn Ala Lys Ser Glu Cys Leu
65                  70                  75                  80

Lys Ile Glu Lys Thr Ala Glu Glu Arg Lys Ser Lys Ala Ile Glu Ala
                85                  90                  95

Val Ile Gly Lys Val Val Arg
            100
```

<210> SEQ ID NO 7
<211> LENGTH: 303
<212> TYPE: PRT
<213> ORGANISM: Clostridium difficile

<400> SEQUENCE: 7

```
Met Val Asn Met Asn Ile Ile Glu Ile Arg Ser Asp Lys Ile Tyr Lys
1               5                   10                  15

Lys Ile Met Asp Ala Pro Ile Asn Lys Lys Glu Asp Ile Tyr Arg Tyr
            20                  25                  30

Glu Leu Met Lys Pro Phe Glu Phe Lys Trp Lys Cys Met Asn Val Pro
        35                  40                  45

Ile Val Ala Arg Gln Lys Gly Gly Tyr Asp Val Ile Ile Ala Ser Glu
    50                  55                  60

Met Leu Gly Val Leu Ser Pro Lys Asp Ile Asp Glu Lys Gln Lys Lys
65                  70                  75                  80

Asn Ile Asn Val Leu Ser Ala Asp Lys Ile Trp Ala Thr Cys Lys Glu
                85                  90                  95

Thr Ile Glu Asn Ser Ile Asn Ala Phe Ile Lys Glu Gly Tyr Asp Leu
            100                 105                 110

Asn Ile Lys Asp Tyr Lys Tyr Ser Ile Leu Leu Ala Asn Pro Asn Pro
        115                 120                 125

Tyr Thr Ile Leu Ser Asp Gly Tyr Trp Gly Asp Gly Ile Pro Gly
    130                 135                 140

Tyr Ile Phe Leu Ser Leu Val Pro Asn Glu Tyr Thr Ile Asn Arg Leu
```

```
            145                 150                 155                 160
Pro Val Leu Ile Ala His Glu Cys Asn His Asn Ile Arg Phe Gln Phe
                165                 170                 175

Ile Glu Trp Asn Asn Asn Ile Thr Leu Glu Met Met Ile Asn Glu
            180                 185                 190

Gly Leu Ala Glu Asn Phe Ala Thr Trp Met Phe Gly Glu Met Leu
        195                 200                 205

Gly Pro Trp Val Ser Arg Thr Asp Ile Glu Thr Leu Asn Thr Tyr Ile
    210                 215                 220

Lys Pro Ile Ile Lys Ser Ala Leu Lys Glu Thr Gly Phe Gln Asn Ile
225                 230                 235                 240

Thr Ser Tyr Leu Tyr Gly Asp Asp Ile Ala Lys Met Gln Gly Phe Pro
                245                 250                 255

Val Gly Leu Pro Tyr Cys Ala Gly Tyr Ala Cys Gly Tyr Tyr Met Ile
            260                 265                 270

Lys Tyr Tyr Leu Glu Lys Thr Asn Lys Ser Ile Ile Glu Ala Thr Leu
        275                 280                 285

Leu Pro Tyr Ser Glu Ile Ile Glu Ala Val Lys Glu Phe Trp Glu
    290                 295                 300
```

<210> SEQ ID NO 8
<211> LENGTH: 127
<212> TYPE: PRT
<213> ORGANISM: Clostridium difficile

<400> SEQUENCE: 8

```
Met Val Met Leu Thr Pro Tyr Leu Ile Phe Asn Gly Thr Cys Glu Lys
1               5                   10                  15

Ala Phe Asn Phe Tyr Ala Glu Ala Phe Gly Gly Gly Lys Thr Ile Phe
            20                  25                  30

Ala Arg Leu Asp Ser Asn Pro Asn Pro Val Met His Ala Ser Val
        35                  40                  45

Thr Phe Thr Lys Tyr Glu Gly Cys Ile Met Gly Ala Asp Thr Asp Lys
    50                  55                  60

Pro Val Val Ile Ser Gly Met Ala Ile Cys Val Val Leu Pro Ser Arg
65                  70                  75                  80

Glu Ala Ile Glu Glu Ile Ser Val Lys Leu Ala Glu Gly Gly Thr Leu
                85                  90                  95

Val Gln Glu Phe Leu Pro His Pro Pro His Gln Asn Asp Gly Ala
            100                 105                 110

Ala Glu Val Leu Asp Arg Tyr Gly Tyr Thr Trp Tyr Leu Ser Thr
        115                 120                 125
```

<210> SEQ ID NO 9
<211> LENGTH: 282
<212> TYPE: PRT
<213> ORGANISM: Clostridium difficile

<400> SEQUENCE: 9

```
Met Ala Met Gly Phe Glu Phe Lys Ile Met Arg Ser Leu Ile Tyr Val
1               5                   10                  15

Gly Leu Ala Lys Glu Glu Tyr Arg Pro Lys Leu Met Asp Trp Leu Tyr
            20                  25                  30

Arg His His Ile Pro Asp Ser Ile Ser Thr Phe Gly Pro Tyr Cys Thr
        35                  40                  45

Lys Tyr Ala Phe Tyr Gln Ala Tyr Pro Thr Pro Asn Glu Gly Glu Arg
```

-continued

```
    50                  55                  60

Phe Gly Ala Arg Lys Met Gln Leu Thr Glu His Tyr Trp Leu Val Asp
65                  70                  75                  80

Glu His Met Pro Glu Met Ala Asn Arg Ile Met Thr Glu Tyr Met Pro
                85                  90                  95

Met Asp Val Leu Arg Trp Gln Gly Cys Ile Pro Asp Val Glu Asn Lys
            100                 105                 110

Arg Val His Glu Asn Ala Glu Ser Gly Asp Ala Gly Arg Ala Val Gly
        115                 120                 125

Asp Asn Gly Cys Pro Pro Phe Ile Phe Ala Phe Val Pro Ile Asn Trp
    130                 135                 140

Glu Glu Asp Phe Arg Gly Lys Gly Arg Thr Val Gln Asp Gly Pro Asn
145                 150                 155                 160

Tyr Arg Trp Gln Phe Met Ile Lys Tyr Pro Asp Gly Ile Ser Lys Glu
                165                 170                 175

Glu Gly Glu Lys Trp Phe Tyr Asp Glu Val Val Pro Tyr Phe Thr Asn
            180                 185                 190

Cys Cys Tyr Val Asn Arg Phe Val Ser Ser Lys Ile Met Ile Asn Tyr
        195                 200                 205

Gly Ala Thr Ala Phe Asp Arg Val Ser Glu Leu Trp Phe Glu Gly Glu
    210                 215                 220

Glu Glu Trp Tyr Lys Ala Val Val Glu Glu Thr Lys Ser Phe Ile Lys
225                 230                 235                 240

Lys Pro Glu Trp Ala Gln Glu Glu Glu Phe Pro Tyr Leu Lys Gln Phe
                245                 250                 255

Asn Ile Ala Ser Val Phe Leu Gly Asp Ile Ala Thr Met Asp Ala Tyr
            260                 265                 270

Ser Gln Tyr Arg Gly Tyr Ile Pro Met Arg
        275                 280

<210> SEQ ID NO 10
<211> LENGTH: 459
<212> TYPE: PRT
<213> ORGANISM: Clostridium difficile

<400> SEQUENCE: 10

Met Glu Asp Lys Phe Tyr Ala Lys Gly Asn Gly Asn Asn Gly Tyr Ile
1               5                   10                  15

Lys Asn Leu Glu Val Cys Ser Phe Asn Asn Leu Asp Gly Thr Cys Gly
            20                  25                  30

Met Phe Gln Met Ala Leu Tyr Lys Arg Asp Glu Lys Tyr Tyr Leu Tyr
        35                  40                  45

Gly Cys Cys Phe Gly Gly Asn Lys Lys Asn Gly Val Met Ile Ser Asp
    50                  55                  60

Ile Thr Asp Pro Tyr Asn Pro Gln Phe Ile Lys His Phe Gln Met Leu
65                  70                  75                  80

Asp Pro Lys Glu Tyr Pro Thr Thr Thr Thr Pro Lys Ile Gln Ile Ala
                85                  90                  95

Asp Asp Leu Met Ile Val Ala Met Ser Cys Gly Ser Gly Pro Gly Ala
            100                 105                 110

Leu Val Asp Gln Ala Lys Leu Ala Asn Ile Lys Cys Glu Ala Gly Arg
        115                 120                 125

Ile Tyr Ser Leu Lys Glu Asp Pro Leu Asn Pro Lys Phe Leu Gly Tyr
    130                 135                 140
```

-continued

```
Trp Asp Cys Gly Leu Lys His Val Met Gly Val His Arg Phe Met Tyr
145                 150                 155                 160

Asn Gly Gly Arg Tyr Val His Leu Ser Ser Asp Cys Val Gly Phe Glu
            165                 170                 175

Gly Leu Ile Tyr Arg Val Ile Asp Ile Ile Asn Pro Thr Asn Pro Val
        180                 185                 190

Glu Ile Gly Lys Trp Trp Arg Pro Asp Gln Tyr Ala Asp Gly Tyr Pro
    195                 200                 205

Asn Arg Thr Phe Asp Ala Gly Ala Pro His Cys Pro Glu Phe Met Asp
210                 215                 220

Lys Gly Trp Leu His Gly Pro Pro Phe Val Arg Asp Gly Lys Ala Tyr
225                 230                 235                 240

Cys Gly Tyr Gly Gly Ala Gly Leu Val Val Leu Asp Val Glu Leu Thr
            245                 250                 255

Arg Pro Arg Cys Leu Gly Glu Leu Pro Phe Thr Pro Ala Phe Ser Ser
        260                 265                 270

Arg Leu Ala Gly Ala Arg Thr His Thr Ala Leu Pro Leu Pro Gly Arg
    275                 280                 285

Asp Leu Val Val Val Gln Asn Glu Gly Glu Arg Phe Gln Phe Phe Lys
290                 295                 300

Pro Asp Asn Ile Thr Asp Val Gln Ala Met Asn Asn Ile His Met Val
305                 310                 315                 320

Asp Val Ser Asp Pro Thr Lys Pro Thr Leu Ile Ala Gln Phe Pro Tyr
            325                 330                 335

Pro Glu Val Pro Lys Asp Phe Pro Tyr Pro Asn Phe Asn Val Ala Gly
        340                 345                 350

Leu Gly Lys Pro Gly Pro Phe Gly Pro His Asn Leu His Glu Pro Met
    355                 360                 365

Asp Asn Lys Pro Trp Leu Glu Gln Arg Gly Asp Arg Val Cys Cys Tyr
370                 375                 380

Phe His Ala Gly Leu Arg Val Tyr Asp Val Ser Asp Pro Tyr Tyr Ile
385                 390                 395                 400

Lys Glu Leu Ala Tyr Phe Ile Pro Pro Asn Pro Asn Lys Thr Pro Glu
            405                 410                 415

Glu Ser Tyr Phe Pro Gly Phe Pro Gly Pro Arg Leu Ala Val Thr Glu
        420                 425                 430

Asp Leu Ile Val Asp Asp Arg Gly Tyr Ile Ile Ile Asp Ala Leu Asp
    435                 440                 445

Asp Gly Phe Tyr Ile Leu Lys Met Lys Asp Asp
450                 455
```

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agaaggcagt caccgacagt                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cctttccaat aaccgcttca                                                    20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gatggatact ggggtgatgg                                                    20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aaggcaataa agtcgcttcg                                                    20

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
tttaatggta cttgtgaaaa agcat                                              25

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gccatcattt tgatgtggtg                                                    20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
catatgcctg agatggcaaa                                                    20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cttgtgccca ttctggtttt                                                    20

<210> SEQ ID NO 19

-continued

```
<211> LENGTH: 20
<212> TYPE: DNA
<213> ORGANISM: Artificial Sequence
<220> FEATURE:
<223> OTHER INFORMATION: primer
<400> SEQUENCE: 19
ggatgctgtt ttggaggaaa 20

<210> SEQ ID NO 20
<211> LENGTH: 20
<212> TYPE: DNA
<213> ORGANISM: Artificial Sequence
<220> FEATURE:
<223> OTHER INFORMATION: primer
<400> SEQUENCE: 20
aaattctggg caatgaggtg 20

<210> SEQ ID NO 21
<211> LENGTH: 201
<212> TYPE: DNA
<213> ORGANISM: Clostridium difficile
<400> SEQUENCE: 21
ttgtttattt tgaattttgg aggattaatt atggattcaa ataataatac tataaaatca 60
actgttaaaa agggtatttc ttttggttct tgtttagcaa tgattatttc ttatactgca 120
tggaaatcta ttccatgggc tatttttcat ggcttaatga gttggatata tgtactttat 180
tattgggtta agtatgcata g 201

<210> SEQ ID NO 22
<211> LENGTH: 177
<212> TYPE: DNA
<213> ORGANISM: Clostridium difficile
<400> SEQUENCE: 22
atgtttagag atgaaatgga taaatgtaca cacatgttaa ctgcttatat tagtagttta 60
tatgattatt gtgattttat agatacacag ctagatgatt ttatactaga gtacggagaa 120
aatgtagtag aatcttgttt acatcaagtg atggtattgg taagtaagta taattaa 177

<210> SEQ ID NO 23
<211> LENGTH: 468
<212> TYPE: DNA
<213> ORGANISM: Clostridium difficile
<400> SEQUENCE: 23
atggaaaatg atactattaa ggctgatgat attctcaatt attgtctatc aaacttagat 60
gatgttgtac taatggatag ttggggggaa cgagcaattt actacaatcc taatggtgtt 120
ttaaagcgag ggtatatgt tcttaccatt aaggaaaaag acagtaataa tgataaaggt 180
tcgttagtta gtcgtccaaa tgtataccgt gtgaatatag gattaaaaaa agaaactttt 240
attgaaatgt ttggatatat tccaaagcgt ccaggtgtag gtcaaatagt tgatatggat 300
tttgatttta caaaattgga cacaatcatg ccacatccta tctactcatg gatgggatgg 360
atatgcgtcc taagccctac tgaaaagaca tttgagaact ttaaaacttt aataggagaa 420
tcttacaatt ttgcaaaaca aaaatttaaa aagagaaaaa acaagtaa 468

<210> SEQ ID NO 24
<211> LENGTH: 210
```

```
<212> TYPE: DNA
<213> ORGANISM: Clostridium difficile

<400> SEQUENCE: 24
atgcgagaag aaaaaagtaa tgaaaagtat gattgttatt ggtgtaatca agagaataat      60
ttctgtgtag aaataaaaga taatatagtc atgatagatg atggcactgg tacgttaaaa     120
caagccgttt tcatagggta taaacaaatc caaattaatt taaactgttc acattgtcaa     180
aacttaaata gaataaaatt aaatttgtag                                      210

<210> SEQ ID NO 25
<211> LENGTH: 246
<212> TYPE: DNA
<213> ORGANISM: Clostridium difficile

<400> SEQUENCE: 25
ttgtttatag atgaagaatt agaaggttat atattaacat gtaaaatatc tgaagacttt      60
aaaaatatac ctgaatatag tgatgaagag ttttatgtta cagtctataa agatgaaagt     120
tctgactctg gtactatgc tttattagaa aataagaag aaagagttgt atgggatgga      180
gaagttgttg ccaataatat ttttaataac ctttggattg tagtaaataa ggttaaaact     240
ggataa                                                                 246

<210> SEQ ID NO 26
<211> LENGTH: 183
<212> TYPE: DNA
<213> ORGANISM: Clostridium difficile

<400> SEQUENCE: 26
ttgcatatgg aaatcaatgt tatagaaatt ttccctaaag ataaagctaa acttaataaa      60
atagaaatgg ataaagctag ttggtttgta aatataataa gtaaaaaata tcctaaagaa     120
gctttaaatg aagcatttag tactttagaa aaagaattaa atataagtaa agctaataca     180
taa                                                                    183

<210> SEQ ID NO 27
<211> LENGTH: 294
<212> TYPE: DNA
<213> ORGANISM: Clostridium difficile

<400> SEQUENCE: 27
gtggatgaaa tgcttgtata taataaaagt ttttatccta atgcatatat tccaagatta      60 gattttcaa aaataaaaaa acagttaaaa ttgatagata atgacctgtc agattttgga     120
agcatatgta taatagaaaa agaacattat acgataagtg taaacagtat aggtgaaata     180
aatgtgtact atgatttaga gtacgaaaat aaggtgtata aatagtttta tgagattgaa     240
aagttattta atctcaagt tggaaggttt agcatatcta catacagaaa ttga            294

<210> SEQ ID NO 28
<211> LENGTH: 312
<212> TYPE: DNA
<213> ORGANISM: Clostridium difficile

<400> SEQUENCE: 28
ttggctggta atctaaataa tatgagagca gtaaataatt ttagaggaga taagaacatt      60
ttagaatgtt tagtcagctt tgagggtcgt tcaataagtc agagaaaagt aagggtattt     120
tttaaagaaa aacaaaatca aatagaaatt gattttgcag aagaggaaat ttctaaattg     180
```

```
gttgaaaatg ttgttttaaa tacatcatat caagaaatgt tatatgatga aatagagaaa      240
caactggaaa ttgattgtat aggtacttgg atgatattat ctaaattaaa agatggtagt      300
agagttcact ga                                                          312

<210> SEQ ID NO 29
<211> LENGTH: 678
<212> TYPE: DNA
<213> ORGANISM: Clostridium difficile

<400> SEQUENCE: 29
atgattgtga ttgaaggtag cgataaattt aagattgcaa agagaatatat tgatgtagaa       60 tatactcttt ttagcaaagt aacttttagg tatgaaaagt tgaaatttaa agataatgct      120
gaattggaaa aaattaagat gtttaaatat aaaaatggct acatccctaa taaattaaac      180
cttctttttg gatatggatt ctcttcttat aaaaagcaaa taattagaga aactgtagat      240
actttaagat tgacagaaat tttttcaagc gagaacatag aagatattaa atttataaaa      300
gatggtacaa aaaattaga aattagcata gagaaagttg tgaaatttaa acgtcgaaaa      360
aaagaaaatt atgtttgttg ctattgccct gatatgtata gggacataaa actcgacaaa      420
gaatctatca ataagatata caacagaaaa ataaaaatag aagagaagt taatatttt      480 gaagatgagg atgttataat aaacaaaaaa gtattgaagt tccaaagtc ttggacaaag      540 aatatgcaaa atattggtt aagtgaaaat aagtatccca tacattctac tgtaattgat      600
gatgatagat ataaatgttg taatgtacaa tatacaaaaa atagagtgat aatattatat      660
tacatatata accattaa                                                    678

<210> SEQ ID NO 30
<211> LENGTH: 1044
<212> TYPE: DNA
<213> ORGANISM: Clostridium difficile

<400> SEQUENCE: 30
gtgttaaaaa agtggtttgg tattgtgaaa aaaagacaaa aaagtgagtc agtaaaagaa       60
gaaggtgaag taatattaaa aaacgaaaaa atattatctg aagaaaagtt gatagatgaa      120 gaggagttg tagttaatat tgataatgaa atattaacta agtagaagt agtaaatgat      180 gacaatgaaa tagaagaaaa aataatagaa gaagattggt taattagtga aaataccata      240
aaattagatg ataaagaagc aattattaat gataaaaaca tagaattatg taaaaaagaa      300
gttcaagttg aaggtgaaaa aatagattta aataagtttg aaggacttga ccaaaatgaa      360
aattataatc tagaaaaaaa tgttattgaa gaaaagaag taagtgaatg tttgacagaa      420
gaagatttag agtacataaa agaaattaaa ataaaaagag gaaaagtat aaaagctata      480 aacttgtata ctaaagaaga gtgggttttt gacactcata tacagtgtag taaaaaactc      540
aaagttccat tagggtacat aagagaaaat ttaaaatatg gatatatgga ttactttgga      600
gatgcaataa attatttaag tgaagtatta aatatagatg aatactgcaa aagtgaatgg      660
agctatctcg ataatagcaa atctccatct gagatattta atattctaaa caataaaata      720
tttagtataa ggcttttctaa tgaaaaaaga atgaaatttt tgacaaatga taaattgaa      780 gcattaaaaa tgaattatag atttgaatgt attgatgaag aatatgatga atattttaaa      840
aaatataagt ctataatcaa aagaggtgga agaaaaaaag ttgaattagt aaataaaaaa      900
ggtgacattt tagaaatatt taagtctta gaagaatgtg ccatttattt gcaaaaggaa      960
aagaatgaag ttatacaaat gttaaaatat ggagatacaa aagtaggaag aaactttata     1020
```
aggtatagtt tgagaagtat ttaa						1044

<210> SEQ ID NO 31
<211> LENGTH: 1254
<212> TYPE: DNA
<213> ORGANISM: Clostridium difficile

<400> SEQUENCE: 31

| | | | | | |
|---|---|---|---|---|---|
| atggatttaa | gtggcatatt | taaatactat | tgtaaagagt | gtgaaaatac | atggaataat | 60 |
| tcgagtgttg | aattatttga | gaatatagaa | acgtatagta | aagattcaca | aaaaaagagg | 120 |
| gaaaaagaat | tagataaatt | gctaaataca | atatcagttc | atttagagag | gtatccaagt | 180 |
| gatgctgtat | tgagaaaaat | gtgggtaaaa | aagggcgagg | ttttcttaca | aaagacattg | 240 |
| gaaaaagaaa | atattttaa | gttagaaaaa | atggatgtag | aggatagaaa | aaaattttta | 300 |
| gatataacaa | aacagtttat | tagagatgct | agaaaatttg | atgatgattt | acctataggt | 360 |
| gatattatgc | aagctatgag | gaatgtatgg | atttcaaatg | cattacaatt | attatttggt | 420 |
| aaagaagtat | attattcaaa | agctaactt | gcatatagta | tgttatatcc | atatactgat | 480 |
| aattatttag | acaatacaaa | tatagataaa | atgataaga | ttttatttaa | taactggtta | 540 |
| gaaaaaaggc | tcctgggaga | acacattaaa | tctaaggatt | atcatgaaag | taaagtatct | 600 |
| caaatgatag | attatattga | agtgtatac | cctagagaaa | agtttacaga | agtttatgaa | 660 |
| tcgttattat | taatatttaa | aagtcaagta | aatagtttaa | aacaacatgg | taaggaaaat | 720 |
| catttgtgta | aagaagattt | attatccatt | tctattgaaa | aaggaggttc | atccgtttta | 780 |
| gtagatggat | atttaataag | tggattgatg | acaaaggaag | aaatagagtt | ttgtatagga | 840 |
| tatggatttt | tattacaaat | atctgatgat | ttacaagata | taaagaaga | tttaaaatac | 900 |
| aaccataaaa | ctattattac | agagatgtca | aaagagggta | ctttagataa | agttgtaaat | 960 |
| aaactaataa | attttactat | tgagttaata | gatagtttta | aaattaataa | taaaaataaa | 1020 |
| tctgtaataa | ctatgataaa | gaatgattgc | ttaatgttaa | ttttattttc | tgtagtttat | 1080 |
| aatgctgaat | ttttttctgt | aggatatata | aagaagtag | agaaatttat | tccatataca | 1140 |
| atagattatt | cattagagat | tgaagaaaaa | ataaagaaa | aatttaaaaa | tatagatgtt | 1200 |
| ttaaataatg | aaaatgaata | taagaaatg | attgatatta | tttgtgcaga | gtag | 1254 |

<210> SEQ ID NO 32
<211> LENGTH: 177
<212> TYPE: DNA
<213> ORGANISM: Clostridium difficile

<400> SEQUENCE: 32

| | | | | | |
|---|---|---|---|---|---|
| atgtttagag | ataaaatgga | taaatgtaca | catatgttaa | ctgcttatat | tggtagttca | 60 |
| tatgattatt | gtgattttat | agatacacag | ttagatgatt | ttatattaga | gtacggagaa | 120 |
| aaagttgtgg | aatcttgctt | gcatcaagtg | atggtattgg | taagtaagta | taattag | 177 |

<210> SEQ ID NO 33
<211> LENGTH: 486
<212> TYPE: DNA
<213> ORGANISM: Clostridium difficile

<400> SEQUENCE: 33

| | | | | | |
|---|---|---|---|---|---|
| atgagcaaaa | gtgaattaac | agcagaaaca | acagaagaaa | tgttagaagt | actaagtggt | 60 |
| aaagattatg | atattgcatg | tcatttacat | gaacttggta | aatcattaga | ttgtaaaatt | 120 |

```
gaaccaaaaa caggtgctcg ttcttacaaa atagtatatt caactaagaa accaaaacgt    180
agcttattta ctattgaatg taatgaaaaa aaatggagag ttaaagcaaa tcttttttcat   240 ctaaatacat ataaagatgc tgtggaggaa tgctctaaaa ctattaaaga tagtataact   300
aaaactcgta cttgtaagaa atgtaattca aagtgtattg gaggttcttc gtttgaatta   360
gatggaaagt cttacctgac ttgcatagga agtggtcatt attttgcaaa tatggaagaa   420
atggattgga aaaacctaga aaattaatt actaaagaaa ataatattat gcaggaatct   480
gtatag                                                              486

<210> SEQ ID NO 34
<211> LENGTH: 318
<212> TYPE: DNA
<213> ORGANISM: Clostridium difficile

<400> SEQUENCE: 34
atggactata taggaataga aaatataaca ccttatgaaa atacatatga atttagtgta    60
tatgaatatg atgatgaaat caccttaggt agtgaaaagt tatatgtatg tgaattaagg   120
gttgtattga ttaaagttaa ttctctgtat gttgaaagat tgcataaatc agttgaagca   180
atggtcttag taaaaaattt gaaaaagat ttagataaaa cacttgttgt aaacaaaata   240
aagaattttg tgctagatga gatttgggta gaaaatctag taaaagagaa tatagaagtt   300
atatttgtag aaagctag                                                318

<210> SEQ ID NO 35
<211> LENGTH: 699
<212> TYPE: DNA
<213> ORGANISM: Clostridium difficile

<400> SEQUENCE: 35
atgaaaatat ctagtcaata tagaagtcaa tattcattta gatatgaaag taatataaat    60
aatacaagaa taaatgaaag tatggttaag aaaaatgaaa ctgtaggaaa agacacttat   120
ttatctaata ttatgaaaca aaagcaagaa cttaatgata gaattagaga tttaaaatat   180
agacaagagg tttatactaa aaaaataaat gacgcaatta agaacttatg taaatcagaa   240
ataagagaaa caactaataa tttttctaat atagaaatag gtattaaaaa tagcattata   300
gaagagaaaa ataaaagtac aatgttagat gaaaattcaa cttatctaaa tacaaatgat   360
gaaaaagaat cttaatcac taaagagtct aatgaaaaaa ttgaagaaga aatattaaat   420
gatgaaaaat tagaagagtt agaacaaaaa aaggattata agaggattc taataaaaaa   480 gagaaagtat ctgaggactt atctttagta ggtaaaactc gtgaagagct tgaaaatatg   540
cttaaaaatt ttataaattt aacacaagaa gaaataatga acttgagtc gagaatagaa   600 aagttagata aaaatgctga agaatacaaa caaaattcaa agactaatat atttgataaa   660
acagatgaac aaaaaaaaca tataaatgta ctgatttaa                          699

<210> SEQ ID NO 36
<211> LENGTH: 201
<212> TYPE: DNA
<213> ORGANISM: Clostridium difficile

<400> SEQUENCE: 36
atgtttaaga aaatggcagt actaaaagat atagcaacta aaataggtcg taaaaaagcg    60
tatgaactat tagaaatggt tgaaggtaat gatgcctttg tagctgaggt aaagataaaa   120
aagaatggaa tagaatctaa aaaagaagaa attatgttaa aagataatca aaaaataata   180
```
ttagagtata tagaaggtta a                                              201

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
tgtttatttt gaattttgga ggatt                                           25

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
catgaaaaat agcccatgga a                                               21

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
agatgaaatg gataaatgta cacaca                                          26

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
ccatcacttg atgtaaacaa gattc                                           25

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gggggaacga gcaatttact a                                               21

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
acctacacct ggacgctttg                                                 20

<210> SEQ ID NO 43
<211> LENGTH: 27
<212> TYPE: DNA

```
<213> ORGANISM: Artificial Sequence
<220> FEATURE:
<223> OTHER INFORMATION: Primer

<400> SEQUENCE: 43
tgattgttat tggtgtaatc aagagaa                                              27

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
accctatgaa aacggcttgt t                                                    21

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
ataaagatga agttctgac tctgg                                                 25

<210> SEQ ID NO 46
<211> LENGTH: 27
<212> TYPE: DNA
<213> ORGANISM: Artificial Sequence
<220> FEATURE:
<223> OTHER INFORMATION: Primer

<400> SEQUENCE: 46
ttaaccttat ttactacaat ccaaagg                                              27

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
tgcatatgga aatcaatgtt atagaaa                                              27

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
tgcttcattt aaagcttctt taggata                                              27

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
acctgtcaga ttttggaagc a                                                    21
```

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
tgctaaacct tccaacttga gat                                          23

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
gtcagctttg agggtcgttc                                              20

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
acaatcaatt tccagttgtt tctct                                        25

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
cctttctttt ggatatggat tctc                                         24

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
cagggcaata gcaacaaaca                                              20

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
aagagtgggt ttttgacact ca                                           22

<210> SEQ ID NO 56
<211> LENGTH: 21
<212> TYPE: DNA
<213> ORGANISM: Artificial Sequence
<220> FEATURE:

<223> OTHER INFORMATION: Primer

<400> SEQUENCE: 56
agctccattc acttttgcag t                                    21

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
aaaaaggctc ctgggagaac                                      20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
cggatgaacc tccttttca                                       20

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
ggataaatgt acacatatgt taactgc                              27

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gcaagcaaga ttccacaact                                      20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
accaaaaaca ggtgctcgtt                                      20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
agagcattcc tccacagcat                                      20

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
tgatgaaatc accttaggta gtgaa                                    25

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
cccaaatctc atctagcaca aa                                       22

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
aaaactcgtg aagagcttga aaa                                      23

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
tgaattttgt ttgtattctt cagca                                    25

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
aaaatggcag tactaaaaga tatagca                                  27

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
cctcagctac aaaggcatca                                          20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
tggaaagagc ggagaacttg                                           20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
gatagccacc acttcctcca                                           20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ggtggaaatg gacaagatgg                                           20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
tctccatcat ctgctgcttg                                           20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
tctgtggcca aaagaaaaca                                           20

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
ccacaattaa atcaaaatgg tct                                       23

<210> SEQ ID NO 75
<211> LENGTH: 24
<212> TYPE: DNA
<213> ORGANISM: Artificial Sequence
<220> FEATURE:
<223> OTHER INFORMATION: Primer

<400> SEQUENCE: 75
tcagaagatt ggtatgaaag agga                                      24

<210> SEQ ID NO 76
<211> LENGTH: 21

```
<212> TYPE: DNA
<213> ORGANISM: Artificial Sequence
<220> FEATURE:
<223> OTHER INFORMATION: Primer

<400> SEQUENCE: 76
tggcatttat ggcaacaatt a                                              21

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
ttttgagttt tattgcccaa at                                             22

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ggtaaaccag ctggagcttt                                                20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
atggagtggc gaaacaaaac                                                20

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
gcatgtgcag tttcatgtaa ttct                                           24

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
ggtatagatc tttcagctcc tcca                                           24

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
```

-continued

```
caacagcaat catcacaatc g                                              21

<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
tggcataagg atttaattga tgt                                            23

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
aaacatgata tttccagacc acaa                                           24

<210> SEQ ID NO 85
<211> LENGTH: 27
<212> TYPE: DNA
<213> ORGANISM: Artificial Sequence
<220> FEATURE:
<223> OTHER INFORMATION: Primer

<400> SEQUENCE: 85
actatatgga atttgaagat attcctg                                        27

<210> SEQ ID NO 86
<211> LENGTH: 26
<212> TYPE: DNA
<213> ORGANISM: Artificial Sequence
<220> FEATURE:
<223> OTHER INFORMATION: Primer

<400> SEQUENCE: 86
tttgattgtt ctcttatttc aactgc                                         26

<210> SEQ ID NO 87
<211> LENGTH: 22
<212> TYPE: DNA
<213> ORGANISM: Artificial Sequence
<220> FEATURE:
<223> OTHER INFORMATION: Primer

<400> SEQUENCE: 87 tggttttgc atatacgaat ga                                              22

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
cctcccttcc atctacaatc c                                              21

<210> SEQ ID NO 89
<211> LENGTH: 20
<212> TYPE: DNA
<213> ORGANISM: Artificial Sequence
```

```
<220> FEATURE:
<223> OTHER INFORMATION: Primer

<400> SEQUENCE: 89
gggcagggca aagttgttat                                                   20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
ttttggtcgt gagttgctga                                                   20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
gcatgcaaac attttggtga                                                   20

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
ttcagatacc ttgtcatcat gga                                               23

<210> SEQ ID NO 93
<211> LENGTH: 27
<212> TYPE: DNA
<213> ORGANISM: Artificial Sequence
<220> FEATURE:
<223> OTHER INFORMATION: Primer

<400> SEQUENCE: 93
cctagatgaa agaccaattt tagatga                                           27

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
cagagtcaca atttccacaa cag                                               23

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
atcttgtggg ctgggtattg                                                   20
```

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
cctcctccat gtaccgattt                                               20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
cctccaacag atggaaaacc                                               20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gtactgccca caccttgtga                                               20

<210> SEQ ID NO 99
<211> LENGTH: 22
<212> TYPE: DNA
<213> ORGANISM: Artificial Sequence
<220> FEATURE:
<223> OTHER INFORMATION: Primer

<400> SEQUENCE: 99
caaccaatca taggaacaac ca                                            22

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
tccacaatat ccacattggt c                                             21

<210> SEQ ID NO 101
<211> LENGTH: 26
<212> TYPE: DNA
<213> ORGANISM: Artificial Sequence
<220> FEATURE:
<223> OTHER INFORMATION: Primer

<400> SEQUENCE: 101
tggggatgat aggatgttat actaaa                                        26

<210> SEQ ID NO 102
<211> LENGTH: 23
<212> TYPE: DNA
<213> ORGANISM: Artificial Sequence
<220> FEATURE:
<223> OTHER INFORMATION: Primer

```
<400> SEQUENCE: 102
tccatcatca gatgcttctt gta                                              23

<210> SEQ ID NO 103
<211> LENGTH: 26
<212> TYPE: DNA
<213> ORGANISM: Artificial Sequence
<220> FEATURE:
<223> OTHER INFORMATION: Primer

<400> SEQUENCE: 103
tggatataag agcgttacct ataaga                                           26

<210> SEQ ID NO 104
<211> LENGTH: 21
<212> TYPE: DNA
<213> ORGANISM: Artificial Sequence
<220> FEATURE:
<223> OTHER INFORMATION: Primer

<400> SEQUENCE: 104
tcaactccac ctttccaaaa a                                                21

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
cttgtgacgg gcatgtattg                                                  20

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
tgttttaagc cctcccattg                                                  20

<210> SEQ ID NO 107
<211> LENGTH: 27
<212> TYPE: DNA
<213> ORGANISM: Artificial Sequence
<220> FEATURE:
<223> OTHER INFORMATION: Primer

<400> SEQUENCE: 107
aggttgaaaa tagtagaaaa gaagatg                                          27

<210> SEQ ID NO 108
<211> LENGTH: 25
<212> TYPE: DNA
<213> ORGANISM: Artificial Sequence
<220> FEATURE:
<223> OTHER INFORMATION: Primer

<400> SEQUENCE: 108
tggcttaaac attatactac catga                                            25

<210> SEQ ID NO 109
```

```
<211> LENGTH: 23
<212> TYPE: DNA
<213> ORGANISM: Artificial Sequence
<220> FEATURE:
<223> OTHER INFORMATION: Primer

<400> SEQUENCE: 109
tgtttatttt gaattttgga gga                                           23

<210> SEQ ID NO 110
<211> LENGTH: 26
<212> TYPE: DNA
<213> ORGANISM: Artificial Sequence
<220> FEATURE:
<223> OTHER INFORMATION: Primer

<400> SEQUENCE: 110
catatatcca actcattaag ccatga                                        26

<210> SEQ ID NO 111
<211> LENGTH: 26
<212> TYPE: DNA
<213> ORGANISM: Artificial Sequence
<220> FEATURE:
<223> OTHER INFORMATION: Primer

<400> SEQUENCE: 111
ttcatatttt ataacaaggg gtgatg                                        26

<210> SEQ ID NO 112
<211> LENGTH: 27
<212> TYPE: DNA
<213> ORGANISM: Artificial Sequence
<220> FEATURE:
<223> OTHER INFORMATION: Primer

<400> SEQUENCE: 112
ttctactgtc tcaactttct tcatagc                                       27

<210> SEQ ID NO 113
<211> LENGTH: 25
<212> TYPE: DNA
<213> ORGANISM: Artificial Sequence
<220> FEATURE:
<223> OTHER INFORMATION: Primer

<400> SEQUENCE: 113
tgaaatgttc taattgtgga agtgt                                         25

<210> SEQ ID NO 114
<211> LENGTH: 27
<212> TYPE: DNA
<213> ORGANISM: Artificial Sequence
<220> FEATURE:
<223> OTHER INFORMATION: Primer

<400> SEQUENCE: 114
ttcttatctt tacaccaatt cctatca                                       27

<210> SEQ ID NO 115
<211> LENGTH: 25
<212> TYPE: DNA
<213> ORGANISM: Artificial Sequence
<220> FEATURE:
<223> OTHER INFORMATION: Primer

<400> SEQUENCE: 115
```
gatgaaatgg ataaatgtac acaca 25

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
ccaataccat cacttgatgt aaac 24

<210> SEQ ID NO 117
<211> LENGTH: 25
<212> TYPE: DNA
<213> ORGANISM: Artificial Sequence
<220> FEATURE:
<223> OTHER INFORMATION: Primer

<400> SEQUENCE: 117
tggaaaatga tactattaag gctga 25

<210> SEQ ID NO 118
<211> LENGTH: 23
<212> TYPE: DNA
<213> ORGANISM: Artificial Sequence
<220> FEATURE:
<223> OTHER INFORMATION: Primer

<400> SEQUENCE: 118
ttgcaaaatt gtaagattct cct 23

<210> SEQ ID NO 119
<211> LENGTH: 26
<212> TYPE: DNA
<213> ORGANISM: Artificial Sequence
<220> FEATURE:
<223> OTHER INFORMATION: Primer

<400> SEQUENCE: 119
aatgaaaagt atgattgtta ttggtg 26

<210> SEQ ID NO 120
<211> LENGTH: 27
<212> TYPE: DNA
<213> ORGANISM: Artificial Sequence
<220> FEATURE:
<223> OTHER INFORMATION: Primer

<400> SEQUENCE: 120
ttaatttgga tttgtttata ccctatg 27

<210> SEQ ID NO 121
<211> LENGTH: 23
<212> TYPE: DNA
<213> ORGANISM: Artificial Sequence
<220> FEATURE:
<223> OTHER INFORMATION: Primer

<400> SEQUENCE: 121
aaaattacac ccttagaggc aca 23

<210> SEQ ID NO 122
<211> LENGTH: 27
<212> TYPE: DNA

```
<213> ORGANISM: Artificial Sequence
<220> FEATURE:
<223> OTHER INFORMATION: Primer

<400> SEQUENCE: 122
ttactctttt aagtaaattt ccacctg                                    27

<210> SEQ ID NO 123
<211> LENGTH: 25
<212> TYPE: DNA
<213> ORGANISM: Artificial Sequence
<220> FEATURE:
<223> OTHER INFORMATION: Primer

<400> SEQUENCE: 123
aagatgaaag ttctgactct gggta                                      25

<210> SEQ ID NO 124
<211> LENGTH: 26
<212> TYPE: DNA
<213> ORGANISM: Artificial Sequence
<220> FEATURE:
<223> OTHER INFORMATION: Primer

<400> SEQUENCE: 124
accttattta ctacaatcca aaggtt                                     26

<210> SEQ ID NO 125
<211> LENGTH: 22
<212> TYPE: DNA
<213> ORGANISM: Artificial Sequence
<220> FEATURE:
<223> OTHER INFORMATION: Primer

<400> SEQUENCE: 125
tcaggttgtg gattattttg ga                                         22

<210> SEQ ID NO 126
<211> LENGTH: 27
<212> TYPE: DNA
<213> ORGANISM: Artificial Sequence
<220> FEATURE:
<223> OTHER INFORMATION: Primer

<400> SEQUENCE: 126
tggtaatatt cctctttatc atttgaa                                    27

<210> SEQ ID NO 127
<211> LENGTH: 27
<212> TYPE: DNA
<213> ORGANISM: Artificial Sequence
<220> FEATURE:
<223> OTHER INFORMATION: Primer

<400> SEQUENCE: 127
tgcatatgga aatcaatgtt atagaaa                                    27

<210> SEQ ID NO 128
<211> LENGTH: 25
<212> TYPE: DNA
<213> ORGANISM: Artificial Sequence
<220> FEATURE:
<223> OTHER INFORMATION: Primer

<400> SEQUENCE: 128
tttacaaacc aactagcttt atcca                                      25
```

<210> SEQ ID NO 129
<211> LENGTH: 26
<212> TYPE: DNA
<213> ORGANISM: Artificial Sequence
<220> FEATURE:
<223> OTHER INFORMATION: Primer

<400> SEQUENCE: 129
tttttatcct aatgacatat ttccaa                                              26

<210> SEQ ID NO 130
<211> LENGTH: 25
<212> TYPE: DNA
<213> ORGANISM: Artificial Sequence
<220> FEATURE:
<223> OTHER INFORMATION: Primer

<400> SEQUENCE: 130
agatatgcta aaccttccaa cttga                                               25

<210> SEQ ID NO 131
<211> LENGTH: 27
<212> TYPE: DNA
<213> ORGANISM: Artificial Sequence
<220> FEATURE:
<223> OTHER INFORMATION: Primer

<400> SEQUENCE: 131
ggctggtaat ctaaataata tgagagc                                             27

<210> SEQ ID NO 132
<211> LENGTH: 26
<212> TYPE: DNA
<213> ORGANISM: Artificial Sequence
<220> FEATURE:
<223> OTHER INFORMATION: Primer

<400> SEQUENCE: 132
ccaagtacct atacaatcaa tttcca                                              26

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
ttgtgattga aggtagcgat aaa                                                 23

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
tccaagactt tggaaacttc a                                                   21

<210> SEQ ID NO 135
<211> LENGTH: 21
<212> TYPE: DNA
<213> ORGANISM: Artificial Sequence
<220> FEATURE:

<223> OTHER INFORMATION: Primer

<400> SEQUENCE: 135
gcattggata aaggactgtg c                                           21

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
caagctctgt ctttggagca                                             20

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
tgaaggactt gaccaaaatg aa                                          22

<210> SEQ ID NO 138
<211> LENGTH: 22
<212> TYPE: DNA
<213> ORGANISM: Artificial Sequence
<220> FEATURE:
<223> OTHER INFORMATION: Primer

<400> SEQUENCE: 138
tttttctttc cacctctttt ga                                          22

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139
catggaataa ttcgagtgtt gaa                                         23

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
gttctcccag gagccttttt                                             20

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
tgaatgatat ggcaagagat gt                                          22

```
<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
cctgttcccc aatcaatctg                                              20

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
tgcaccataa ttgttagagc aaa                                          23

<210> SEQ ID NO 144
<211> LENGTH: 25
<212> TYPE: DNA
<213> ORGANISM: Artificial Sequence
<220> FEATURE:
<223> OTHER INFORMATION: Primer

<400> SEQUENCE: 144
tttttatttt tagtgcacac tctcc                                        25

<210> SEQ ID NO 145
<211> LENGTH: 27
<212> TYPE: DNA
<213> ORGANISM: Artificial Sequence
<220> FEATURE:
<223> OTHER INFORMATION: Primer

<400> SEQUENCE: 145
ggataaatgt acacatatgt taactgc                                      27

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
cttgatgcaa gcaagattcc                                              20

<210> SEQ ID NO 147
<211> LENGTH: 23
<212> TYPE: DNA
<213> ORGANISM: Artificial Sequence
<220> FEATURE:
<223> OTHER INFORMATION: Primer

<400> SEQUENCE: 147
aaagaagcaa tgaaaaacga gaa                                          23

<210> SEQ ID NO 148
<211> LENGTH: 25
<212> TYPE: DNA
<213> ORGANISM: Artificial Sequence
<220> FEATURE:
<223> OTHER INFORMATION: Primer
```

<400> SEQUENCE: 148 tttctactt aacctttcag gtcca                                    25

<210> SEQ ID NO 149
<211> LENGTH: 23
<212> TYPE: DNA
<213> ORGANISM: Artificial Sequence
<220> FEATURE:
<223> OTHER INFORMATION: Primer

<400> SEQUENCE: 149
tgagcaaaag tgaattaaca gca                                     23

<210> SEQ ID NO 150
<211> LENGTH: 21
<212> TYPE: DNA
<213> ORGANISM: Artificial Sequence
<220> FEATURE:
<223> OTHER INFORMATION: Primer

<400> SEQUENCE: 150
ttttccaatc catttcttcc a                                       21

<210> SEQ ID NO 151
<211> LENGTH: 26
<212> TYPE: DNA
<213> ORGANISM: Artificial Sequence
<220> FEATURE:
<223> OTHER INFORMATION: Primer

<400> SEQUENCE: 151
gatgatgaaa tcaccttagg tagtga                                  26

<210> SEQ ID NO 152
<211> LENGTH: 23
<212> TYPE: DNA
<213> ORGANISM: Artificial Sequence
<220> FEATURE:
<223> OTHER INFORMATION: Primer

<400> SEQUENCE: 152
acccaaatct catctagcac aaa                                     23

<210> SEQ ID NO 153
<211> LENGTH: 23
<212> TYPE: DNA
<213> ORGANISM: Artificial Sequence
<220> FEATURE:
<223> OTHER INFORMATION: Primer

<400> SEQUENCE: 153
aatgttccat ttgactatgt tcg                                     23

<210> SEQ ID NO 154
<211> LENGTH: 21
<212> TYPE: DNA
<213> ORGANISM: Artificial Sequence
<220> FEATURE:
<223> OTHER INFORMATION: Primer

<400> SEQUENCE: 154
ggaggaaatt catcatctcc a                                       21

<210> SEQ ID NO 155
<211> LENGTH: 26

```
<212> TYPE: DNA
<213> ORGANISM: Artificial Sequence
<220> FEATURE:
<223> OTHER INFORMATION: Primer

<400> SEQUENCE: 155
tggttaagaa aaatgaaact gtagga                                        26

<210> SEQ ID NO 156
<211> LENGTH: 22
<212> TYPE: DNA
<213> ORGANISM: Artificial Sequence
<220> FEATURE:
<223> OTHER INFORMATION: Primer

<400> SEQUENCE: 156
gcatattttc aagctcttca cg                                            22

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
ttcaagaaag cattcctatc aca                                           23

<210> SEQ ID NO 158
<211> LENGTH: 27
<212> TYPE: DNA
<213> ORGANISM: Artificial Sequence
<220> FEATURE:
<223> OTHER INFORMATION: Primer

<400> SEQUENCE: 158
tctttgctta caactatacc acctttt                                       27

<210> SEQ ID NO 159
<211> LENGTH: 27
<212> TYPE: DNA
<213> ORGANISM: Artificial Sequence
<220> FEATURE:
<223> OTHER INFORMATION: Primer

<400> SEQUENCE: 159
tgtttaagaa aatggcagta ctaaaag                                       27

<210> SEQ ID NO 160
<211> LENGTH: 27
<212> TYPE: DNA
<213> ORGANISM: Artificial Sequence
<220> FEATURE:
<223> OTHER INFORMATION: Primer

<400> SEQUENCE: 160
tttttatctt tacctcagct acaaagg                                       27

<210> SEQ ID NO 161
<211> LENGTH: 25
<212> TYPE: DNA
<213> ORGANISM: Artificial Sequence
<220> FEATURE:
<223> OTHER INFORMATION: Primer

<400> SEQUENCE: 161
```

```
ttgttgttta tgctaataat gtgga                                          25

<210> SEQ ID NO 162
<211> LENGTH: 27
<212> TYPE: DNA
<213> ORGANISM: Artificial Sequence
<220> FEATURE:
<223> OTHER INFORMATION: Primer

<400> SEQUENCE: 162
ttctattttt gaaaactctt ctttctc                                        27
```